(12) United States Patent
Cook et al.

(10) Patent No.: US 7,595,395 B2
(45) Date of Patent: Sep. 29, 2009

(54) GABAERGIC AGENTS TO TREAT MEMORY DEFICITS

(75) Inventors: James M. Cook, Whitefish Bay, WI (US); Dongmei Han, Houston, TX (US); Terry Clayton, Wauwatosa, WI (US)

(73) Assignee: WiSys Technology Foundation, Madison, WI (US)

( * ) Notice: Subject to any disclaimer, the term of this patent is extended or adjusted under 35 U.S.C. 154(b) by 69 days.

(21) Appl. No.: 11/383,624

(22) Filed: May 16, 2006

(65) Prior Publication Data

US 2006/0258643 A1 Nov. 16, 2006

Related U.S. Application Data

(60) Provisional application No. 60/594,880, filed on May 16, 2005.

(51) Int. Cl.
*C07D 487/04* (2006.01)
(52) U.S. Cl. ................................. 540/498
(58) Field of Classification Search .............. 540/498; 514/220
See application file for complete search history.

(56) References Cited

U.S. PATENT DOCUMENTS

| | | | |
|---|---|---|---|
| 4,316,839 A | 2/1982 | Gerecke et al. | |
| 4,346,030 A * | 8/1982 | Gerecke et al. | 540/494 |
| 4,352,815 A | 10/1982 | Hunkeler et al. | |
| 4,352,817 A | 10/1982 | Hunkeler et al. | |
| 4,489,003 A | 12/1984 | Hunkeler et al. | |
| 4,775,671 A | 10/1988 | Hunkeler et al. | |
| 5,665,718 A | 9/1997 | Godel et al. | |

OTHER PUBLICATIONS

Bailey et al., "Effects of Hippocampal injections of a novel lignad selective for the alpha5beta2gamma 2 subunits...," Neurbiology of Learning and Memory, 2002, 78:1-10.
Cooke et al., "[alpha]-Subunit selective modulators of GABAA receptor function as CNS Therapeutics," Expert Opinon on Ther. Patents, 2002, 12(10):1491-1501.
Han et al., "Determination of the stable conformation of GABAa-denzodiazepine receptor . . .," Bioorganic & Medicinal Chem. Letters, 2004, 14:1465-1469.
He et al., "Pharmacophoren/Receptor Models for GABAA/BZR ALPHABETA3GAMMA2 . . .," Drug Design and Discovery, 2000, 17(2):131-171.
Huang et al., "Pharacophore/Receptor Models for GABAa/BZR Subtypes (alpha1beta3gamma2,alpha5,beta3,gamma2,and alpha6,beta3,gamma2). . .," J of Med Chem, 2000, 43:71-95.
Li et al., "Synthesis, in vitro affinity, and efficacy of a bis 8-ethynyl-4H-imidazo [1,5a]-[1,4]benzodiazepine analogue . . .," J Med Chem, 2003, 46(26):5567-5570.
Templeton et al., "A double-blind, placebo-controlled single dose trial of intravenous flumazenil in Alzheimer's disease," Hum. Psychopharmacol. Clin Exp., 1999, 14:239-245.

* cited by examiner

*Primary Examiner*—Bruck Kifle
(74) *Attorney, Agent, or Firm*—Quarles & Brady LLP

(57) ABSTRACT

The present invention provides molecules and methods for the prevention and/or treatment of memory deficit related conditions and/or enhancement of cognizance. In a preferred embodiment, the invention includes compounds, salts and prodrugs thereof for the prevention and/or treatment of these conditions.

1 Claim, 21 Drawing Sheets

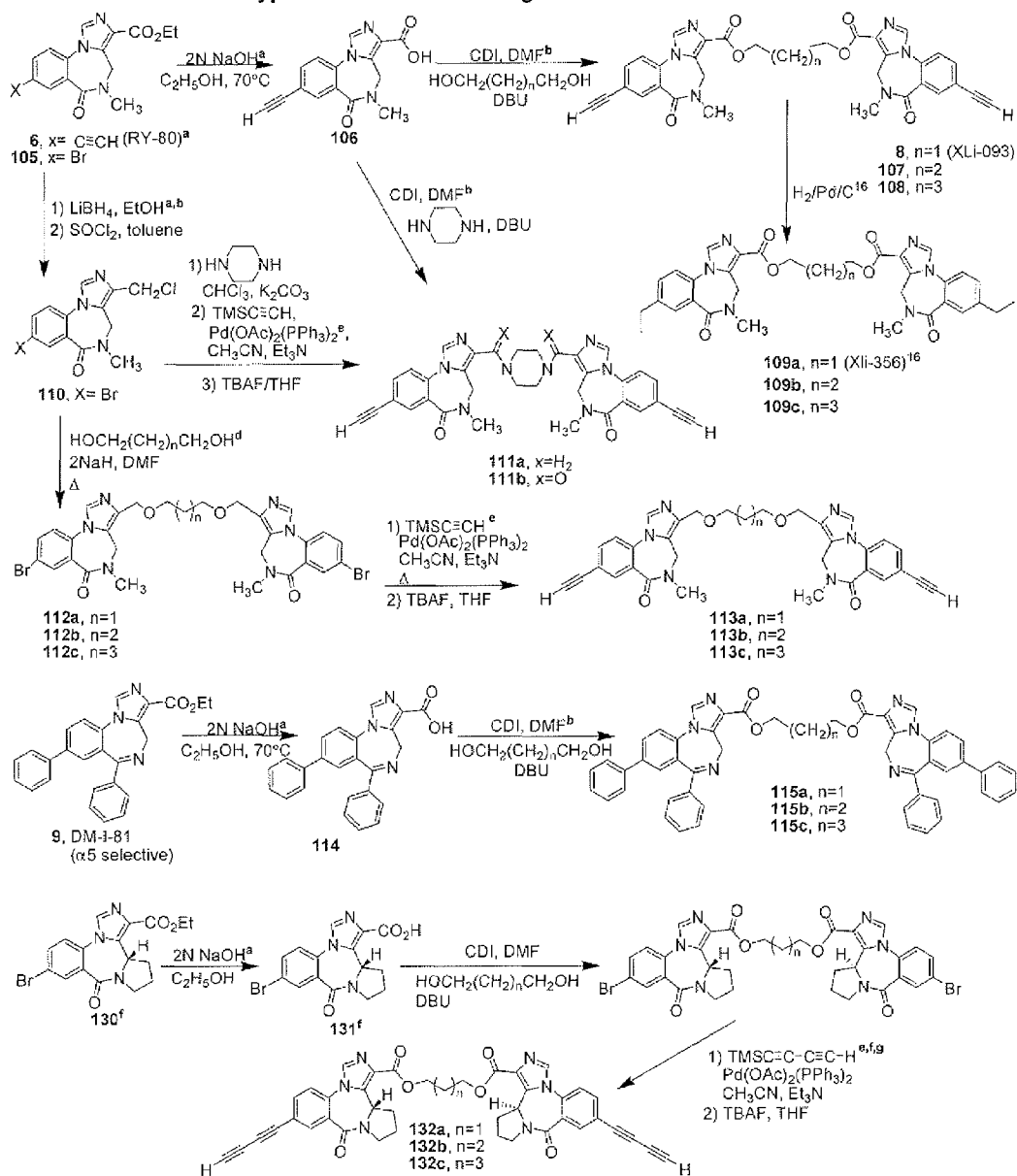

FIG 1-Scheme 8
α5 Subtype Selective Bivalent Ligands Based on XLI-093 a) Li, X.; Cao, H.; Zhang, C.; Fürtmueller, R.; Fuchs, K.; Huck, S.; Sieghart, W.; Deschamps, J.; Cook, J.; *J. Med. Chem.*, 46, 5567 (2003). b) see reference a. c) Wong, G.; Koehler, K.; Skolnick, P.; Gu, Z-Q; Ananthan, S.; Schronholzer, P.; Hunkeler, W.; Zhang, W.; Cook, J.; *J. Med. Chem.*, 36, 1820 (1993). d) see ref. c. e) Liu, R.; Hu, R.; Zhang, P.; Skolnick, P.; Cook, J.; *J. Med. Chem.*, 39, 1928 (1996). f) Fryer, R.; Gu, Z.; Wang, C., *J. Heterocyclic Chem.*, 28, 1661 (1991). Li, X.; Yu, J.; Atack, J.; Cook, J., *Med. Chem. Res.*,13, 259 (2004). g) The trimethylsilylbisacetylene has been prepared on 5 gram scale [ see He, X. PhD thesis, University of Wisconsin-Milwaukee, Milwaukee, WI, (2000).].

a5 Selective Antagonist

| Ligand | a1 | a2 | a3 | a4 | a5 | a6 |
|---|---|---|---|---|---|---|
| RY-80 | 28.8 | 21.4 | 25.8 | 53 | 0.49 | 28.8 |
| XLi093 | >1000 | >1000 | 858 | 1550 | 15 | >2000 |

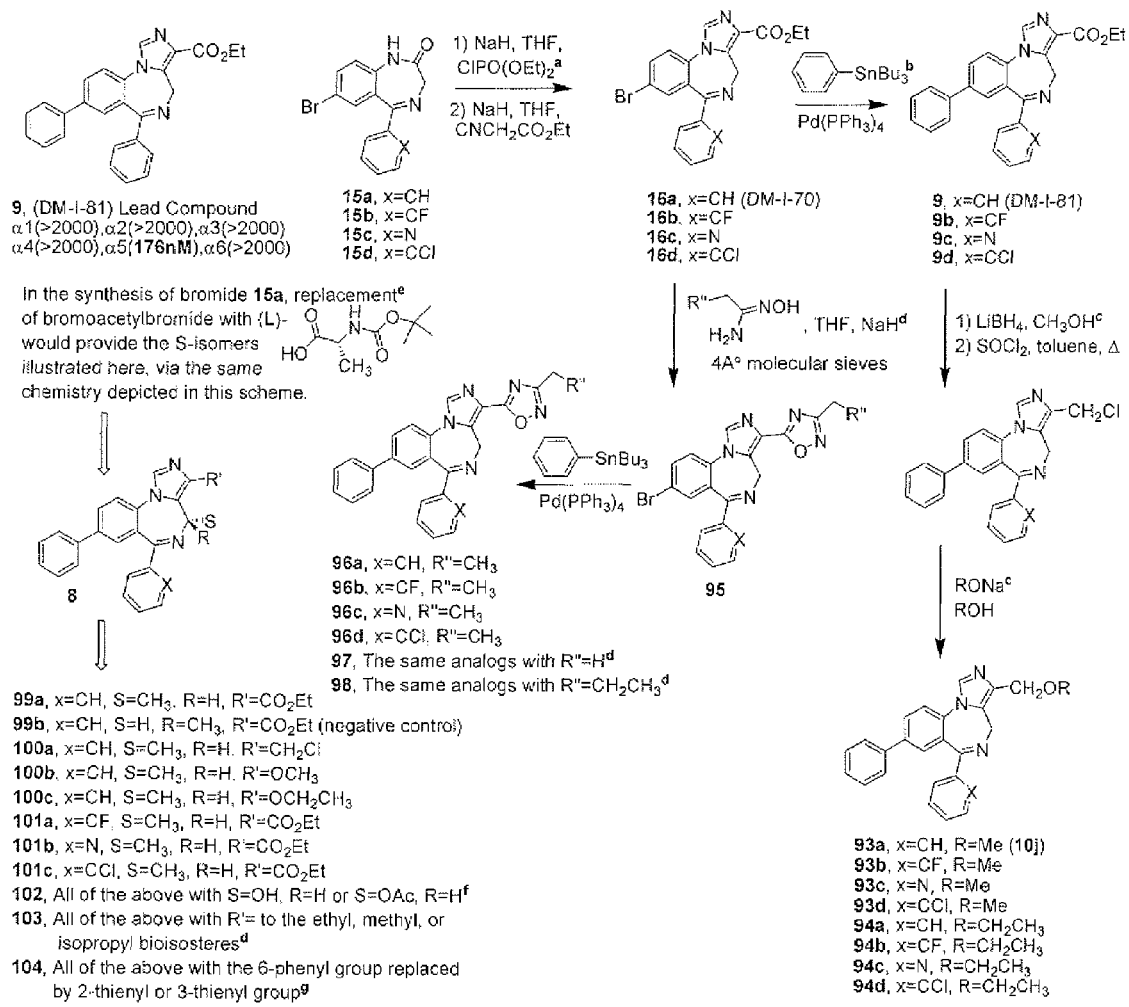

Fig.5 a) Fryer, R.; Schmidt, R.; Sternbach, L.; *J. Pharm. Sci.*, 53, 264(1964). Fryer, R.; Gu, Z.; Wang, C., *J. Heterocyclic. Chem.*, 28, 1661 (1991). b) Stille, J.K., *Agnew. Chem. Int. Ed. Engl.*, 25, 508 (1986). c) Wong, G.; Koehler, K.; Skolnick, P.; Gu, Z-Q; Ananthan, S.; Schonholzer, Hunkeler, W.; Zhang, W.; Cook, J.; *J. Med. Chem.*, 36, 1820 (1993). d) Fryer, R.; Zhang, P.; Lin, K.; Upasani, R.; Wong, G.; Skolnick, P.; *Med. Chem. Res.*, 3, 183 (1993), Watjen, f.; Baker, R.; Engelstoff, M.; Herbert, r.; Macleod, A.; Knight. A.; Merchant, K.; Moseley, J.; Saunders, J.; Swain, J.; Wong, E.; Springer, J., *J. Med. Chem.*, 32, 2282 (1989). e) Hart, B.; Rush, D.; Shea, K., *J. Am. Chem. Soc.*, 122, 460 (2000). f) Optical resolution of the (R)-4-hydroxy or acetoxy analogs can be carried out on a chiral column as executed earlier with oxazepam [see Blaschke, G.; Markgraf, H.; *Chem. Ber.*, 113, 2031 (1980)]. g) see citation d, above.

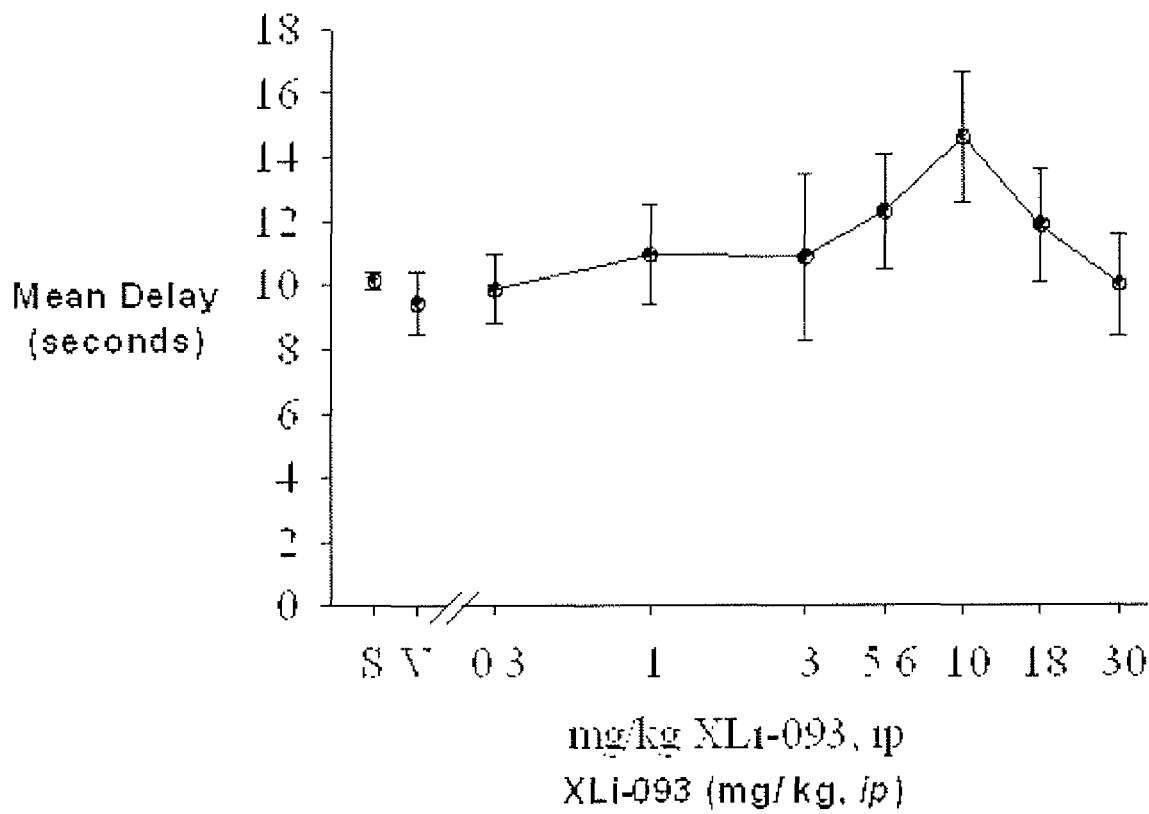
Fig. 6
Fig. 7
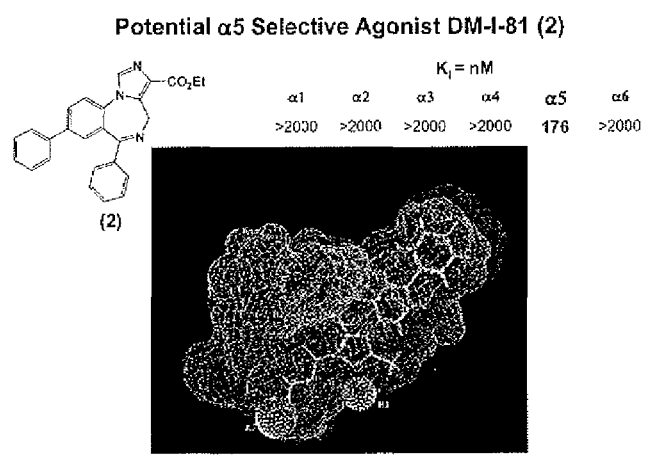
DM-I-81 aligned in the included volume of the pharmacophore/receptor model for the α1β3γ2 (light grey) and α5β3γ2 (dark grey) subtypes.

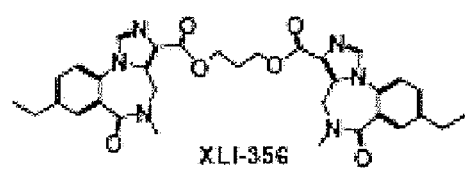
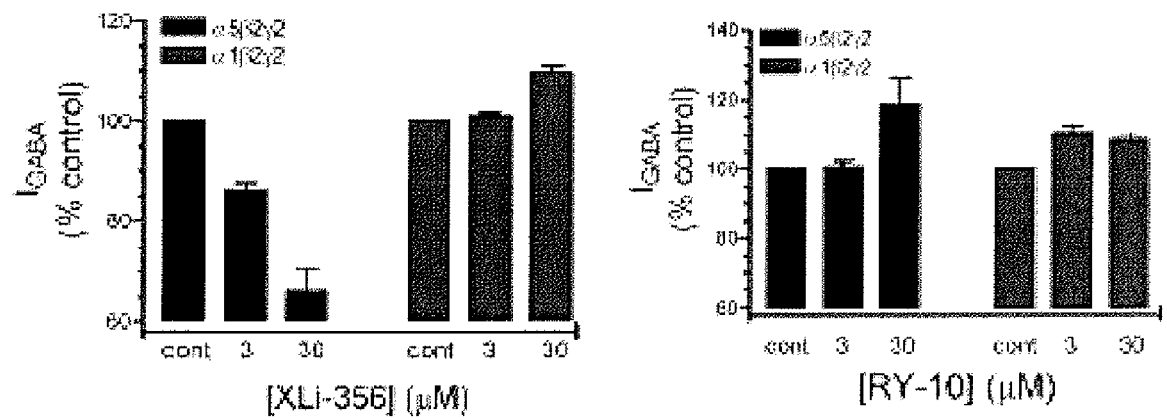
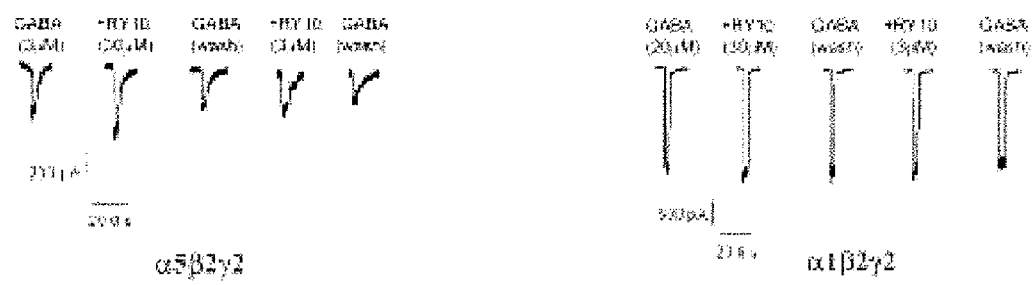
Fig. 8

Fig. 11
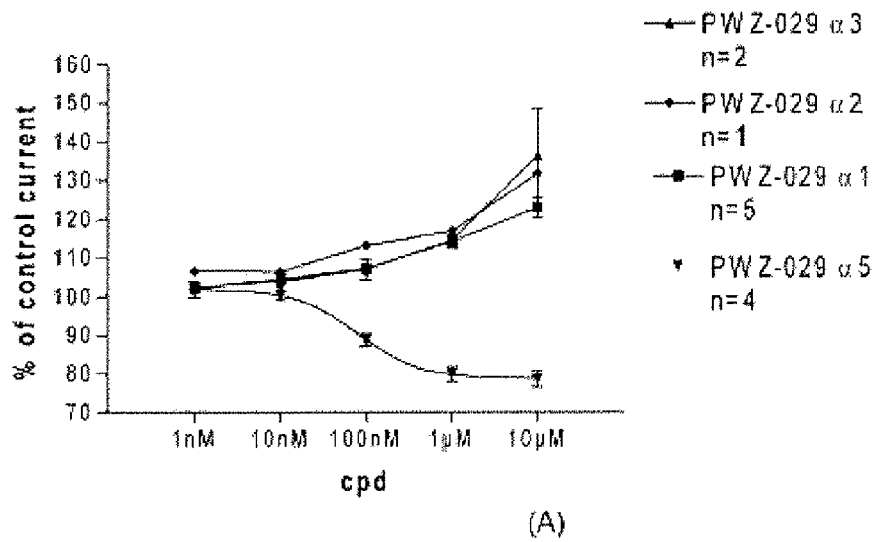
(A)
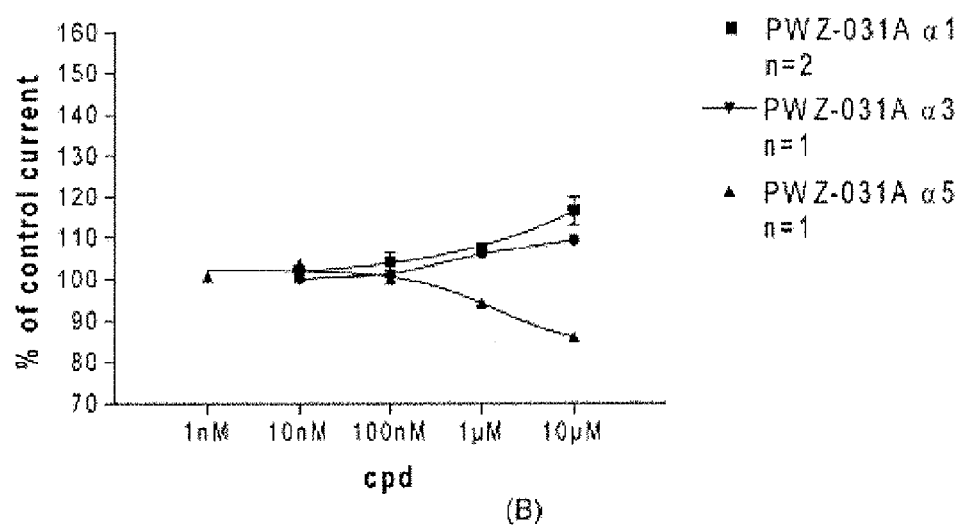
(B)
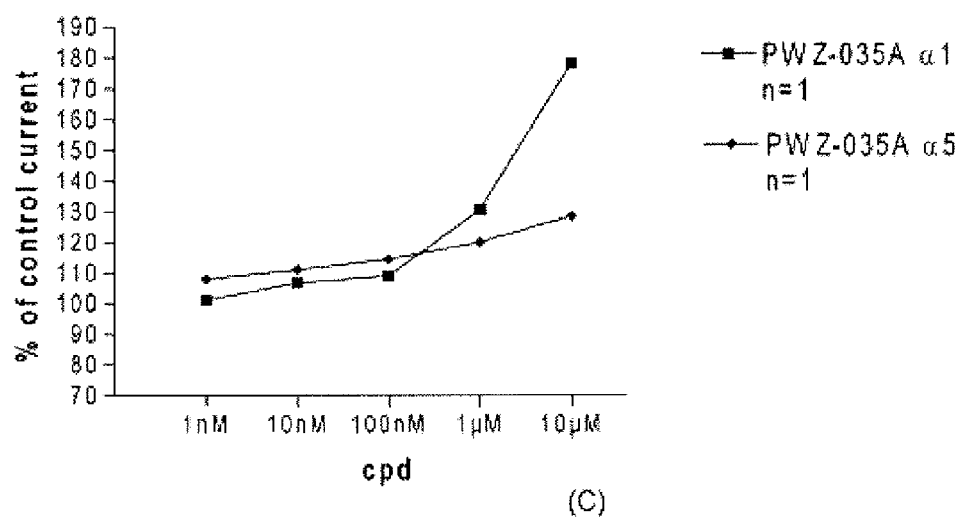
(C)

Whiting, *et al.*,

J Neurosci. 1997;17: 5027-37

See Also:

Sigel, E., and R. Baur (1988). *Allosteric modulation by benzodiazepine receptor ligands of the GABA_A receptor channel expressed in Xenopus oocytes.* J Neurosci.8(1):289-95.

Thomet, U., R. Baur, P. Scholze, W. Sieghart, and E. Sigel (1999) *Dual mode of stimulation by the beta-carboline ZK 91085 of recombinant GABA(A) receptor currents: molecular determinants affecting its action.* Br J Pharmacol.127(5):1231-9.

PWZ-029    $C_{14}H_{14}ClN_3O_2$

| α1 | α2 | α3 | α4 | α5 | α6 |
|---|---|---|---|---|---|
| >300 | >300 | >300 |  | 38.8 | >300 |

- ■ XLi 356 a1
- ▲ XLi 356 a5
- ▼ XLi 356 a2
- ♦ XLi 356 a3

| Compound | Formula | MW | a1 | a2 | a3 | a4 | a5 | a6 |
|---|---|---|---|---|---|---|---|---|
| XLI093 | C33H26N6O6 | 602.59614 | 1000 | 1000 | 858 | 1550 | 15 | 2000 |

GABAERGIC AGENTS TO TREAT MEMORY DEFICITS

RELATED APPLICATION

The present application seeks priority from U.S. Provisional Application No. 60/594,880 filed on May 16, 2005, which is incorporated by reference in its entirety, as if fully set forth herein.

STATEMENT REGARDING FEDERAL FUNDING

This invention was supported in part with NIMH grant number MH46851. The Federal Government may have certain rights in this invention.

TECHNICAL BACKGROUND

The present invention generally relates to treatment of memory deficits, specifically the invention provides molecules and methods related to the synthesis of inverse agonists and agonists for the treatment of memory-related diseases such as dementia and Alzheimer's disease.

BACKGROUND OF THE INVENTION

The life expectancies of men and women have increased substantially during the last fifty years. Inevitably, this development will lead to largely increased numbers of elderly people. Many of them will be afflicted by dementia.

Senile dementia of the Alzheimer's type (SDAT) accounts for the major portion of all neurodegenerative diseases (Sarter and Bruno 1997). Within the U.S.A. alone, about 4 million individuals are afflicted with SDAT, with about 130,000 new cases occurring per year (Small 1997; Anger 1991). Annual costs associated with Alzheimer's disease are estimated to exceed $100 billion (Ernst et al. 1997).

Epidemiologists expect that by the year 2050 in the more developed world, life expectancies at birth will surpass 80 years of age (Froestl 2004; Katzman et al. 1999). Inevitably, this development will lead to increased numbers of elderly people, from 414 million people over 65 years of age in 2000 to probably 1.4 billion in the year 2050 (Katzman et al. 1999). Many of them will be afflicted by dementia, the prevalence of which rises rapidly with very old age. According to a Canadian study, the prevalence of dementia is about 23% in people of the age group 85-89 years, about 40% in people of the age group 90-94 years, whereas in people older than 95 years the prevalence of dementia rises to about 58% (Froestl 2004; Ebly et al. 1994). In 2002, the number of individuals suffering from dementia in the developed world was about 13.5 million cases. This figure is expected to rise to 37 million by the year 2050 and to 105 million worldwide by 2050 (Froestl 2004; Katzman et al. 1999; CIA World Factbook 2002).

SDAT and age-related memory decline arises from progressive failure of the cholinergic system, leading to impaired memory and deterioration of other cognitive functions (Perry et al. 1992; Whitehouse 1998). Pharmacological treatment for this cognitive decline has primarily focused on cholinomimetrics and cholinesterase inhibitors to mitigate the cholinergic hypofunction. These strategies tend to elicit direct postsynaptic stimulation. The constant tonic neuronal activity which results is unfavorable to normal cognitive processing, which seriously undercuts the usefulness of this standard approach (Sarter and Bruno 1997).

A more effective strategy to alleviate memory deficits attributed to cholinergic hypofunction would be to enhance cognitive processing by augmenting the impact that acetylcholine (ACh) released from surviving cholinergic neurons on hippocampal pyramidal cells, without disrupting the highly complex transmission patterns inherent to these cortical cholinergic pathways (Sarter and Bruno 1994, 1997).

Receptors for the major inhibitory neurotransmitter, gamma-aminobutyric acid (GABA), are divided into three main classes: (1) $GABA_A$ receptors, which are members of the ligand-gated ion channel superfamily; (2) $GABA_B$ receptors, which may be members of the G-protein linked receptor superfamily; and (3) $GABA_C$ receptors, also members of the ligand-gated ion channel superfamily, but their distribution is confined to the retina. Benzodiazepine receptor ligands do not bind to $GABA_B$ and $GABA_C$ receptors. Since the first cDNAs encoding individual $GABA_A$ receptor subunits were cloned the number of known members of the mammalian family has grown to 21 including α, β, and γ subunits (6α, 4β, 4γ, 1δ, 1ε, 1π, 1θ, and 3ρ).

Subtype assemblies containing an α1 subunit (α1β2γ2) are present in most areas of the brain and are thought to account for 40-50% of $GABA_A$ receptors in the rat brain. Subtype assemblies containing α2 and α3 subunits respectively are thought to account for about 25% and 17% $GABA_A$ of the receptors in the rat CNS. Subtype assemblies containing an α5 subunit (α5β3γ2) are expressed predominately in the hippocampus and cortex and are thought to represent about 4% of $GABA_A$ receptors in the rat brain.

A characteristic property of all known $GABA_A$ receptors is the presence of a number of modulatory sites, one of which is the benzodiazepine binding site. The benzodiazepine binding site is the most explored of the $GABA_A$ receptor modulatory sites, and is the site through which benzodiazepine-based anxiolytic drugs exert their effect. Before the cloning of the $GABA_A$ receptor gene family, the benzodiazepine binding site was historically subdivided into two subtypes, BENZODIAZEPINE1 and BENZODIAZEPINE2, on the basis of radioligand binding studies on synaptosomal rat membranes. The BENZODIAZEPINE1 subtype has been shown to be pharmacologically equivalent to a $GABA_A$ receptor comprising the α1 subunit in combination with a β subunit and γ2. This is the most abundant $GABA_A$ receptor subtype, and is believed to represent almost half of all $GABA_A$ receptors in the brain, as stated.

Two other major populations are the α2β⅔γ2 and α3β⅔γ2 subtypes. Together these constitute approximately a further 35% of the total $GABA_A$ receptor population. Pharmacologically this combination appears to be equivalent to the BENZODIAZEPINE2 subtype as defined previously by radioligand binding, although the BENZODIAZEPINE2 subtype may also include certain α5-containing subtype assemblies. The physiological role of these subtypes has hitherto been unclear because no sufficiently selective agonists or antagonists were known.

It is now believed that agents acting as benzodiazepine agonists at $GABA_A/α2$, $GABA_A/α3$, and/or $GABA_A/α5$ receptors, will possess desirable anxiolytic properties. Compounds which are modulators of the benzodiazepine binding site of the $GABA_A$ receptor by acting as benzodiazepine agonists are referred to hereinafter as "$GABA_A$ receptor agonists." The $GABA_A/α1$-selective (α1β2γ2) agonists alpidem and zolpidem are clinically prescribed as hypnotic agents, suggesting that at least some of the sedation associated with known anxiolytic drugs which act at the BENZODIAZEPINE1 binding site is mediated through $GABA_A$ receptors containing the α1 subunit. Accordingly, it is considered that GABA$_A$/α2, GABA$_A$/α3, and/or GABA$_A$/α5 receptor agonists rather than GABA$_A$/α1 receptors will be effective in the treatment of anxiety with a reduced propensity to cause sedation. For example, QH-ii-066 binds with high affinity to GABA$_A$/α5 receptors (Ki<10 nM), intermediate affinity to GABA$_A$/α2 and GABA$_A$/α3 (Ki<50 nM), and lower affinity to GABA$_A$/α1 receptors (Ki>70 nM), unlike diazepam which binds with high affinity to all four diazepam-sensitive GABA$_A$ receptors (Ki<25 nM), as disclosed in Huang, et al., J. Med. Chem. 2000, 43, 71-95 and WO 03/082832A2. Also, agents which are antagonists or inverse agonists at α1 receptors might be employed to reverse sedation or hypnosis caused by α1 agonists.

An exciting yet largely underdeveloped therapeutic approach with excellent potential to achieve this outcome is one that would reduce postsynaptic inhibition of cholinergic excitation in the hippocampus via pharmacology (Froestl 2004). A rational means to achieve this aim is to influence the functional regulation pathways involved in cognition by manipulating the inhibitory nature of the neurotransmitter GABA (Bailey et al. 2002; DeLorey et al., 2001; Chambers et al. 2002, 2003). When GABA binds to the GABA/benzodiazepine receptor, it induces chloride ion (Cl$^-$) passage into the neuron, causing hyperpolarization of the surrounding membrane preventing synaptic excitation. GABA's inhibitory effects can be fine-tuned by a variety of substances, including those that specifically bind to the benzodiazepine binding site (BzR) on the GABA receptor (Bailey et al. 2002; DeLorey et al. 2001; Chambers et al. 2002, 2003). Appropriate BzR ligands modulate GABA's inhibitory influence on numerous neuronal pathways, including the cholinergic pathways of the basal forebrain that project to the hippocampus (Sarter and Bruno 1997). These cholinergic pathways are important to cognition and are prone to degeneration in SDAT. Although BzR ligands are relatively safe drugs, their downside is due to their broad spectrum of activity and lack of behavioral specificity. Consequently, insight into how BzR ligands elicit their specific physiological effect is crucial to development of the next generation of behaviorally-specific BzR ligands with reduced side effects. This invention provides such insight.

BzR ligands alone do not activate GABA$_A$ receptors, but instead act as modulators of GABA's ability to activate this receptor. For example, when cognitive events activate cholinergic excitation in the hippocampus, the GABAergic system is likewise activated to modulate the level of this excitation. In situations where the cholinergic excitation is decreased due to the loss of cholinergic neurons, as in the case in SDAT, the precise reduction in GABAergic inhibition in brain regions where the weakened cholinergic neurons project would selectively augment the functional impact of the ACh released (Sarter and Bruno 1997; Abe et al. 1998). It is important to point out that GABAergic neurons remain intact and functional until the very last stages of Alzheimer's disease while cholinergic deficits become more pronounced as the disease progresses (Howell et al. 2000; Quirk et al. 1996).

Consequently, α5 BzR/GABAergic neurons have now become pharmacological targets because these are located almost exclusively in the hippocampus (Howell et al. 2000; Quirk et al. 1996) and are still functional throughout most stages of the disease. It is well documented that the BzR ligands flunitrazepam and midazolam impair cognition in animal models and humans (Costa and Guidotti 1996) by augmenting GABA-mediated Cl$^-$ flux through the GABA$_A$ receptor, which prevents the induction of Long Term Potentiation (LTP) in rodent hippocampal neurons (Evans and Viola-McCabe 1996; Seabrook et al. 1997).

Conversely, BzR ligands that retard GABA-mediated Cl$^-$ passage into the neuron potentiate LTP in rodent hippocampal neurons (Seabrook et al. 1997; Kawasaki et al. 1996), resulting in improved learning and memory (Duka and Dorrow 1995). Earlier, the therapeutic potential for memory augmentation by BzR ligands has been considered to be limited due to the side effects such as convulsant or proconvulsant activity that occur at slightly higher doses (Potier et al. 1988). However, new findings suggest that particular combinations of GABA$_A$ receptor subunits are intimately associated with cognitive influence (Crestani et al. 2002; Möhler et al. 2004) and will not be convulsant/proconvulsant.

The intense search for drugs for treatment of dementia has produced only 5 drugs on the market, all of which have certain limitations. Accordingly, the need exists for new methods, molecules and technologies to work towards eliminating these limitations of commercially available memory-deficient treatments.

SUMMARY OF THE INVENTION

The present invention generally provides molecules and methods for the treatment and/or prevention and/or memory enhancement in patients in risk thereof. In one embodiment, the present invention provides a compound of Formula IV, a salt or a prodrug thereof,

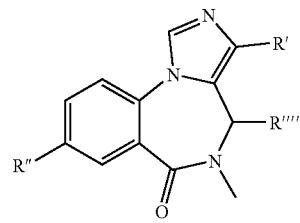

IV wherein R' is branched or straight chain C1 to C4 alkyl or a methyl cyclopropyl, OMe, OEt, COOMe, COOEt, COO-i-Pr, COO-t-Bu, CH$_2$R$_1$, wherein R$_1$ is OH, Cl, OMe, OEt N(Et)$_2$, N(iPr)$_2$ or

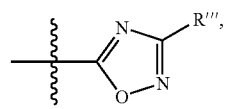

wherein R'" is H or branched or straight chain C1 to C4 alkyl or a methyl cyclopropyl, —CH$_2$—OMe, —CH$_2$—OEt, —CH$_2$—O-iPr, —CH$_2$—O-tBu, —COMe, —COEt, —COPr, —COBu, —CO-iPr, —CO-t-Bu;

R" is F, Cl, Br, NO$_2$, Et, —C≡C—R$_2$, —C≡C—C≡C—R$_2$, where R$_2$ is H, Si (CH$_3$)$_3$, t-butyl, isopropyl, methyl, or cyclopropyl; and R"" is H or branched or straight chain C1 to C4 alkyl or a methyl cyclopropyl.

In this embodiment, preferably, the compound, salt or prodrug of Formula IV, selectively binds to α$_5$β$_2$γ$_2$ or α$_5$β$_3$γ$_2$ receptors. More preferably, the compound of Formula IV is

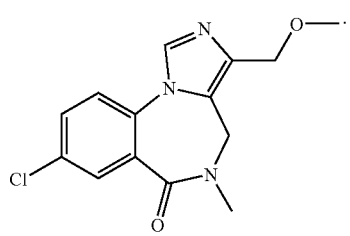

In a preferred exemplary embodiment, the compounds of Formula I are shown below:

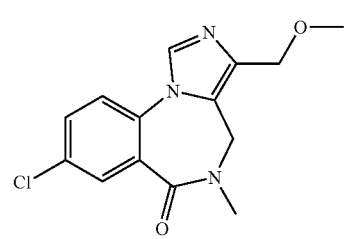

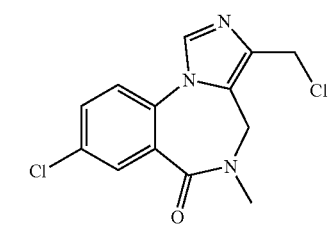

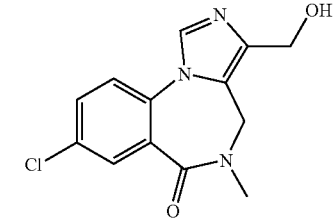

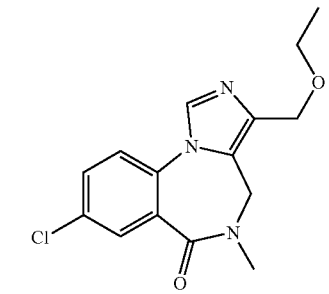

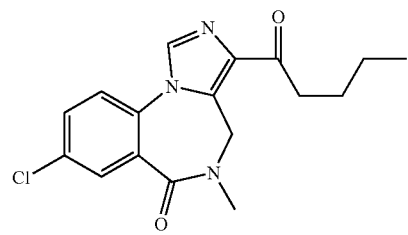

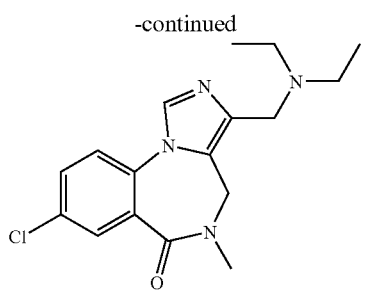

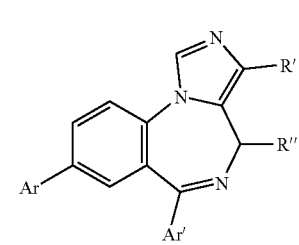

In a preferred embodiment, the present invention provides a compound of Formula I, a salt or a prodrug thereof, wherein Formula is depicted as shown below:

I wherein:

Ar is phenyl or thienyl;

Ar' is a substituted or unsubstituted 5 membered or a 6 membered carbocyclic ring, or a 5 or 6 membered heterocylic ring having at least one heteroatom selected from N, O and S, wherein if substituted, the substituent is one or more of F, Cl, Br or $NO_2$ at the 2'-position;

R' is OMe, OEt, $CO_2$Et, $CH_2$R, wherein R is OH, Cl, OMe or OEt or

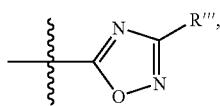

wherein R''' is H or branched or straight chain C1 to C4 alkyl or a methyl cyclopropyl;

R'' is H or (R) or (S) CH$_3$, OH, OAc, NO$_2$, OCON(CH$_3$)$_2$, COOCH$_3$, COOCH$_2$CH$_3$.

In a preferred exemplary embodiment, the compounds of Formula I are shown below:

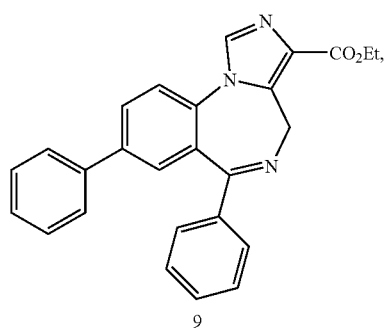

9

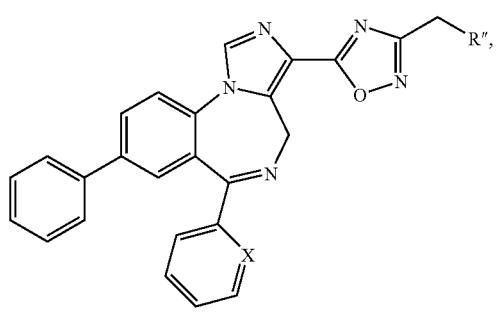

96a, x = CH, R'' = CH$_3$
96b, x = CF, R'' = CH$_3$
96c, x = N, R'' = CH$_3$
96d, x = CCl, R'' = CH$_3$
97, The same analogs with R'' = H[d]
98, The same analogs with R'' = CH$_2$CH$_3$[d]

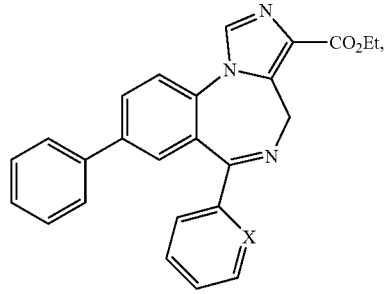

9b, x = CF
9c, x = N
9d, x = CCl

-continued

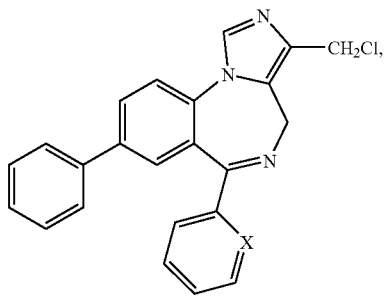

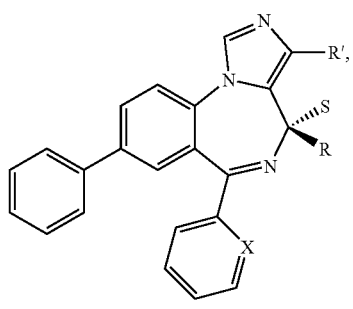

8
99a, x = CH, R = CH$_3$, S = H, R' = CO$_2$Et
99b, x = CH, R = H, S = CH$_3$, R' = CO$_2$Et (negative control)
100a, x = CH, R = CH$_3$, S = H, R' = CH$_2$Cl
100b, x = CH, R = CH$_3$, S = H, R' = OCH$_3$
100c, x = CH, R = CH$_3$, S = H, R' = OCH$_2$CH$_3$
101a, x = CF, R = CH$_3$, S = H, R' = CO$_2$Et
101b, x = N, R = CH$_3$, S = H, R' = CO$_2$Et
101c, x = CCl, R = CH$_3$, S = H, R' = CO$_2$Et
102, All of the above with R = OH, S = H or R = OAc, S = H[f]
103, All of the above with R' = to the ethyl, methyl, or isopropyl bioisosteres[d]
104, All of the above with the 6-phenyl group replaced by 2-thienyl or 3-thienyl group[g]

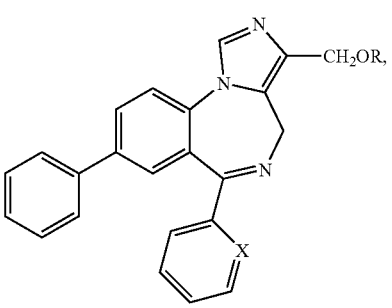

93a, x = CH, R = Me (10j)
93b, x = CF, R = Me
93c, x = N, R = Me
93d, x = CCl, R = Me
94a, x = CH, R = CH$_2$CH$_3$
94b, x = CF, R = CH$_2$CH$_3$
94c, x = N, R = CH$_2$CH$_3$
94d, x = CCl, R = CH$_2$CH$_3$

-continued

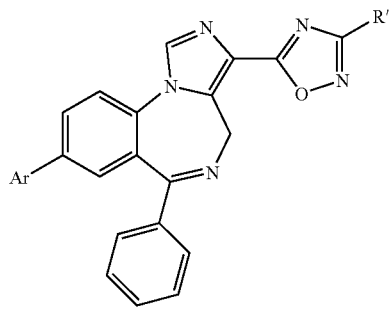

6a Ar = phenyl
R' = methyl, ethyl, isopropyl
6b Ar = 2 or 3 - thienyl
R' = methyl, ethyl, isoproply, wherein thienyl =

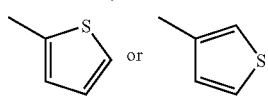

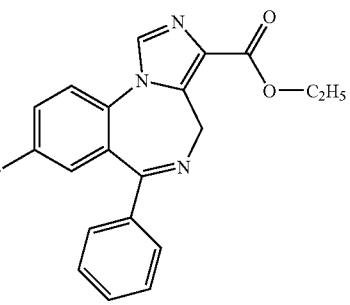

4 Ar = 2 - thienyl
or 3-thienyl wherein thienyl is

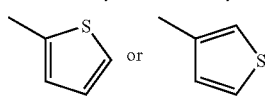

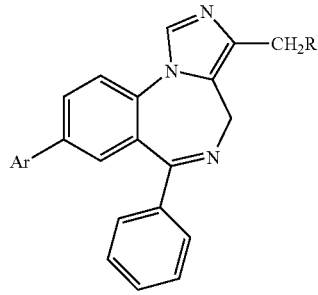

5a Ar = phenyl
R = Cl or OMe or OEt
5b Ar = 2 or 3 - thienyl
R = Cl or OMe or OEt -continued

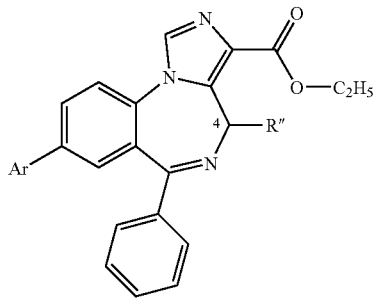

7 Ar = phenyl, 2-thienyl, or 3-thienyl
R" = (R) or (S) $CH_3$, OH, OAc, $NO_2$, $OCON(CH_3)_2$, $COOCH_3$, $COOCH_2CH_3$

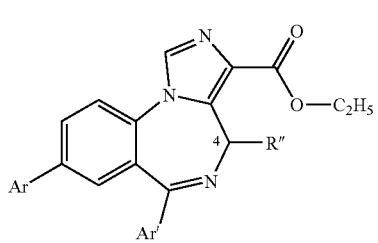

8 Ar = phenyl or 2-thienyl or 3-thienyl
Ar' = 2-thienyl or 3-thienyl, or 2'-chlorophenyl, or 2'-fluorophenyl, or 2'-nitrophenyl or 2'-pyridyl.
R" = (R) or (S) $CH_3$, OH, OAc, $NO_2$, $OCON(CH_3)_2$, $COOCH_3$, $COOCH_2CH_3$

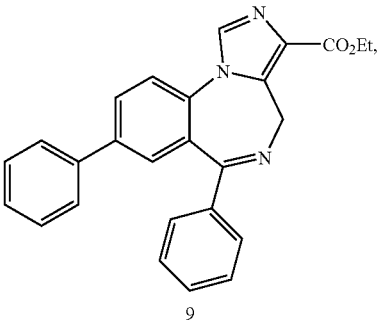

9

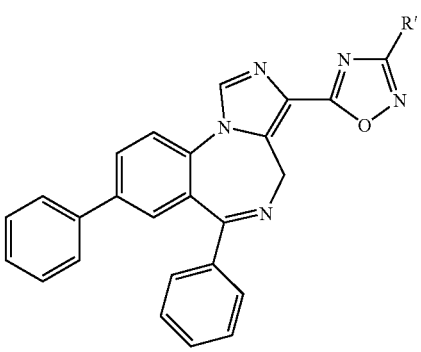

202a, R' = $CH_3$
202b, R' = $CH_2CH_3$
202c, R' = isopropyl

-continued

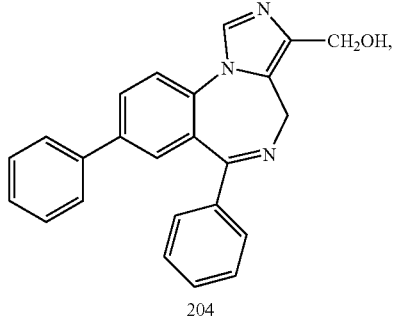

204

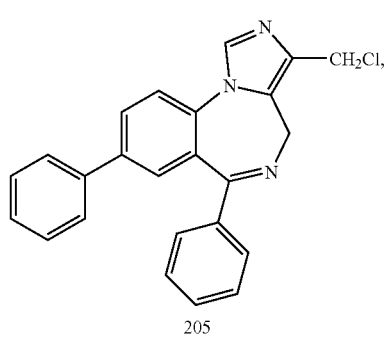

205

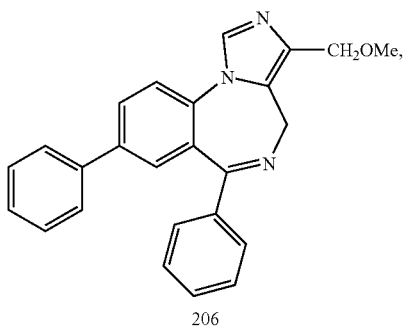

206

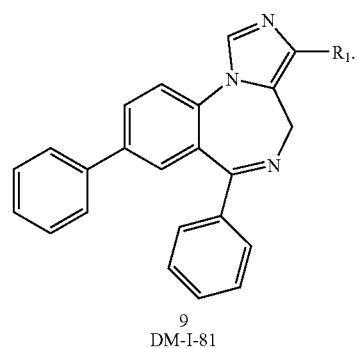

9
DM-I-81

In this embodiment, the compound, salt or prodrug selectively binds to $\alpha_5\beta_2\gamma_2$ or $\alpha_5\beta_3\gamma_2$ receptors.

In yet another preferred embodiment, the present invention provides a compound of Formula II, a salt or a prodrug thereof:

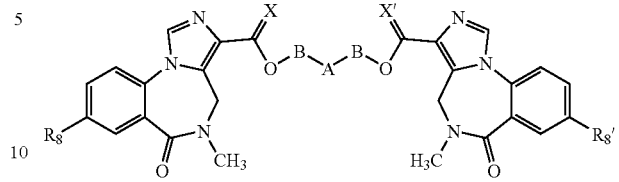

II wherein:

$R_8$ or $R_8'$ is independently selected from $C_2H_5$, $C_6H_5$, Br, —C≡C—R, —C≡C—C≡C—R; where R is H, Si$(CH_3)_3$, t-butyl, isopropyl, methyl, or cyclopropyl;

X or X' is independently selected from $H_2$ or O;

B-A-B is —$CH_2$—$(CH_2)_n$—$CH_2$— or

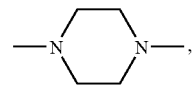

wherein n is an integer 1, 2 or 3.

In yet another embodiment, the present invention provides a compound of Formula III, a salt or a prodrug thereof,

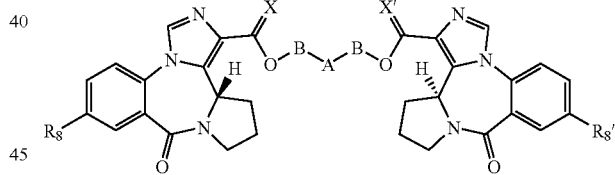

III wherein $R_8$ or $R_8'$ is independently selected from $C_2H_5$, $C_6H_5$, Br, —C≡C—R, —C≡C—C≡C—R, where R is H, Si$(CH_3)_3$, t-butyl, isopropyl, methyl, or cyclopropyl;

X or X' is independently selected from $H_2$ or O;

B-A-B is —$CH_2$—$(CH_2)_n$—$CH_2$— or

wherein n is an integer 1, 2 or 3.

In a preferred exemplary embodiment, the compounds of Formula II or III are depicted as below:

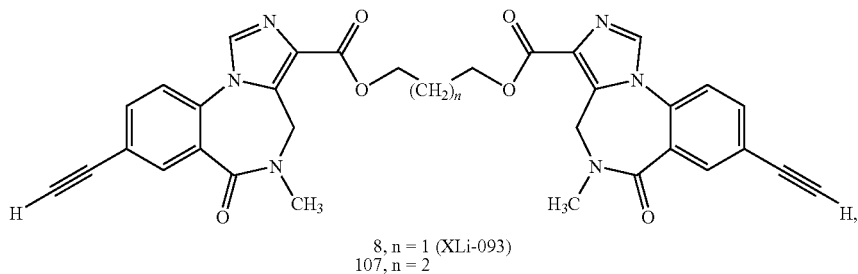
8, n = 1 (XLi-093)
107, n = 2
108, n = 3
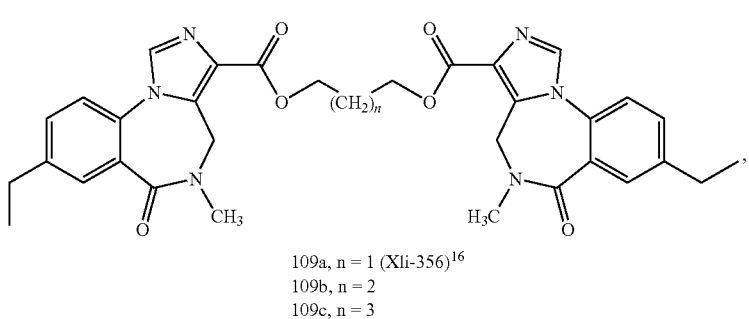
109a, n = 1 (XLi-356)[16]
109b, n = 2
109c, n = 3
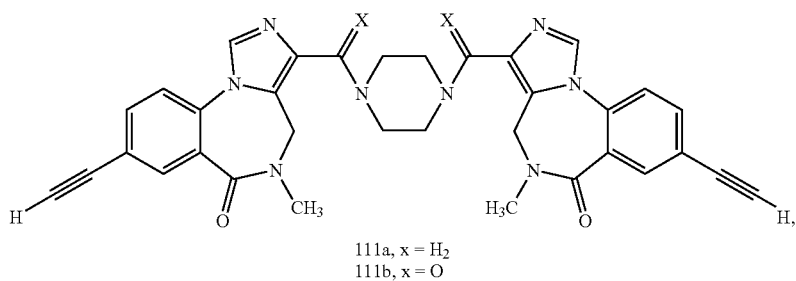
111a, x = H$_2$
111b, x = O
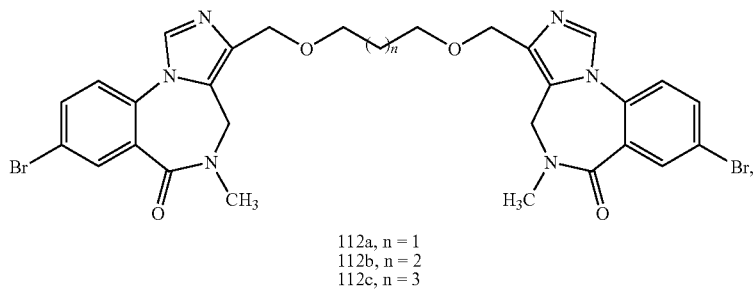
112a, n = 1
112b, n = 2
112c, n = 3
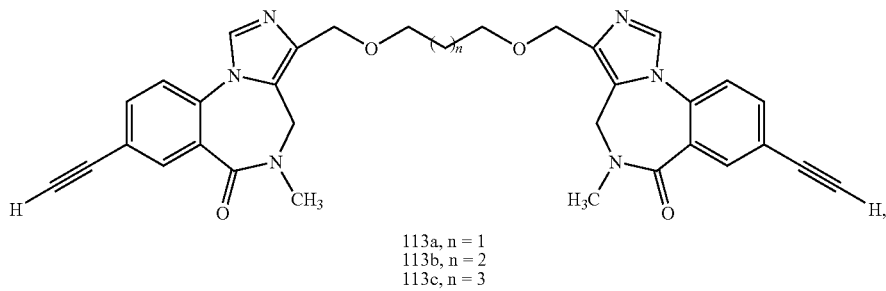
113a, n = 1
113b, n = 2
113c, n = 3

-continued

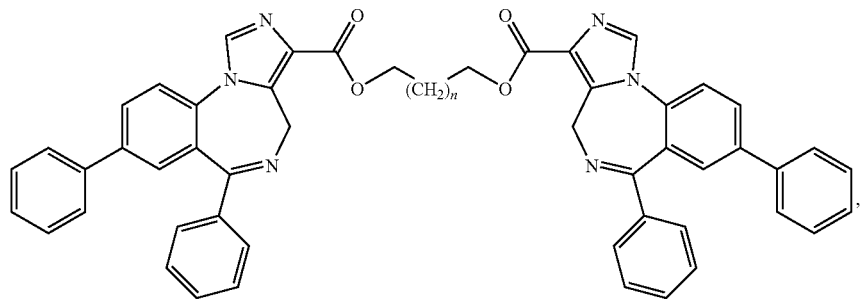

115a, n = 1
115b, n = 2
115c, n = 3

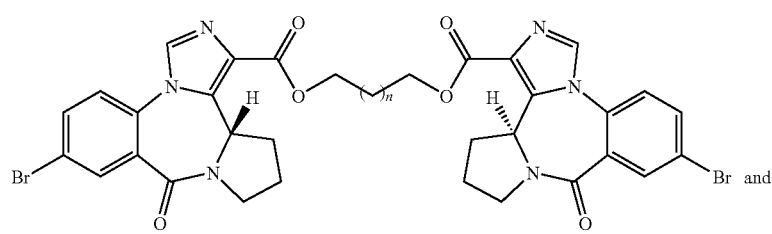

Br and

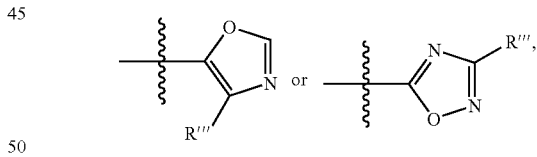

132a, n = 1
132b, n = 2
132c, n = 3

In this embodiment, the compounds, salts or prodrugs of Formula II or III selectively binds to $\alpha_5\beta_2\gamma_2$ or $\alpha_5\beta_3\gamma_2$ receptors.

A compound of Formula V, or a salt thereof,

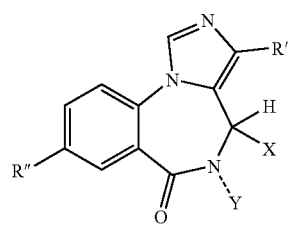

V wherein R' is branched or straight chain C1 to C4 alkyl or a methyl cyclopropyl, OMe, OEt, COOMe, COOEt, COO-i-Pr, COO-t-Bu, CH$_2$R$_1$, wherein R$_1$ is OH, Cl, OMe, OEt N(Et)$_2$, N(iPr)$_2$,

[oxazole or oxadiazole substituent structures]

wherein R''' is H or branched or straight chain C1 to C4 alkyl or a methyl cyclopropyl, —CH$_2$—OMe, —CH$_2$—OEt, —CH$_2$—O-iPr, —CH$_2$—O-tBu, —COMe, —COEt, —COPr, —COBu, —CO-iPr, —CO-t-Bu;

R'' is F, Cl, Br, NO$_2$, Et, —C≡C—R$_2$, —C≡C—C≡C—R$_2$, where R$_2$ is H, Si (CH$_3$)$_3$, t-butyl, isopropyl, methyl, or cyclopropyl, X and Y form a 4 membered or 5 membered carbocyclic ring or 4 membered or 5 membered heterocyclic ring, wherein the heteroatom is selected from O, N, or S.

In this embodiment, the compounds, salts or prodrugs of Formula V selectively binds to $\alpha_5\beta_2\gamma_2$ or $\alpha_5\beta_3\gamma_2$ receptors.

In a preferred exemplary embodiment, the compounds of Formula V are depicted as below:

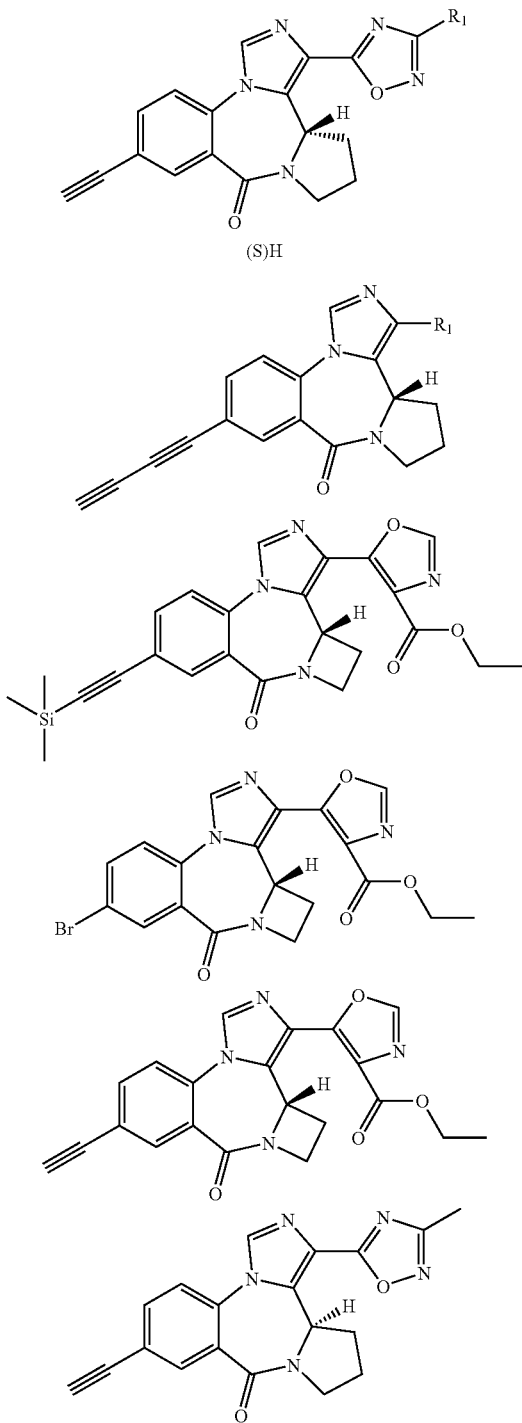

In another embodiment, the present invention also provides the use of a compound, salt or prodrug of Formula I, II, III, IV or V for the production of a pharmaceutical composition for the treatment of memory deficient and/or enhancement of memory.

In this exemplary embodiment, the pharmaceutical composition having the compound, salt or prodrug of Formula I, II, III, IV or V is used to selectively bind to $\alpha_5\beta_2\gamma_2$ or $\alpha_5\beta_3\gamma_2$ receptors.

Another embodiment of the present invention provides a method for prevention and/or treatment of memory deficit related conditions in a subject in risk thereof. This method comprises the step of administering to said subject an effective amount of a compound of Formula I, II, III, IV or V, a pharmaceutically acceptable salt, or a prodrug thereof. Also, in this embodiment, the compound, salt or prodrug selectively binds to $\alpha_5\beta_2\gamma_2$ or $\alpha_5\beta_3\gamma_2$ receptors. In another preferable embodiment, the subject is administered an effective amount of a compound of Formula I, II, III, IV or V and a pharmaceutically acceptable salt, or a prodrug thereof, in combination with $Zn^{2+}$ ions. $Zn^{2+}$ ions appear to enhance the selective binding of certain compounds of the invention to the $\alpha_5\beta_2\gamma_2$ or $\alpha_5\beta_3\gamma_2$ receptors.

Another embodiment of the present invention provides a pharmaceutical composition. The composition comprises: (a) a compound of Formula I, II, III, IV or V; or (b) a pharmaceutically acceptable salt of said compound; or (c) a pharmaceutically acceptable prodrug of said compound; and (d) a pharmaceutically-acceptable carrier. In this embodiment, the compound, salt or prodrug selectively binds to $\alpha_5\beta_2\gamma_2$ or $\alpha_5\beta_3\gamma_2$ receptors.

Other objects and advantages of the present invention will be apparent from the detailed description, drawings and claims accompanying the specification.

DESCRIPTION OF THE DRAWINGS

FIG. 1 schematically depicts the synthesis of XLi-093 (8), as well as the synthesis of additional α5 subtype selective ligands based on XLi-093 (8).

FIG. 5 depicts the synthesis of DM-I-81 and its analogs.

FIG. 6 provides data on cognition enhancement by Xli-093. The figure depicts effects of compound XLi-093 on the mean delay achieved by C57BL/6J mice titrating delayed matching to position schedule.

FIG. 7 depicts DM-I-81 aligned in the included volume of the pharmacophore/receptor model for the α1β3γ2 and α5β3γ2 subtypes.

FIG. 8 depicts screening of Xli-356 and RY80 compounds in stably expressed HEK cells

In FIG. 10 it appears that the compound PWZ-29 at 10 mg is able to reverse the effects of scopolamine quite effectively. The vehicle used was 0.9% saline with 2.5% encapsin.

FIGS. 11 (A), (B) and (C) depicts modulation of EC3 in oocytes currents by PWZ compounds. Compounds PWZ-29, PWZ-31A and PWZ-35A were chosen based on their binding and electrophysiology data. Xli356 appears to be an agonist at alpha5 based on in vitro electrophysiology data. However activity of Xli356 may be based on the possibility that the compound is both an inverse agonist and an agonist that enhances memory deficit due to the complex nature of how synaptic and extrasynaptic receptors counter balance each other, as suggested by Mohler.

DETAILED DESCRIPTION OF THE PREFERRED EMBODIMENTS

I. General

Figure 2:
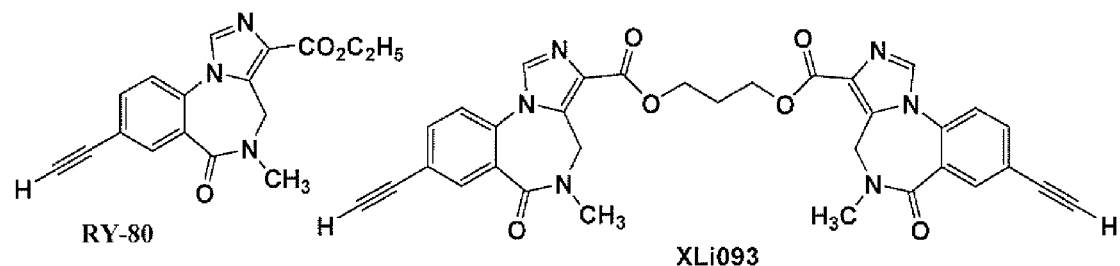
FIG. 2 depicts the binding affinity of XLi-093 (8) in vitro as determined on α1-6β3γ2 LTK cells.

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

As defined herein, "contacting" means that the compound used in the present invention is introduced into a sample containing the receptor in a test tube, flask, tissue culture, chip, array, plate, microplate, capillary, or the like, and incubated at a temperature and time sufficient to permit binding of the compound to a receptor. Methods for contacting the samples with the compound or other specific binding components are known to those skilled in the art and may be selected depending on the type of assay protocol to be run. Incubation methods are also standard and are known to those skilled in the art.

In another embodiment, the term "contacting" means that the compound used in the present invention is introduced into a subject receiving treatment, and the compound is allowed to come in contact in vivo.

As used herein, the term "treating" includes preventative as well as disorder remittent treatment. As used herein, the terms "reducing", "suppressing" and "inhibiting" have their commonly understood meaning of lessening or decreasing.

In certain embodiments, the present invention encompasses administering the compounds useful in the present invention to a patient or subject. A "patient" or "subject", used equivalently herein, refers to an animal. In particular, an animal refers to a mammal, preferably a human. The subject either: (1) has a condition remediable or treatable by administration of a compound of the invention; or (2) is susceptible to a condition that is preventable by administering a compound of this invention.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

II. Preferred Embodiments

Certain compounds used in the present invention are described below:

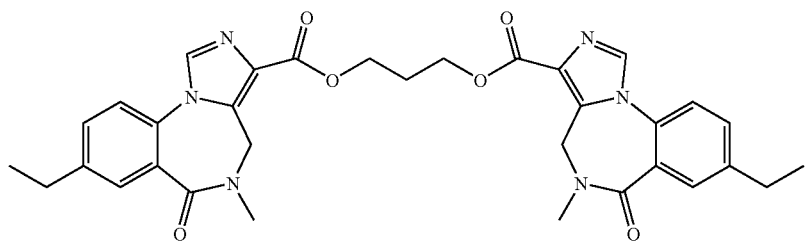

1                                                                                          XLI356

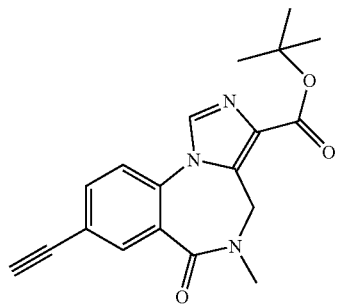

2                                                                                          RY024

-continued
| | | |
|---|---|---|
| 3 | 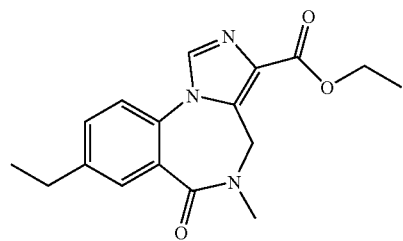 | RY10 |
| 4 | 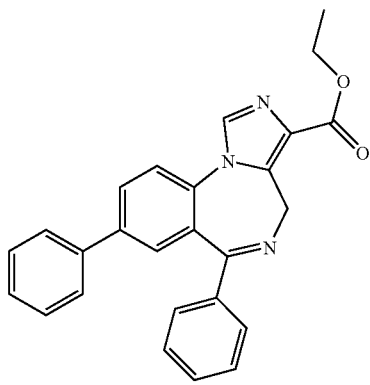 | DM-I-81 |
| 5 | 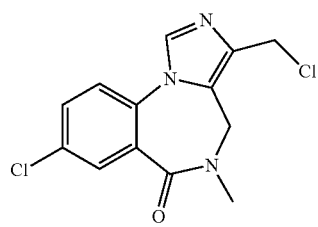 | PWZ-031A |
| 6 | 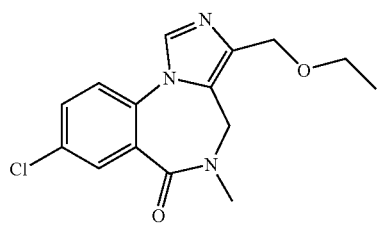 | PWZ-035A |
| 7 | 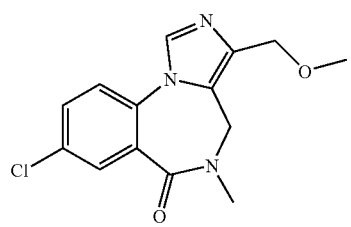 | PWZ-029 |
| 8 | 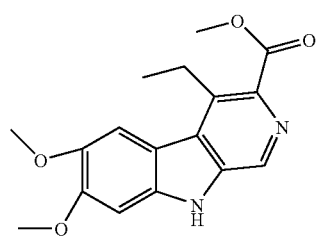 | DMCM |

9 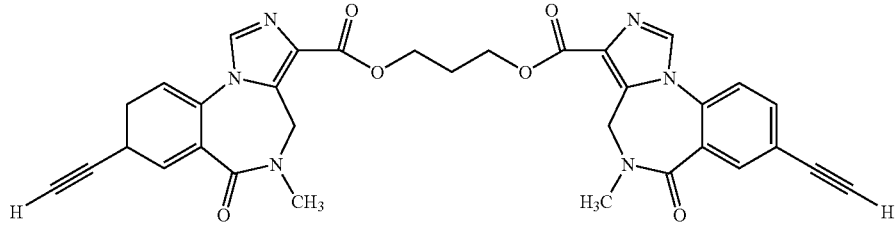 XLI-093

10 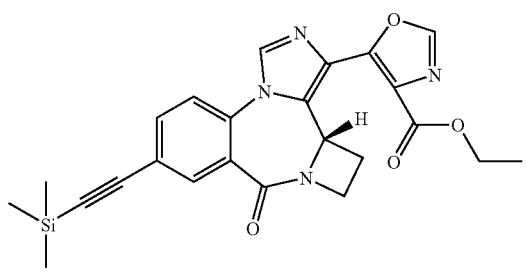 RY-068

11 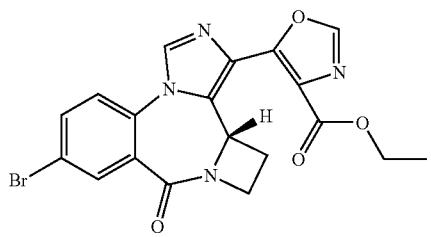 RY-062

12 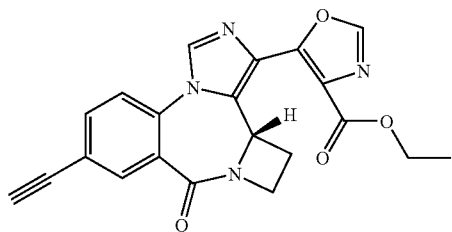 RY-069

13 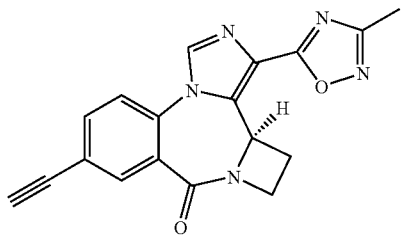 RY-I-29

The present invention centers on the design (molecular modeling) and synthesis of α5β3γ2 selective agonists, antagonists or inverse agonists to treat dementia, including age associated memory impairment and Alzheimer's disease. Since α5β3γ2 BzR/GABA(A) receptor subtypes are located almost exclusively in the hippocampus, a substrate intimately involved in memory and learning, it is possible to enhance cognition without the sedative-hypnotic, muscle-relaxant or ataxic side effects of classical benzodiazepines.

Several recent discoveries bear on this approach. First of all, in Alzheimer's disease GABAergic neurons are fully functional until the very late stages of the disease, even though cholinergic neurons are depleted throughout the disease. Other dementias are similar in etiology. Second, it was recently shown in experiments (in α5 "knockin" mice) that α5β3γ2 BzR/GABAergic subtypes do affect memory and learning (Möhler et al. 2004). In brief, this group has provided strong evidence that hippocampal extrasynaptic α5 GABA (A) receptors play a critical role in associative learning as mentioned above. This was earlier reported by the Merck group, using α5 inverse agonists, as well as by the inventors. Third, since many α5β3γ2 BzR/GABAergic receptors are located extrasynaptically (nonsynaptically), α5β3γ2 BzR/GABA(A) agonists may well enhance memory in both age associated dementia and Alzheimer's disease without the limitations experienced by cholinergic agents. The development of a 8-phenyl α5 selective ligand was based on this approach.

Support for this approach was also derived from the following lines of reasoning: 1) While most neurotransmitter systems are degenerating in the SDAT brain, the GABAergic infrastructure is relatively well preserved (Meyer et al. 1995; Mizukami et al. 1997; Lowe et al. 1988; Nagga et al. 1999); 2) Numerous cognitive deficit models of cholinergic hypofunction, both human and animal, benefit cognitively when GABA activity is reduced (Flood et al. 1996; DeLorey et al. 2001); 3) Beneficial effects of BzR inverse agonists can also be generalized to the aged nervous system, as indicated by their ability to improve working memory performance in memory impaired aged rats (Forster et al., 1995); 4) Lesion studies demonstrate that animals with 50-70% loss of cortical cholinergic fibers exhibit improved cognitive performance from BzR treatment (Sarter and Bruno 1997).

As the loss of cholinergic neurons in age associated memory impairment and SDAT is commonly in the 40-70% range (Flood et al. 1996; Nagga et al. 1999) until the very last stage, the effects of BzR inverse agonists on restoring neural transmission in animals with a partial loss of cortical cholinergic inputs suggests development of specific BzR inverse agonist for the treatment of cognitive decline associated with aging and SDAT is also warranted.

Although α5 selective inverse agonists earlier described by the inventors (Bailey et al. 2002; DeLorey et al. 2001) and used by others (Chambers et al. 2002, 2003) have been shown to enhance cognition, recently the inventors developed an α5 subtype selective antagonist which clearly enhances cognition (Yin et al. 2004). It has no efficacy at α1-α6 subtypes; however, this agent was found to bind to the α5 subtype at 15 nM and antagonized potently the percent modulation of GABA by diazepam in oocytes (Li et al. 2003). The agent was then shown to enhance cognition on the mean delay achieved by C57BL/6J mice under the titrating delayed matching-to-position schedule (Li et al. 2003; Zhang 2004; Li 2004). An antagonist at BzR sites would be expected to exhibit no sedative effect, no convulsive, nor any proconvulsive side effects (Crestani et al. 2002; Möhler et al. 2004).

The alpha 5 selectivity of the lead ligands XLi093 and XLi356 were designed by molecular modeling. These agents or their analogs enhance cognition without the side effects of classical benzodiazepines. The agents do not effect convulsions, a side effect of inverse agonists. Moreover, these agents will remain effective even though cholinergic neurons are being depleted, up until the very last stages of the disease when all the neurons undergo aptosis.

Previously, the inventors designed a series of α5 subtype selective ligands [(RY-023), (RY-024), (RY-079) and (RY-080)] based on the structure of Ro 15-4513 (Skolnick et al. 1997; Liu et al. 1995, 1996, 1997). Other related ligands were described by McKernan, Atack, and coworkers (Chambers et al. 2002, 2003; Sur et al. 1998). These ligands are BzR inverse agonists in vivo and a number of them have been shown to enhance cognition (Chambers et al. 2002, 2003; Bailey et al. 2002; DeLorey et al. 2001; Sur et al. 1998). One of these ligands was shown to be important in the acquisition of fear conditioning and has provided further evidence for the involvement of hippocampal GABA(A)/BzR in learning and anxiety (Bailey et al. 2002). This is in agreement with the work of DeLorey et. al. (2001) in a memory model with a ligand closely related to α5 subtype selective inverse agonists RY-024 and RY-079.

To enhance the subtype selectivity, the bivalent form of RY-080 was synthesized to provide XLi-093 (8) (Li et al. 2003). FIG. 1 shows the synthesis of XLi-093 (8), as well as the synthesis of additional α5 subtype selective ligands based on XLi-093 (8).

The binding affinity of XLi093 (8) in vitro was determined on α1-6β3γ2 LTK cells and is illustrated in the Scheme as shown in FIG. 2

This bivalent XLi-093 (8) ligand bound to α5β3γ2 subtypes with a Ki of 15 nM, but exhibited little or no affinity at other BzR/GABA(A) subtypes (Li et al. 2003). Since receptor binding studies indicated bivalent ligand XLi-093 bound almost exclusively to the α5 subtype, the effect of this ligand on various GABA(A) receptors expressed in Xenopus oocytes was investigated (Li et. al. 2003). Analysis of the data indicated that up to a concentration of 1 nM, XLi-093 (8) did not trigger chloride currents in any one of the GABA(A) subtypes tested. At 1 uM 8 did not modulate GABA induced chloride flux in α1β3γ2, α2β3γ2, or α3β3γ2 receptors, but very slightly inhibited currents in α5β3γ2. At 1 μM, 8 only marginally influenced diazepam stimulation of GABA-induced current in α1β3γ2, α2β3γ2 and α3β3γ2 BzR, but shifted the diazepam dose response curve to the right in α5β3γ2 receptors in a significant fashion (Li et al. 2003). Importantly, bivalent ligand 8 was able to dose dependently and completely inhibit diazepam-stimulated currents in α5β3γ2 receptors.

Figure 3:
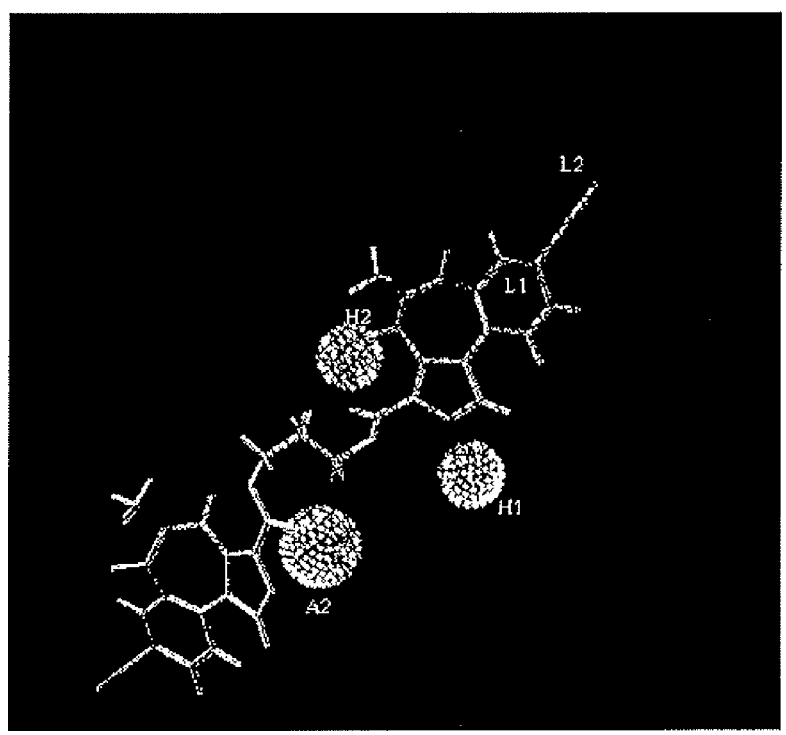
FIG. 3 depicts compound 8 aligned in the pharmacophore-receptor model of the α5β3γ2 subtype.

FIG. 3 depicts compound 8 aligned in the pharmacophore-receptor model of the α5β3γ2 subtype. The fit is excellent (Li et al. 2003; Zhang. 2004). This indicates that bivalent ligands will bind to BzR subtypes. In an even more exciting development, Yin et al. (2004) have reported data that the α5 subtype selective antagonist 8 does indeed enhance performance under a titrating delayed matching to position schedule of cognition in C57BL/6J mice (Yin et al. 2004), as shown in FIG. 6. This compound 8 does cross the blood brain barrier (Yin et al. 2004).

To date, in regard to bivalent ligands, the preferred linkers between the two pharmacophores (see 8) have been established as 3 methylene units, 4 methylene units or 5 methylene units. This has been established by low temperature NMR experiments, molecular modeling and X-ray crystallography of the ligands in question and has been reported (Zhang 2004; Li 2004; Han et al. 2004; Yin et al. 2004). Recently a number of more selective ligands for α5β3γ2 subtypes have been synthesized (see Table 1). Although the basic imidazobenzodiazepine scaffold has been maintained (Zhang 2004; Li 2004), substituents were varied in regions A, B and C, based on our previous molecular modeling (Huang et al. 2000; Li et al. 2003; Liu et al. 1996). The substituents in regions A, B and C, which provided the α5 subtype selectivity, are all different. Despite this, these are the most α5 subtype selective ligands ever reported (Zhang 2004; Li 2004; Han et al, 2004; Yin et al. 2004).

One can mix and match the substituents in these ligands to obtain α5 subtype selective agents with 400 fold selectivity for α5 subtypes over the other 5 subtypes. This is the key to unlocking the true, unequivocal physiological responses mediated by α5 subtypes in regard to cognition, (amnesia), anxiety and convulsions, all of which to some degree may be influenced by α5 subtypes. In most cases, as shown in the ligands in Table 1 and Table 2, affinity occurs only at α5β3γ2 subtypes. In addition, since bivalent ligand 8 bound very tightly only to α5 BzR subtypes, the functionality present in region A can now be incorporated into other bivalent ligands.

TABLE I

Affinities of potent α5 subtype selective ligands for αxβ3γ2 (α = 1-6) benzodiazepine receptor GABA(A) isoforms.

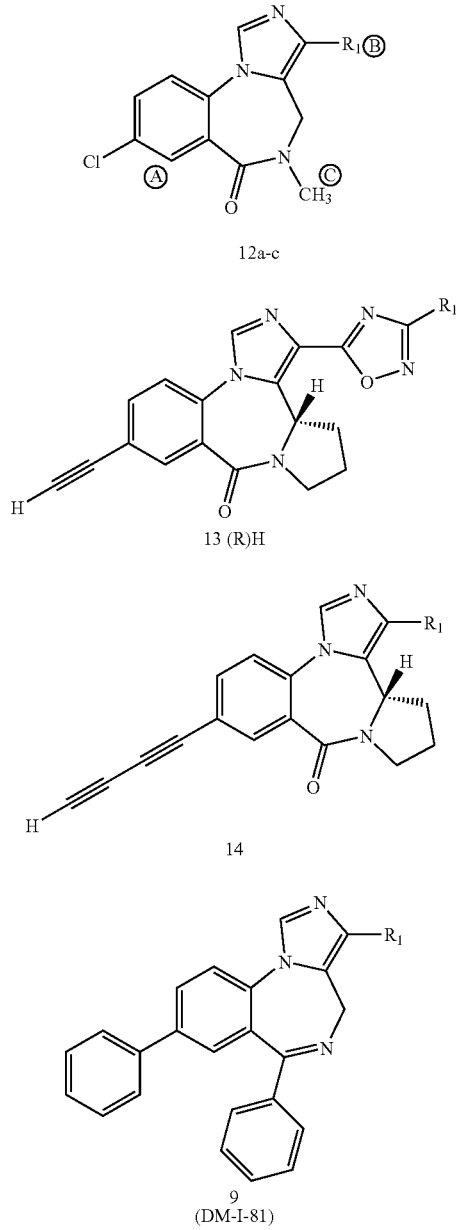

12a-c 13 (R)H

14

9
(DM-I-81)

| Li-gand | R₁ | α1 | α2 | α3 | α4 | α5 | α6 |
|---|---|---|---|---|---|---|---|
| | | | | $K_i$ (nM)$^a$ | | | |
| 12a | CH₂OCH₃ | >300 | >300 | >300 | ND | 38.8 | >300 |
| 12b | CH₂Cl | >300 | >300 | >300 | ND | 28.5 | >300 |
| 12c | CH₂OEt | >300 | >300 | >300 | ND | 82.7 | >300 |
| 13 | CH₃ | >1000 | >1000 | >1000 | ND | 157 | >1000 |
| 14 | CO₂Et | >1000 | >1000 | >1000 | ND | 64 | >1000 |
| 9 | CO₂Et | >2000 | >2000 | >2000 | >2000 | 176 | >2000 |

$^a$Data shown here are the means of two determinations which differed by less than 10%.
ND = Not Determined (presumably similar to α6).

TABLE 2

Affinities of potent α5 subtype selective ligands for αxβ3γ2 (α = 1-6) benzodiazepine receptor GABA(A) isoforms

XL1356

RY-068

RY-062

RY-069

RY-I-29

| Ligand | α1 | α2 | α3 | α4 | α5 | α6 |
|---|---|---|---|---|---|---|
| | | | $K_i$ (nM)$^a$ | | | |
| XLi356 | 2383 | 5980 | ND | ND | 107 | 5000 |
| RY068 | >500 | 877 | 496 | ND | 37 | >1000 |
| RY062 | >1000 | >1000 | >500 | ND | 172 | >2000 |
| RY069 | 692 | 622 | 506 | ND | 19 | >1000 |
| RY-I-29 | >1000 | >1000 | >1000 | ND | 157 | >1000 |

$^a$Data shown here are the means of two determinations which differed by less than 10%
ND = Not Determined (presumably similar to α6)

From the data in FIG. 6 it is clear the α5 antagonist (8) has enhanced cognition 8 did enhance cognition in a memory model (Yin et al. 2004). Accordingly, the two acetylenic groups of XLi-093 (8) were reduced to provide ethyl functions. This provided a new bivalent ligand (XLi-356) which shows (in oocytes) no activity at α1 subtypes, but is a clear agonist at α5 subtypes, as shown in Table 2 (Li 2004). DeLorey recently showed that XLi 356 does potently reverse scoploamine induced memory deficiencies (DeLorey 2001). In addition Roth et. al. has recently determined $K_i$ values for XLi-356 (25) in HEK-T cells [α1 (no affinity); α5(107 nM)].

Figure 9:
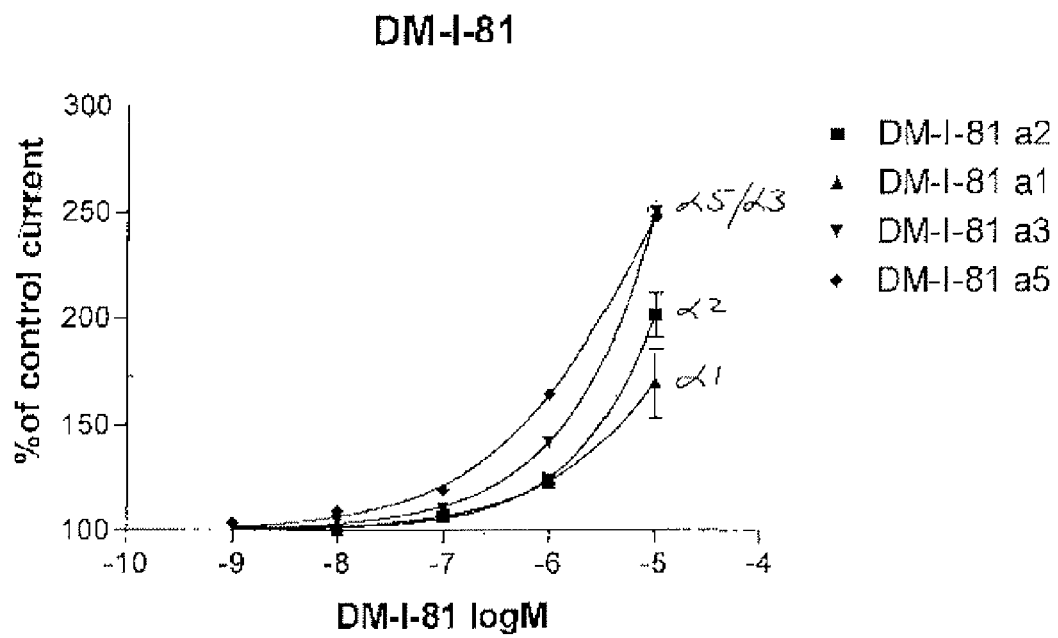
FIG. 9 depicts comparative affinity of compound DM-I-81 to various α-subtypes. Dose response curves for DM-I-81 in oocytes expressing $GABA_A$ receptor subunits α1-α5 in combination with β3 and γ3 subunits. cRNA-injected Xenupus oocytes were held at −60 mV under two-electrode voltage clamp. Increasing concentrations of DM-I-81 was superfused together with a GABA concentration eliciting app. 3% of the maximal current amplitude. Drugs were reapplied for 30 secs before the addition of GABA, which was coapplied with the drugs until a peak response was observed. Data were normalized for each curve assuming 100% for the response in the absence of DM-I-81. Drugs were made up and diluted as stock solutions in DMSO. Final concentrations of DMSO perusing the oocyte were 0.1%. Values are presented as mean of two oocytes.
Figure 10:
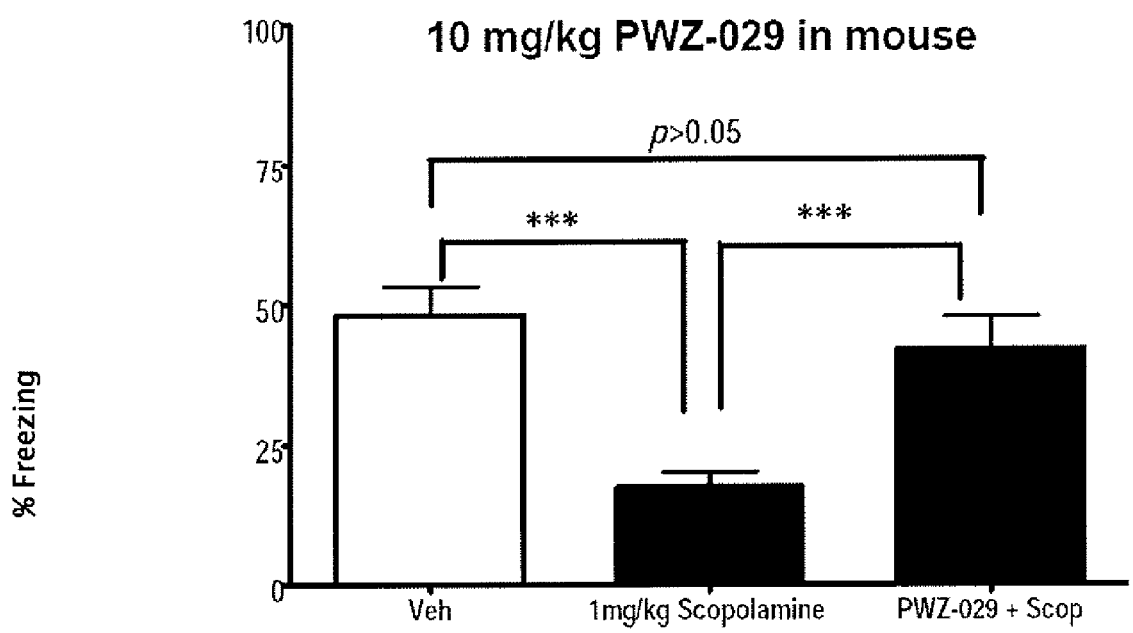
FIG. 10 depicts fear conditioned contextual memory when 10 mg/kg of PWZ-029 is injected into mouse demonstrating the attenuation of contextual memory impairment caused by 1 mg/kg scopolamine.
Figure 12A:
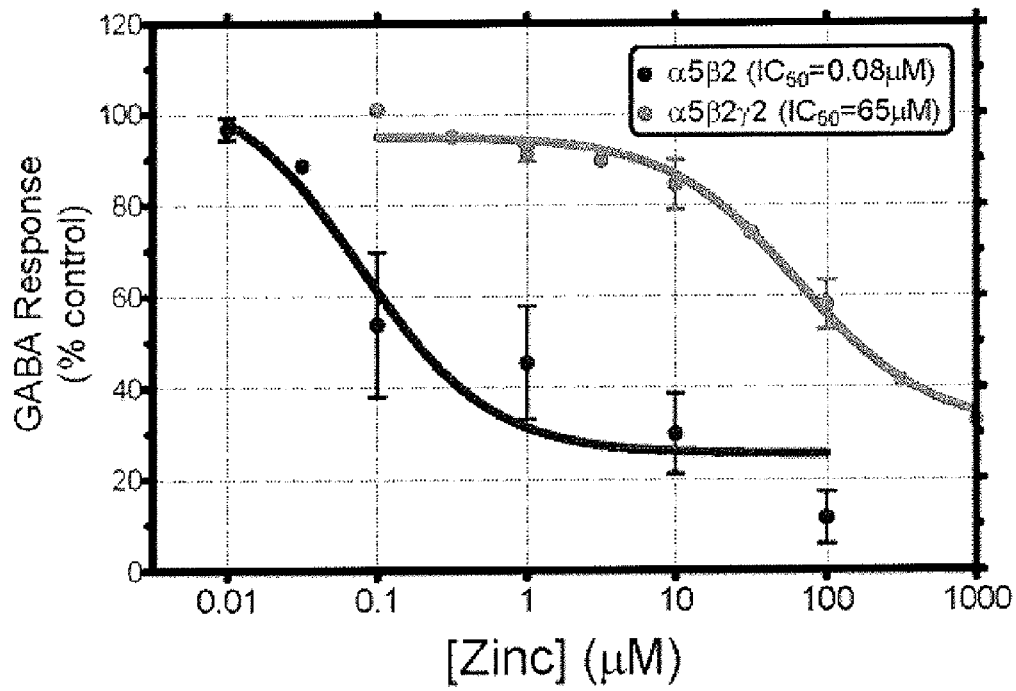
FIG. 12 (a) depicts that $Zn^{2+}$ is a potent inhibitor of $\alpha_5\beta_2$ and a weak antagonist of $\alpha_5\beta_2\gamma_2$ (b) Whiting et al. depicted that $Zn^{2+}$ is a potent inhibitor of $\alpha_1\beta_1$ and a weak antagonist of $\alpha_5\beta_2\gamma_2$s and $\alpha_1\beta_1\epsilon$.
Figure 12:
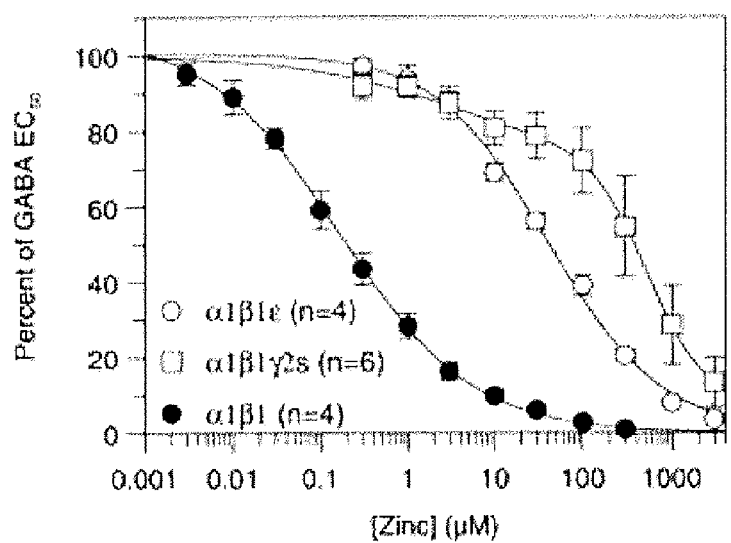
Figure 13:
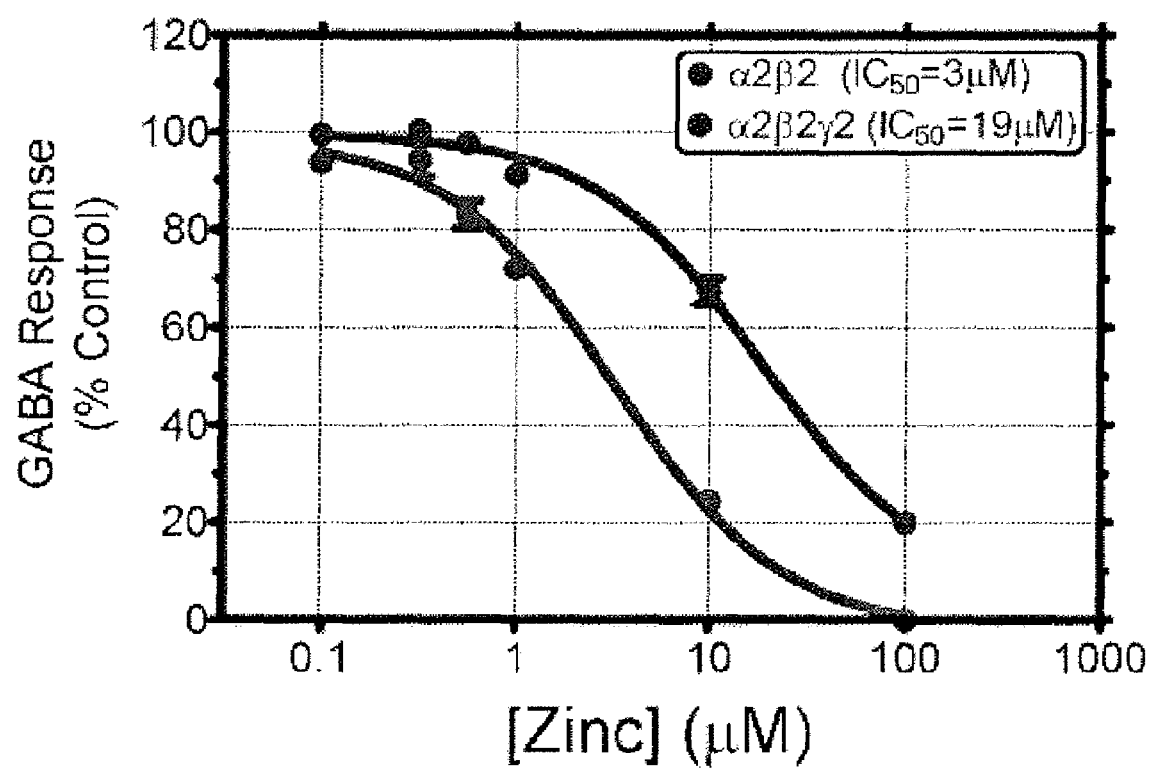
FIG. 13 depicts differential antagonist potency of $Zn^{2+}$ ions at $\alpha_2\beta_2\gamma_2$ and $\alpha_2\beta_2$ for GABA-receptors.
Figure 14:
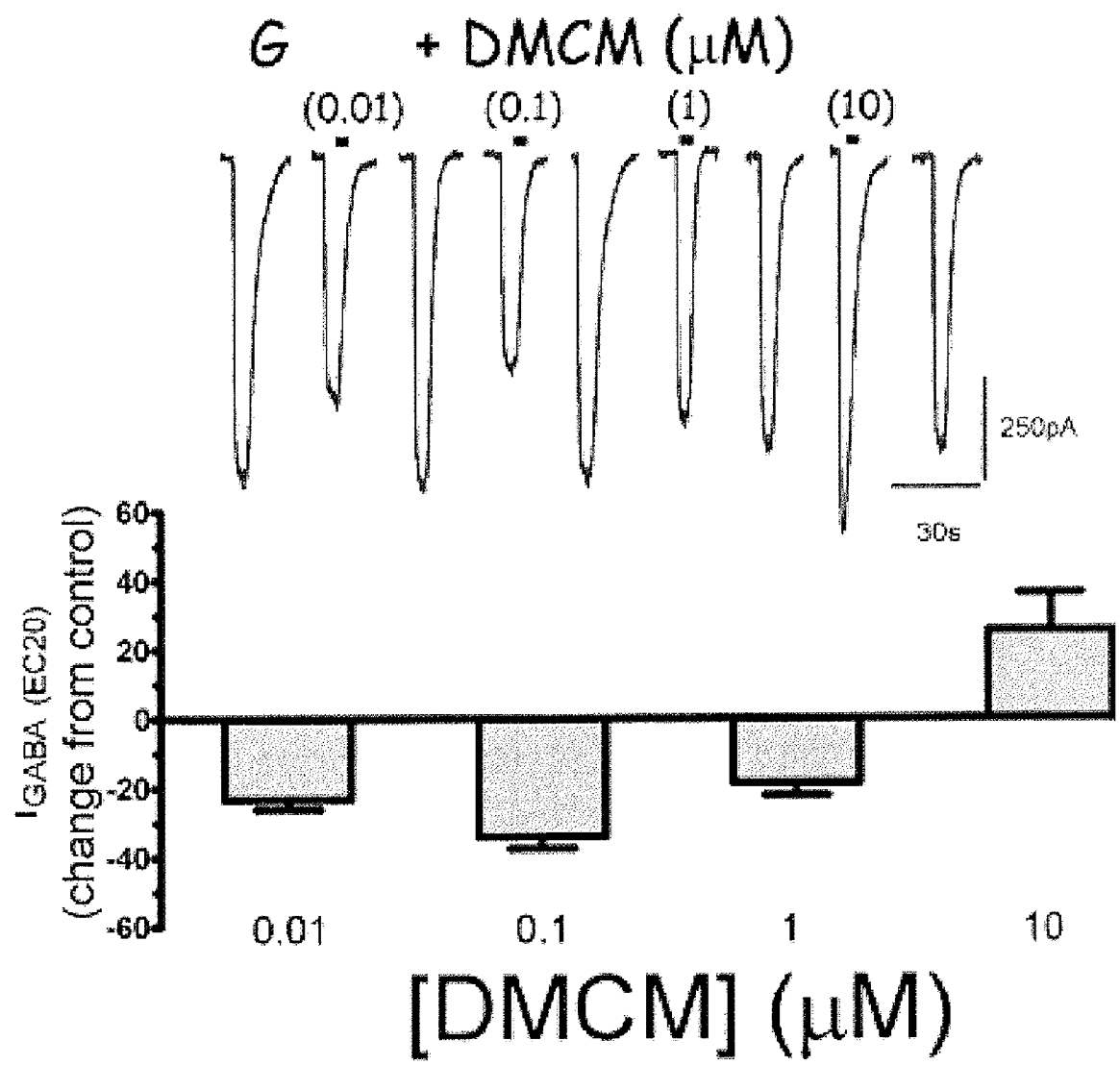
FIG. 14 depicts bidirectional modulation of $\alpha_5\beta_2\gamma_2$ mediated currents by compound DMCM.
Figure 15:
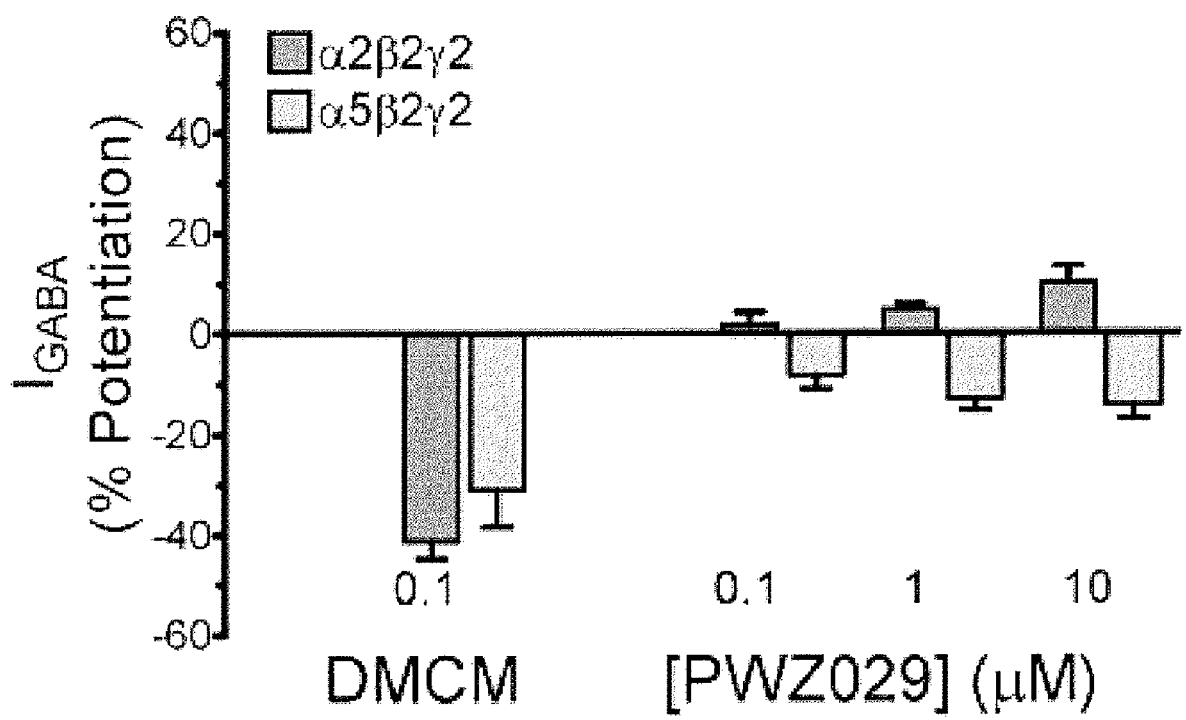
FIG. 15 depicts the effects of compound PWZ029 on $\alpha_2\beta_2\gamma_2$ and $\alpha_5\beta_2\gamma_2$ GABA receptors.
Figure 16:
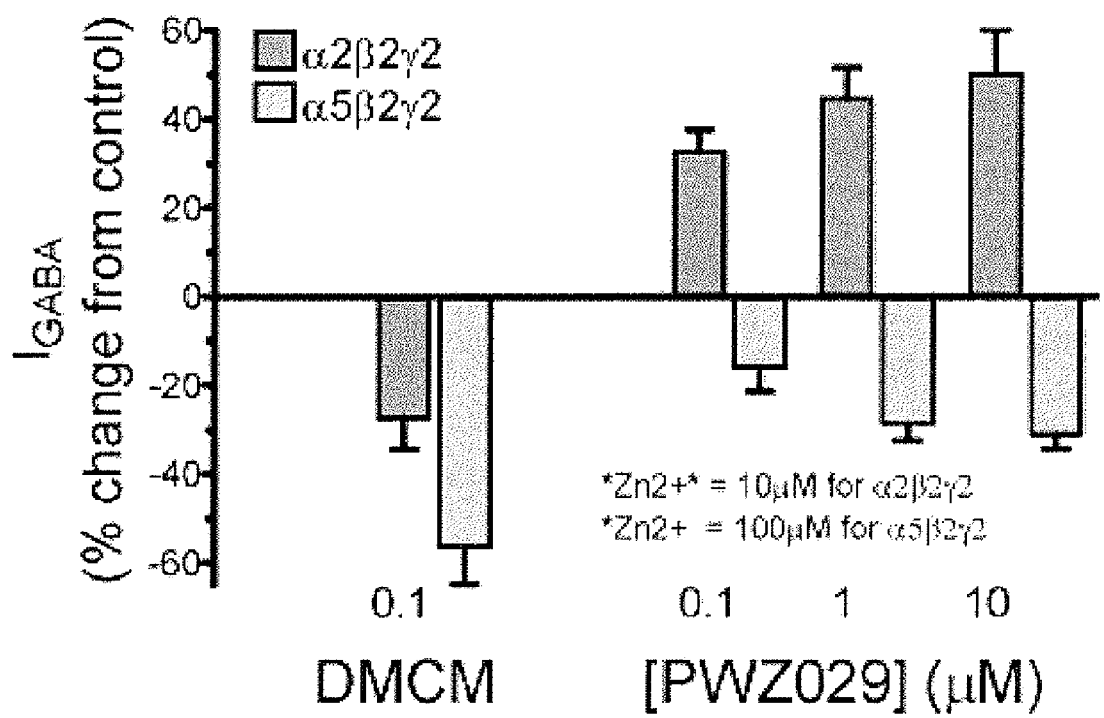
FIG. 16 depicts the effects of compound PWZ029 on $\alpha_2\beta_2\gamma_2$ and $\alpha_5\beta_2\gamma_2$ GABA receptors in the presence of $Zn^{2+}$ ions.
Figure 17:
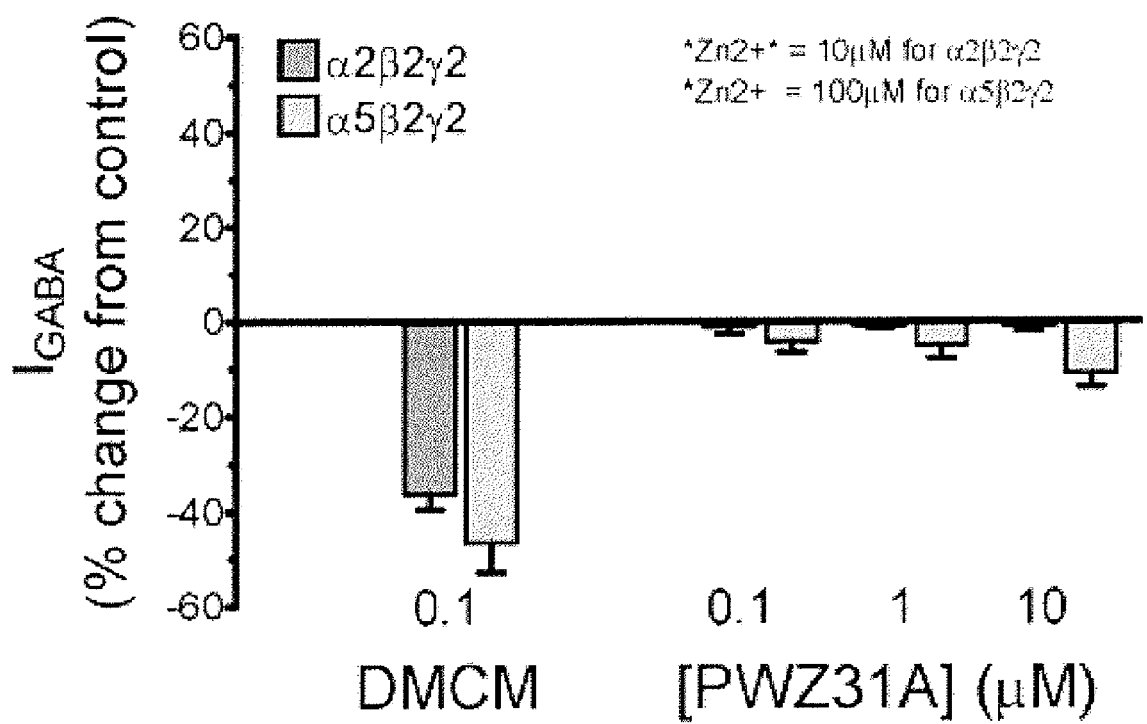
FIG. 17 depicts the effects of compound PWZ031 on $\alpha_2\beta_2\gamma_2$ and $\alpha_5\beta_2\gamma_2$ GABA receptors in the presence of $Zn^{2+}$ ions.
Figure 18:
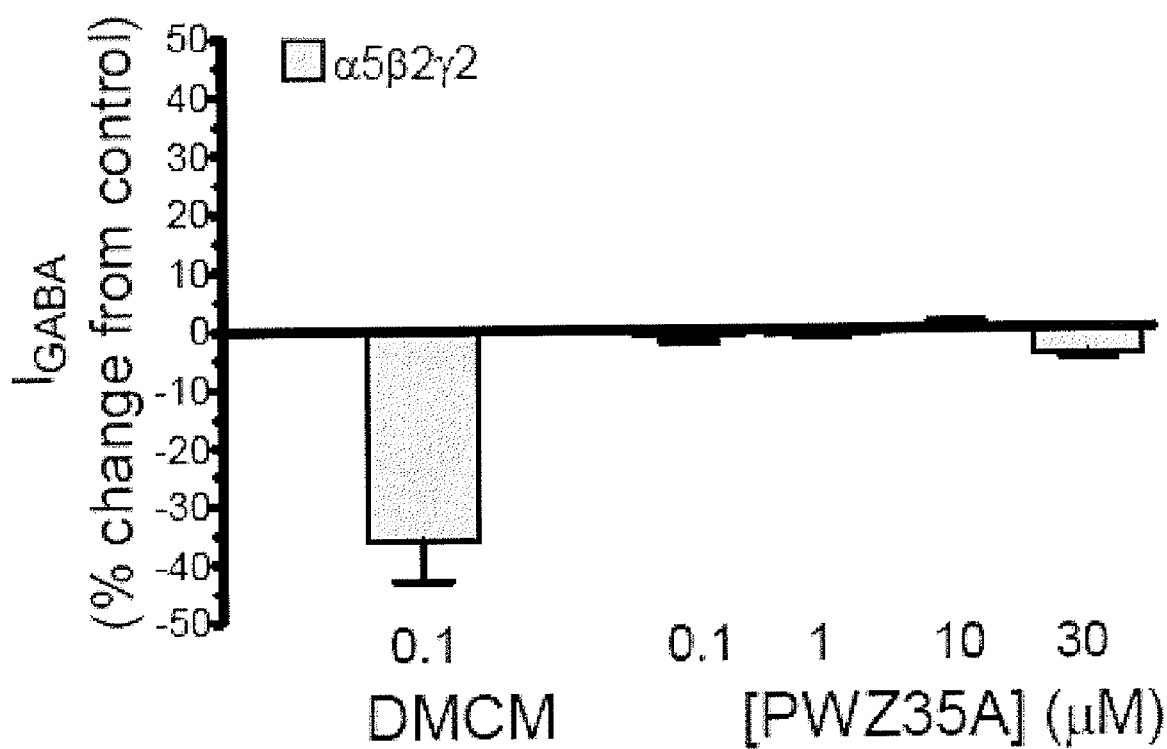
FIG. 18 depicts the effects of compound PWZ035A on $\alpha_2\beta_2\gamma_2$ and $\alpha_5\beta_2\gamma_2$ GABA receptors in the presence of $Zn^{2+}$ ions (10 µM).
Figure 19:
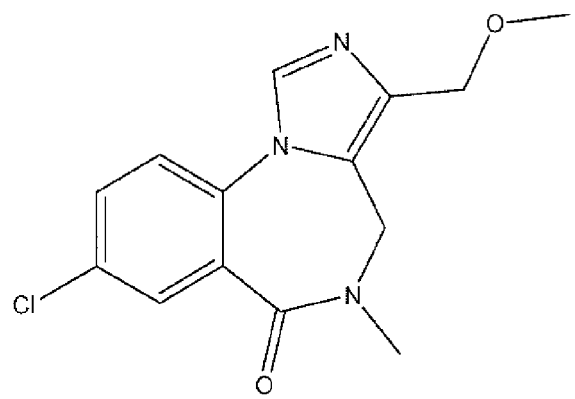
FIG. 19 depicts structure-affinity measurements for compound PWZ-029 at the α5 subtype and this compound at 300 nM for various other GABA receptors. While higher concentrations of the compound were not used, one of ordinary skill may use >1000 nM or 3000 nM. In this figure, the oocyte data indicates the PWZ compounds appear to be inactive at α1, α2, α3, with no affinity at α6, and therefore no affinity at α4, which indicates affinity at α5, indicating inverse agonist activity at α5. PWZ-029 is a selective inverse agonist at α5 with very, very weak agonist activity at α2β3γ2 receptors.
Figure 20:
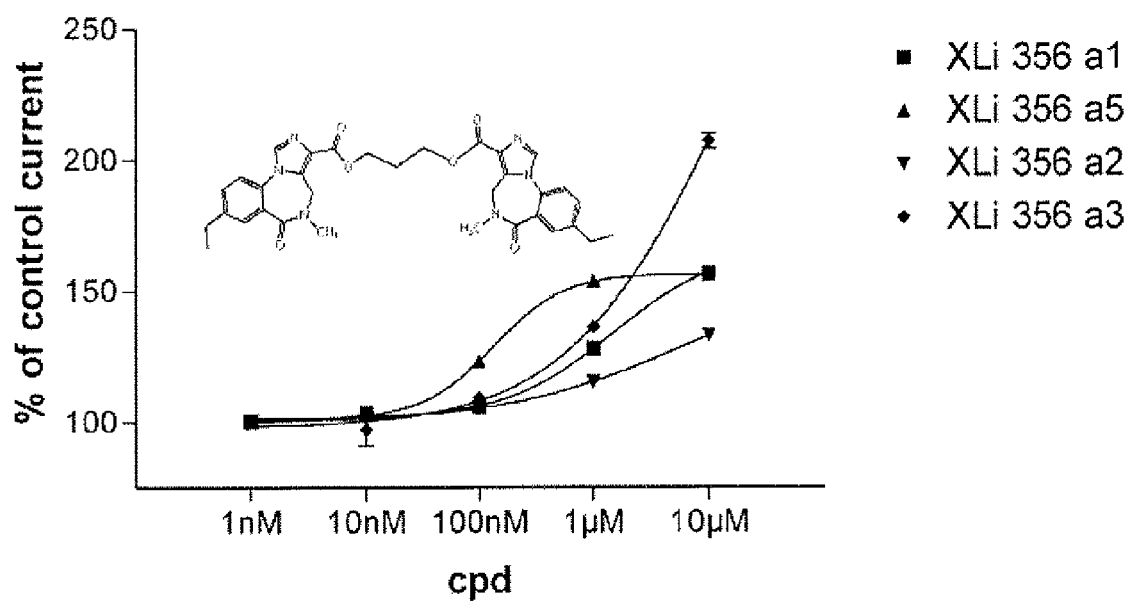
FIG. 20 depicts α5 selective ligands that enhance memory. These compounds do not bind to any other receptors.
Figure 21:
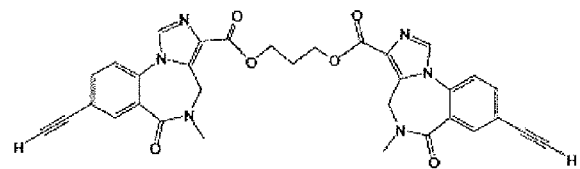
FIG. 21 depicts selectivity of compound XLI093 to various receptors. Compound XLI093 binds selectively to α5 ligands that enhances Memory.
Figure 22:
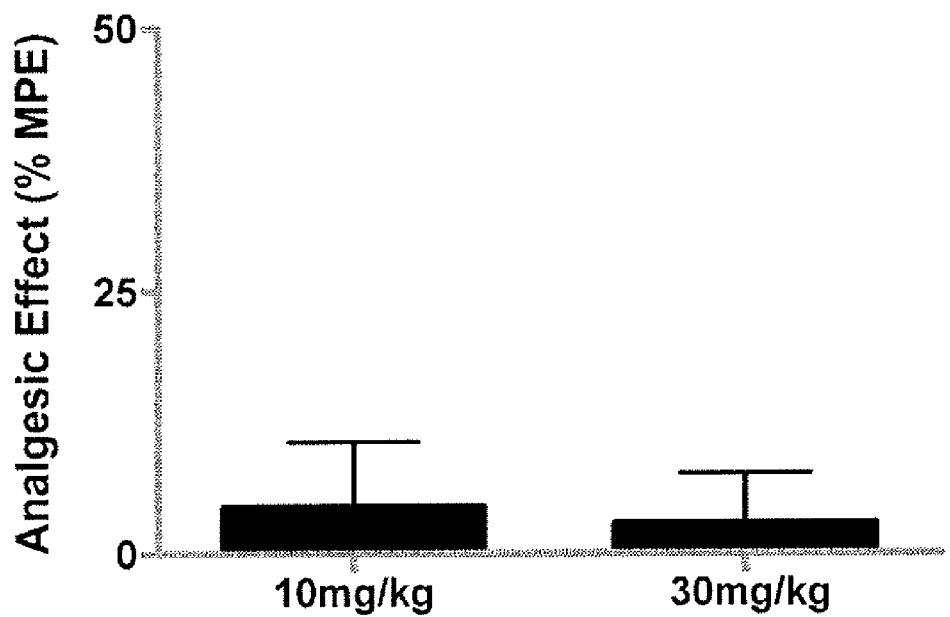
FIG. 22 depicts analgesic effect of compound XLI356. No analgesic effect caused by Xli356 in regards to tail flick assay.
Figure 23:
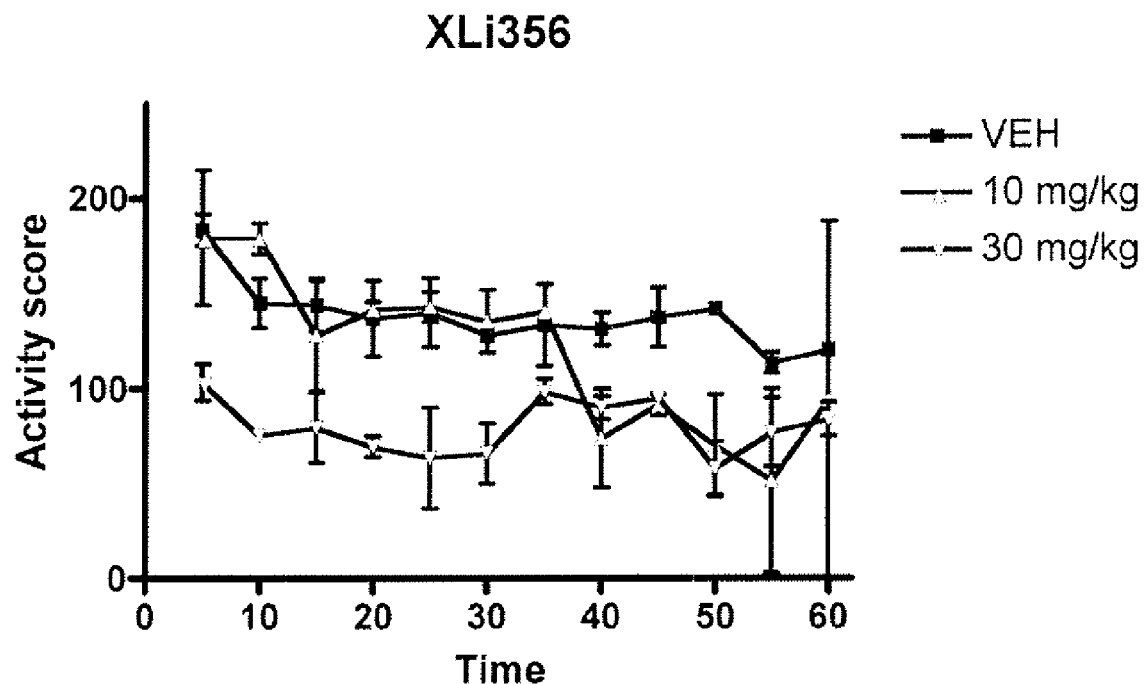
FIG. 23 depicts the effect of compound XLI356 on locomotion. Locomotion is reduced by 30 mg/kg XLi356. 10 mg/kg may be effect locomotion at 40-60 min.
Figure 24:
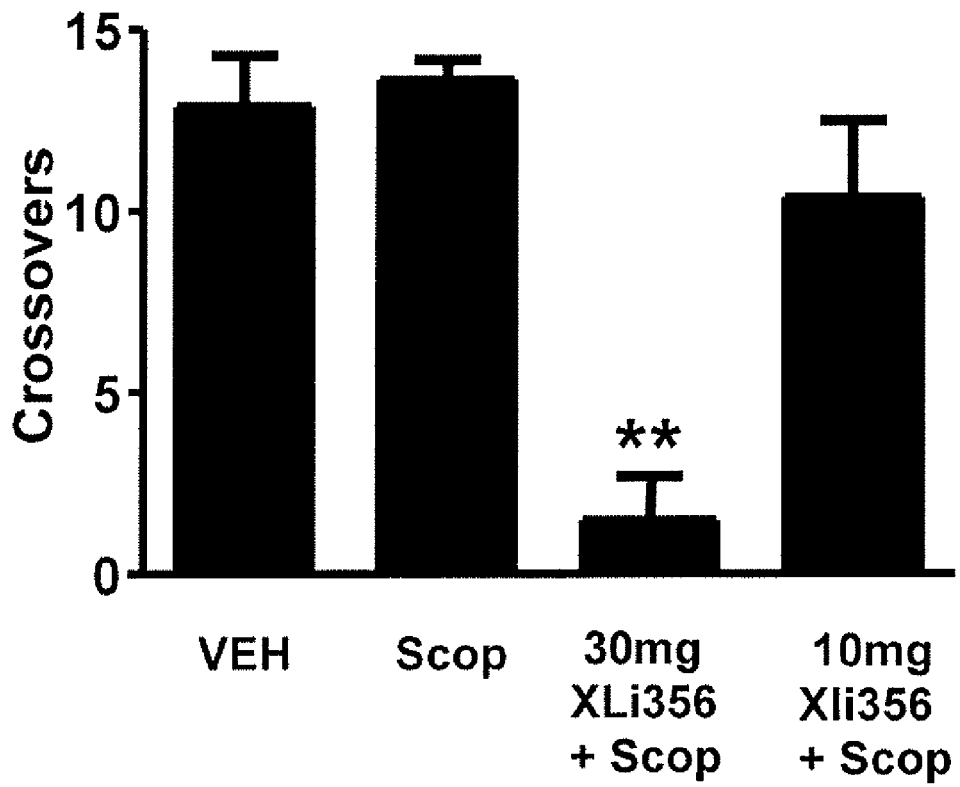
FIG. 24 provides another measure of locomotion demonstrating the reduction at 30 mg/kg, but not at 10 mg/kg.
Figure 25:
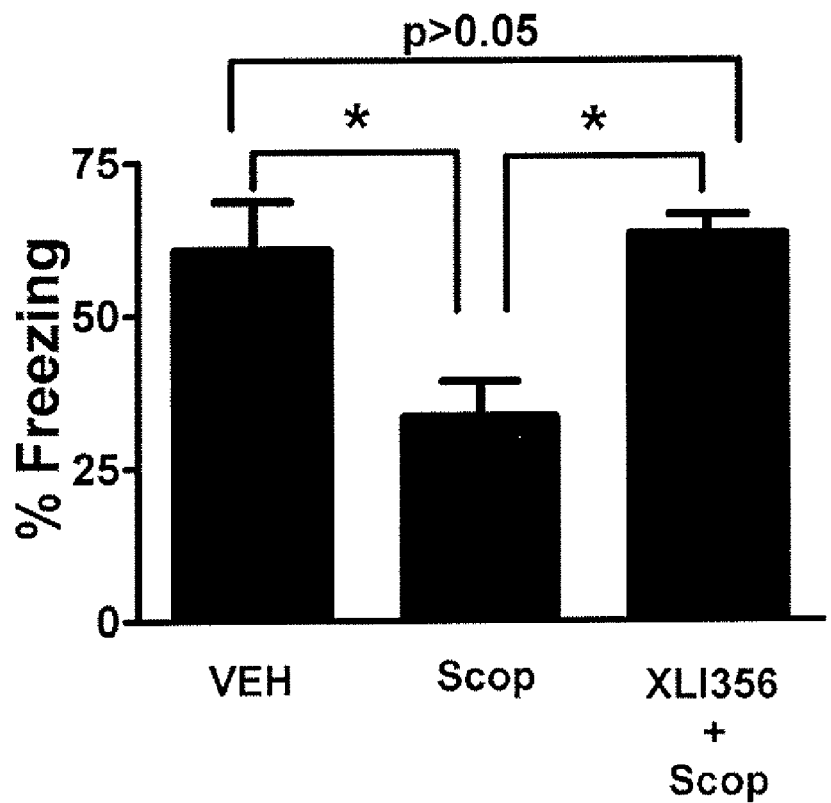
FIG. 25 depicts effect of XLI356 on attenuation of impairment of memory. Scopolamine 1 mg/kg reduces freezing (i.e. impairs memory) typically caused by pairing the context (the cage) with a shock. The compound XLI356 when given at 10 mg/kg attenuates the impairment of memory. Returning the freezing to the level that one typically sees the mouse freeze (i.e. veh).
Figure 26:
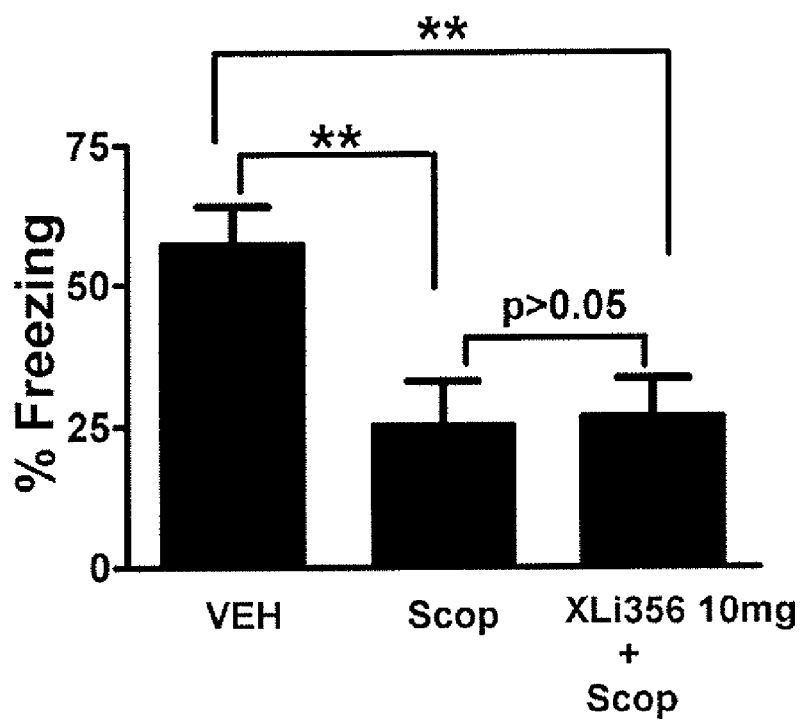
FIG. 26 depicts effect of compound XLI356 on audio cued memory. Audio cued the memory is triggered by sound not the context. XLI356 is not able to reverse this type of memory. It appears that the compound XLi356 reverses effects of scolpamine based on using fear conditioning on contextual memory (hippocampus-driven) only. This is expected to be the result with PWZ-029 also, since audio cued memory is amygdala-driven, Therefore XLI356 and PWZ-029 are likely caused by alpha 5 selectivity which are based in the hippocampus. Both compounds XLI-356 and PWZ-029 analogs appear not to bind at any other types of receptors.

Comparative affinities of DM-I-81 for various α-subtypes are also shown in FIG. 9.

Möhler has proposed that α5 selective inverse agonists or α5 selective agonists might enhance cognition (Möhler et al. 2002, 2004). This is because of the synaptic and extrasynaptic pyramidal nature of α5β3γ2 subtypes, located almost exclusively in the hippocampus. Because of this, a new "potential agonist" which binds solely to α5β3γ2 subtypes has been designed by computer modeling (Zhang 2004; Yin et al. 2004), as shown in FIG. 7. This ligand [DM-I-81 (9)] has an agonist framework and binds only to α5β3γ2 subtypes (Zhang 2004; Yin et al. 2004). Because the binding potency at α5 subtypes is only 174 nM, one of ordinary skill in the art would know to provide both monovalent and bivalent "agonist like" ligands based on the structure of 8-phenyl ligand 9. Once this is completed, one will have potent α5 subtype selective inverse agonists, agonists and antagonists to fully study the physiology of α5 subtypes in rodents (Helmstetter, DeLorey, Galizio, Wenger and coworkers), in pigeons (Wenger and coworkers) and in primates (Rowlett, Platt, and Ator). In a recent study, in collaboration with Savić and coworkers, the inventors employed BCCt to show that α1 subtypes are involved in the amnestic effects of diazepam (Savić et al. 2004).

In regard to α5 receptor subtype selective ligands, Bailey, Helmstetter et. al. have used RY024 to enhance cognition and provide further evidence for the involvement of hippocampal $GABA_A$/benzodiazepine receptors in learning and anxiety. This has been supported by DeLorey et. al, who demonstrated that the closely related α5 inverse agonist RY10 potently reversed scopolamine-induced memory impairment. These α5 inverse agonists provide tools to be used to decipher how $GABA_A$ receptors influence contextual memory, an aspect of memory affected in age associated memory impairment and especially in Alzheimer's disease.[13] In this regard, Savić et. al, have recently employed the α1 preferring ligand BCCt in studies on passive avoidance, which clearly indicated the amnesic effects of midazolam are due to interaction of ligands at α5 as well as α1 BzR subtypes.

Earlier it was reported that BCCt, a diazepam antagonist, was the most subtype selective ligand for α1 receptors reported to date (Huang et al. 2000). Because this antagonist is only 20 fold selective for BzR subtypes, it is usually considered as an α1-preferring antagonist. In primates and rodents, this antagonist exhibits none of the side effects of the 1,4-benzodiazepines (Rowlett et al. 2001; Savić et al. 2004; Lelas et al. 2002; Platt et al. 2002; Rowlett et al. 2003). However, this agent potently reduced alcohol self administration in alcohol preferring rats (P) and in high alcohol drinking rats (HAD) (June et al. 2003; Foster et al. 2004). It does not reduce saccharin lever pressing nor sucrose lever pressing. This anatgonist has been employed to support involvement of the ventral pallidum in the effects of alcohol on alcohol self-administration. Moreover, in P rats and HAD rats, BCCt, antagonized the sedative-hypnotic effects of alcohol. It has now been shown to be orally active (June et al. 2003), and in P and HAD rats, exhibits anxiolytic activity. This study via α1 receptors, indicated BCCt was capable of antagonizing the reinforcing and sedative properties of alcohol. It has been proposed that the unique oral activity of BCCt may represent a prototype of new pharmacological agents to effectively reduce alcohol drinking behavior in human alcoholics (June et al. 2003; Foster et al. 2004).

In the present invention, the preferred linkers for BzR/$GABA_A$ bivalent ligands have been determined by low temperature NMR studies and X-ray analysis. Moreover, a general approach to ring A-substituted indoles and β-carbolines has been developed. In addition, indoles, β-carbolines and other ligands can be prepared on the 100/500/1000 gram scale. This is important for rodent and primate studies require 5 to 20 grams of the ligands.

As shown in FIGS. 1 and 5 the present invention describes the preparation of subtype selective agonists, and inverse agonists of α5 subtypes to study memory and learning as well as amnesia mediated by the hippocampus. All of these ligands have been designed based on the structures of α5 subtype selective ligands prepared in the inventors' laboratory (see Table 1), as well as the efficiency (15 nM)/selectivity of bivalent α5 antagonist XLi093 (8). Accordingly, the majority of the ligands in FIGS. 1 and 5 will bind potently to α5 subtypes and not at all to the others, thereby enabling the study of the pharmacology/physiology of these α5 $GABA_A$/BzR. As discussed above, the synthesis of these ligands is well developed in the inventors' laboratory or the literature.

Pharmacology

The affinity of all ligands at the 6 major recombinant $GABA_A$/BzR subtypes was measured by competition for [$^3$H] Ro15-1788 binding to HEK-T cells expressing both human and rat $GABA_A$/Bz receptors of composition α1β2γ2 (α1), α2β2γ2 (α2), α3β2γ2 (α3), α4β2γ2 (α4), α5β2γ2 (α5) and α6β2γ2 (α6). See FIGS. 8 and 8a. It is well known that the β2 and β3 subunits can be interchanged with no effect on Bz ligand affinity or efficacy. The α4 and α6 subtypes (diazepam insensitive) were assayed using [$^3$H]-Ro154513. These studies are similar to those performed in the laboratory of Bryan Roth who has already expressed the receptors employing the work of Kucken et. al. and Gray et. al.

In brief, for membrane preparations, the cells were scraped on to the ice and diluted into 5 mL of phosphate buffered saline (pH=7.40) and cells pelleted by centrifugation for 5 min. at 4° C. The pellet was resuspended in 1 mL of 50 mM Tris-acetate buffer (pH 7.4) and centrifuged at 18,000 g for 20 min. Radioligand binding assays were performed in 50 mM Tris-acetate buffer (pH 7.4) using $10^{-5}$M diazepam for non-specific binding; typically specific binding will represent 90% of total binding. Each pellet were diluted to 6 mL and then 100 μL of membranes were incubated with approximately 1 nM final concentration of [$^3$H]Ro 15-1788 in a total volume of 250 μL together with serial dilutions of test compound for 90 min. on ice. The membranes were harvested in polyethyleneimine-pretreated Whatman GF/C filters and after drying and addition of scintillation cocktail, counted in a scintillation counter. The cpm retained on the filters was plotted against log concentration (M) and fitted to one site competition equation to obtain the $K_i$ using Graphpad Prizm (V4.0) using the Cheng-Prusoff approximation.

Efficacy at the 6 major receptor subtypes was determined in *Xenopus* oocytes and correlated to the in vivo activity determined below. Since evaluation of the efficacy of ligands in vitro on *Xenopus* oocytes was time consuming, only subtype specific ligands with a selectivity of 40 times or more were preferably evaluated in this measure. A detailed protocol is contained in reference Li, X. Y., Cao, H., Zhang, C. C., Fürtmueller, R., Fuchs, K., Huck, S., Sieghart, W., Deschamps, J. and Cook, J. M., "Synthesis, in Vitro Affinity, and Efficacy of a Bis 8-Ethynyl-4H-Imidazo 1,5a-1,4 Benzodiazepine Analogue, the First Bivalent Alpha 5 Subtype Selective BzR/GABA(A) Antagonist," *J. Med. Chem.*, 46, 5567-5570 (2003).

In brief, adult female *Xenopus laevis* were anesthetized in a bath of ice-cold 0.17% Tricain before decapitation and removal of the frog's ovary. Ovary tissue was removed via a small abdominal incision and stage 5 to 6 oocytes were isolated with fine forceps. After mild colagenase treatment to remove follicle cells, the oocyte nuclei were directly injected with 10-20 µL of injection buffer containing different combinations of human $GABA_A$ subunit cDNAs engineered into the expression vector pCDM8 or pcDNAI/Amp. After incubation for 24 hr, oocytes were placed in a 50 µL bath and perfused with modified Barth's medium.

Cells were impaled with two 2-3 MΩ electrodes which contain 2 MKCl and voltage clamped at a holding potential of −60 mV. GABA modulators were preapplied for 30 seconds before the addition of GABA, which was coapplied with ligands until a peak response was observed. The highest concentration of DMSO employed in this study perfusing the oocyte was 0.1% which had no effect when applied alone at this concentration. The detailed protocols have been reported in publications of the authors.

In regard to cognition, the effect of systemic administration of subtype selective agents on short term memory was determined in white Carneau pigeons. Administration of drug was intramuscularly and the titrating matching-to-sample schedule of reinforcement was used. Matching-to-sample is widely used as a measure of short-term memory, and has been shown to be sensitive to the effects of agents to actions at the $GABA_A$ chloride complex in laboratory animals and humans. In addition, C57BL/6J mice were used to look at the mean delay achieved in the titrating delayed matching-to-position schedule (doses, ip).

Because the hippocampus is involved in the regulation of events underlying learning and memory, α5 subtype selective agents were evaluated for their ability to modulate hippocampal-dependent and hippocampal-independent forms of memory using Pavlovian fear conditioning paradigms with mice or rats. The protocols for these studies were reported in references Bailey, D. J., Tetzlaff, J. E., Cook, J. M., He, X. H. and Helmstetter, F. J., "Effects of Hippocampal Injections of A Novel Ligand Selective for the Alpha 5 Beta 2 Gamma 2 Subunits of the GABA/Benzodiazepine Receptor on Pavlovian Conditioning," *Neurobiol. Learn. Mem.*, 78, 1-10 (2002); Delorey, T. M., Lin, R. C., Mcbrady, B., He, X. H., Cook, J. M., Lameh, J. and Loew, G. H., "Influence of Benzodiazepine Binding Site Ligands on Fear-Conditioned Contextual Memory," *Eur. J. Pharmacol.*, 426, 45-54 (2001). These ligands were also studied in the active avoidance acquisition, retention paradigm and passive avoidance task and to determine if these ligands exhibit any amnestic effects.

Depicted in FIG. 5 is a series of analogs based on the α5 subtype selectivity of potential agonist DM-I-81. In fact, DM-I-81 has shown moderate agonist activity at α5 subtypes recently in oocytes (Han, Cook, Sieghart, Fürtmueller (unpublished results) while very poor efficacy was observed at α1 BzR. All of the ligands in FIG. 5 were designed to incorporate α5-subtype selective determinants (see Table 1) at C (3) of DM-I-81 to enhance α5 subtype selectivity and potency. These are important ligands to study cognition/amnesia. The bromides, 15a-15d, depicted in FIG. 5, will be converted into the imidazo systems 16a-16d under standard conditions and then coupled with phenyltributyltin in a Stille process.

This provided 8-phenyl analogs 9, 9bcd to screen. Furthermore, these analogs were converted into their corresponding 3-alkyl chlorides and then into 3-methoxymethyl and 3-ethoxymethyl analogs represented by α5 targets 93a-94d. These reactions have been developed in the inventors' laboratory previously for other systems. In these new analogs one has combined two features at C(8) and C(3) to enhance α5 subtype selectivity (see Table 1, 12a-c, 13,14). In this same fashion, the 3 ethylester bloisosteres 96a-96d were prepared.

The S-optical isomers 99a-104 of lead α5 ligand DM-I-81 (9) can also be prepared. According to molecular modeling, the modifications to DM-I-81 illustrated in FIG. 5 are completely compatible with the pharmacophore/receptor model for the α5 subtype reported earlier.

Finally, the potential α5 subtype selective bivalent ligands depicted in FIG. 1 are based on the α5 subtype selectivity of XLi093 as well as the α5 subtype selectivity of DM-I-81 and bisacetylene 14, clearly illustrated in Table 1.

Upon combining these effects, α5 subtype selectivity may be determined by modeling as described here. In brief, RY-80 (6) was converted into XLi093 (8) or its analogs 107 or 108 exactly analogous to the work in reference discussed above. Catalytic hydrogenation furnished bisethyl ligands 109a-109c, the first of which DeLorey has already shown enhances cognition in the scopolamine paradigm. The bromide 105 related to RY-80 was converted into chloride 110 via standard methods and then condensed with piperidine or various glycols to furnish bivalent ligands 111a or 112a-c expected to exhibit good water solubility for ip administration. Bivalent ligands 112a-c were converted into the α5 targets 113a-c via the standard Heck-type/TBAF protocol. In exactly the same fashion, DM-I-81 can be converted into the bivalent 8,8'-bisphenyl bivalent targets 115a-c (see FIG. 1).

The synthesis of bivalent bisacetylenic targets 132a-c were based on the conversion of bromide 130 into a bisacetylene analog (see 14, Table 1) executed earlier by He. Conversion of bromide 130 into bivalent analogs was executed, as outlined in reference discussed above and the bottom of FIG. 1. In this case, trimethyl/silylacetylene was replaced by trimethyl silyl bisacetylene in the Heck-type process. This bivalent bisacetylene incorporated the α5 subtype selectivity of both XLi093 (8) and bisacetylene 14 into the same ligand. This binds only to α5 receptors, and is expected to be an inverse agonist. The synthetic route will provide potent α5 selective inverse agonists, antagonists, and agonists to study cognition and amnesia in the hippocampus.

Since the GABAergic system is the major inhibitory neurotransmitter system in the CNS, it has tremendous therapeutic potential. Alterations in $GABA_A$ function from controls are known to occur in anxiety disorders, including panic disorder, epilepsy, hypersensitive behavior, phobias, schizophrenia, alcoholism, Angelmans Syndrome and Rhetts syndrome as well as other diseases. Since BzR ligands modulate this system, the design of subtype selective ligands is one way to generate better, safer therapeutic agents.

In this invention, as shown in FIGS. 1 and 5, emphasis is on development of agonists, antagonists and inverse agonists that bind only to the α5β3γ2 subtypes. Synthesis and pharmacological evaluation of these subtype selective agents will permit the assignment of the correct physiological functions to α5 subtypes. This is of special importance here in regard to cognition/amnesia mediated by the hippocampus. The invention generally presents potential therapeutic agents to improve memory and learning.

Correlation of a specific BzR subtype to a specific pharmacological response is crucial for understanding the mechanisms which underlie anxiety disorders, sleep disorders, convulsions and cognitive deficits, as well as design of selective agents to treat these disease states devoid of abuse potential.

Accordingly, the present invention generally provides molecules and methods for the treatment and/or prevention and/or memory enhancement in patients in risk thereof. In one embodiment, the present invention provides a compound of Formula IV, a salt or a prodrug thereof,

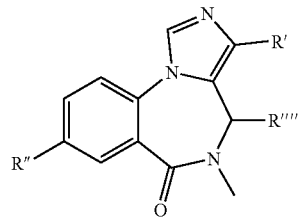

IV wherein R' is branched or straight chain C1 to C4 alkyl or a methyl cyclopropyl, OMe, OEt, COOMe, COOEt, COO-i-Pr, COO-t-Bu, CH$_2$R$_1$, wherein R$_1$, is OH, Cl, OMe, OEt N(Et)$_2$, N(iPr)$_2$ or

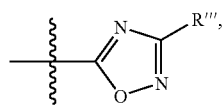

wherein R''' is H or branched or straight chain C1 to C4 alkyl or a methyl cyclopropyl, —CH$_2$—OMe, —CH$_2$—OEt, —CH$_2$—O-iPr, —CH$_2$—O-tBu, —COMe, —COEt, —COPr, —COBu, —CO-iPr, —CO-t-Bu;

R'' is F, Cl, Br, NO$_2$, Et, —C≡C—R$_2$, —C≡C—C≡C—R$_2$, where R$_2$ is H, Si (CH$_3$)$_3$, t-butyl, isopropyl, methyl, or cyclopropyl; and R'''' is H or branched or straight chain C1 to C4 alkyl or a methyl cyclopropyl.

In this embodiment, preferably, the compound, salt or prodrug of Formula IV, selectively binds to α$_5$β$_2$γ$_2$ or α$_5$β$_3$γ$_2$ receptors, More preferably, the compound of Formula IV is

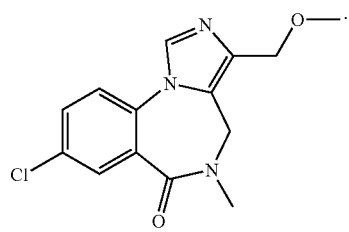

In a preferred exemplary embodiment, the compounds of Formula I are shown below.

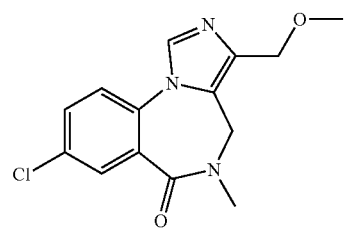

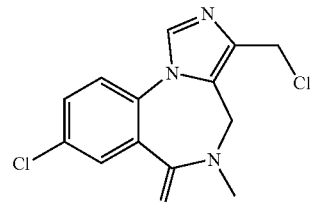

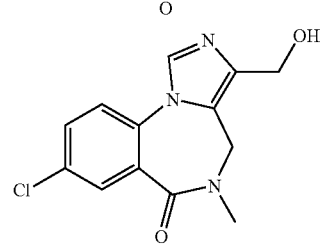

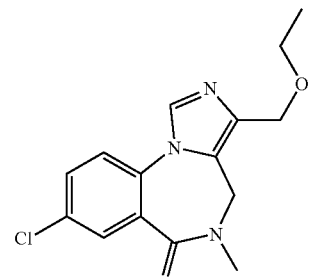

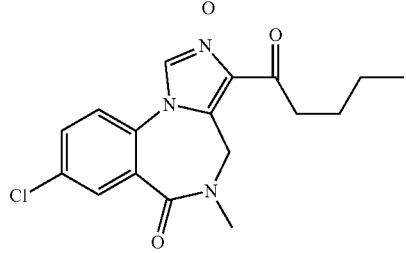

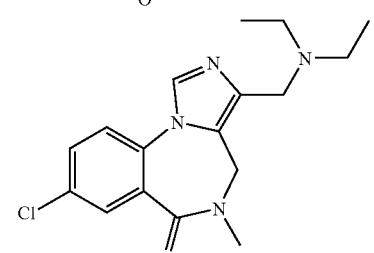

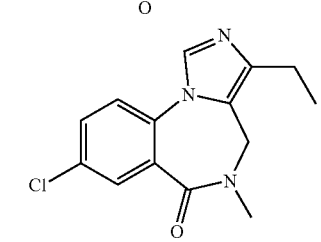

The above compounds may be prepared according to scheme provided for the compound PWZ-029.

In a preferred embodiment, the present invention provides a compound of Formula I, a salt or a prodrug thereof, wherein Formula is depicted as shown below:

wherein:

Ar is phenyl or thienyl;

Ar' is a substituted or unsubstituted 5 membered or a 6 membered carbocyclic ring, or a 5 or 6 membered heterocylic ring having at least one heteroatom selected from N, O and S, wherein if substituted, the substituent is one or more of F, Cl, Br or $NO_2$ at the 2'-position;

R' is OMe, OEt, $CO_2Et$, $CH_2R$, wherein R is OH, Cl, OMe or OEt or wherein R'''' is H or branched or straight chain C1 to C4 alkyl or a methyl cyclopropyl;

R'' is H or (R) or (S)$CH_3$, OH, OAc, $NO_2$, $OCON(CH_3)_2$, $COOCH_3$, $COOCH_2CH_3$.

in a preferred exemplary embodiment, the compounds of Formula I are shown below:

96a, x = CH, R'' = $CH_3$
96b, x = CF, R'' = $CH_3$
96c, x = N, R'' = $CH_3$
96d, x = CCl, R'' = $CH_3$
97, The same analogs with R'' = H$^d$
98, The same analogs with R'' = $CH_2CH_3$$^d$ 9b, x = CF
9c, x = N
9d, x = CCl -continued

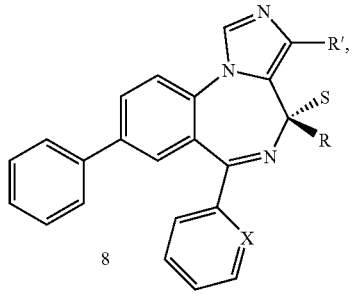

8

99a, x = CH, R = CH₃, S = H, R' = CO₂Et
99b, x = CH, R = H, S = CH₃, R' = CO₂Et (negative control)
100a, x = CH, R = CH₃, S = H, R' = CH₂Cl
100b, x = CH, R = CH₃, S = H, R' = OCH₃
100c, x = CH, R = CH₃, S = H, R' = OCH₂CH₃
101a, x = CF, R = CH₃, S = H, R' = CO₂Et
101b, x = N, R = CH₃, S = H, R' = CO₂Et
101c, x = CCl, R = CH₃, S = H, R' = CO₂Et
102, All of the above with R = OH, S = H or R = OAc, S = H[f]
103, All of the above with R' = to the ethyl, methyl, or isopropyl bioisosteres[d]
104, All of the above with the 6-phenyl group replaced by 2-thienyl or 3-thienyl group[g]

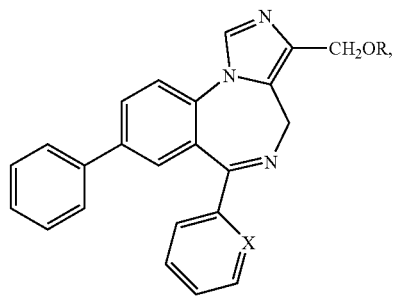

93a, x = CH, R = Me (10j)
93b, x = CF, R = Me
93c, x = N, R = Me
93d, x = CCl, R = Me
94a, x = CH, R = CH₂CH₃
94b, x = CF, R = CH₂CH₃
94c, x = N, R = CH₂CH₃
94d, x = CCl, R = CH₂CH₃

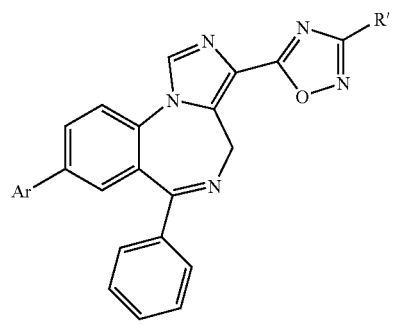

6a Ar = phenyl
    R' = methyl, ethyl, isopropyl
6b Ar = 2 or 3-thienyl
    R' = methyl, ethyl,
    isopropyl, wherein thienyl =

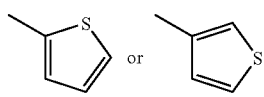

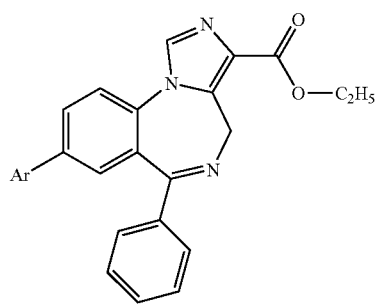

4 Ar = 2 - thienyl
  or 3-thienyl wherein thienyl is

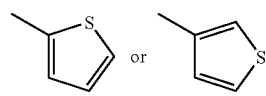

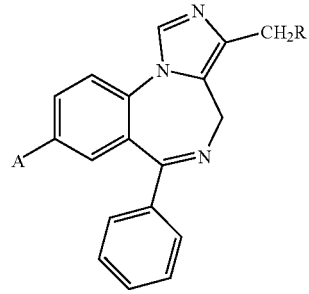

5a Ar = phenyl
    R = Cl or OMe or OEt
5b Ar = 2 or 3-thienyl
    R = Cl or OMe or OEt

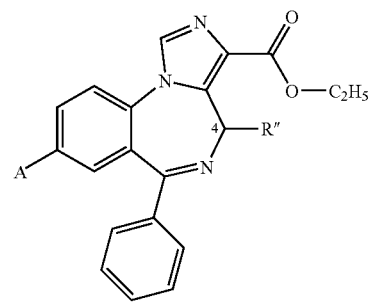

7 Ar = phenyl, 2-thienyl, or 3-thienyl
  R'' = (R) or (S)CH₃, OH, OAc, NO₂,
  OCON(CH₃)₂, COOCH₃, COOCH₂CH₃

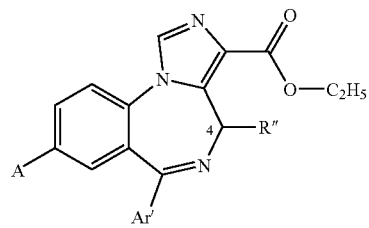

8 Ar = phenyl or 2-thienyl or 3-thienyl
  Ar' = 2-thienyl or 3-thienyl, or 2'-chlorophenyl,
  or 2'-fluorophenyl, or 2'-nitrophenyl
  or 2'-pyridyl.
  R'' = (R) or (S)CH₃, OH, OAc, NO₂,
  OCON(CH₃)₂, COOCH₃, COOCH₂CH₃

-continued

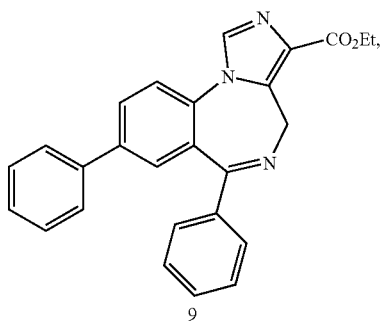

9

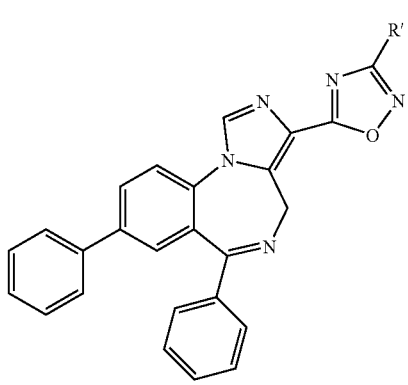

202a, R' = CH$_3$
202b, R' = CH$_2$CH$_3$
202c, R' = isopropyl

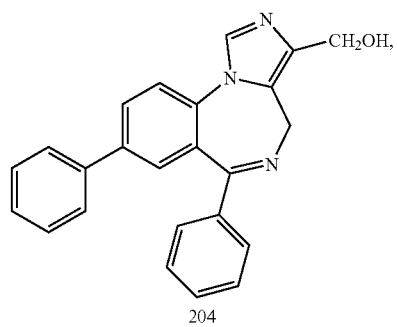

204

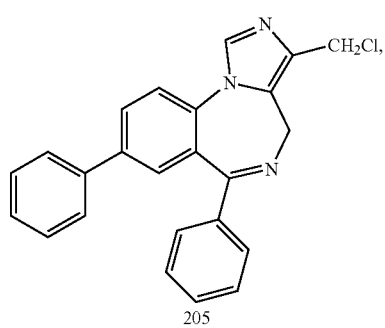

205

-continued

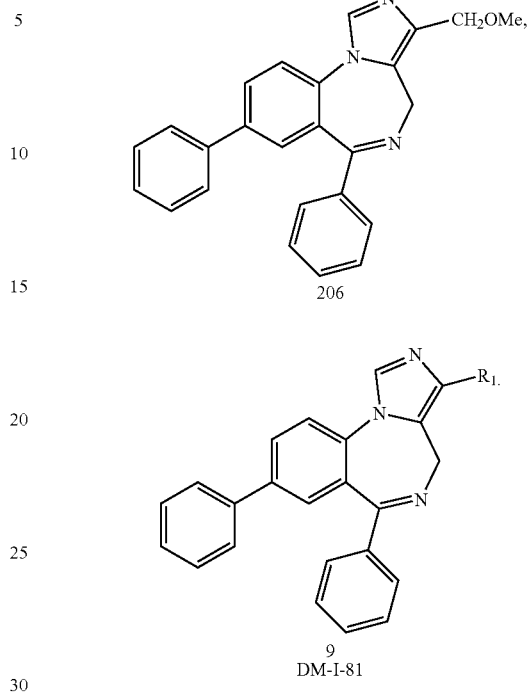

206

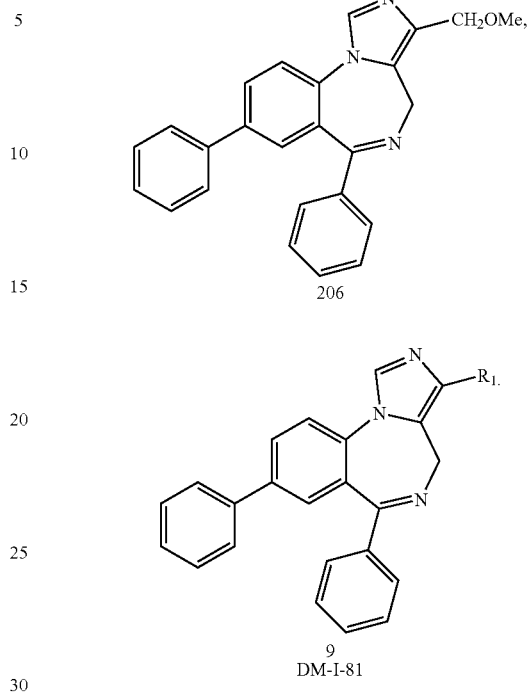

9
DM-I-81

In this embodiment, the compound, salt or prodrug selectively binds to $\alpha_5\beta_2\gamma_2$ or $\alpha_5\beta_3\gamma_2$ receptors.

In yet another preferred embodiment, the present invention provides a compound of Formula II, a salt or a prodrug thereof:

II

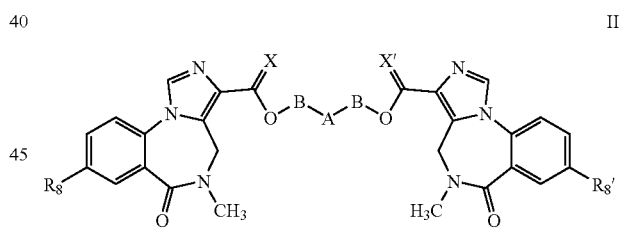

wherein:

$R_8$ or $R_8'$ is independently selected from $C_2H_5$, $C_6H_5$, Br, —C≡C—R, —C≡C—C≡C—R; where R is H, Si(CH$_3$)$_3$, t-butyl, isopropyl, methyl, or cyclopropyl;

X or X' is independently selected from H$_2$ or O;

B-A-B is —CH$_2$—(CH$_2$)$_n$—CH$_2$— or

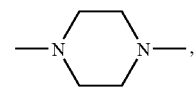

wherein n is an integer 1, 2 or 3.

In yet another embodiment, the present invention provides a compound of Formula III, a salt or a prodrug thereof,

III

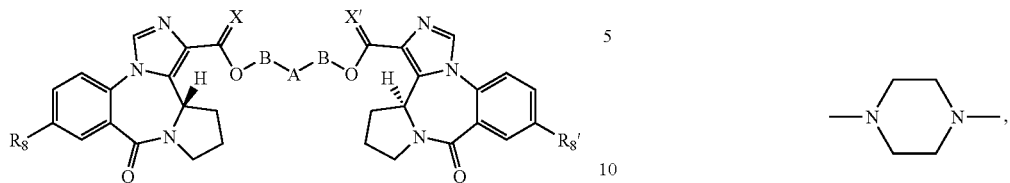

wherein $R_8$ or $R_8'$ is independently selected from $C_2H_5$, $C_6H_5$, Br, —C≡C—R, —C≡C—C≡C—R, where R is H, Si$(CH_3)_3$, t-butyl, isopropyl, methyl, or cyclopropyl;

X or X' is independently selected from $H_2$ or O;

B-A-B is —$CH_2$—$(CH_2)_n$—$CH_2$— or

5

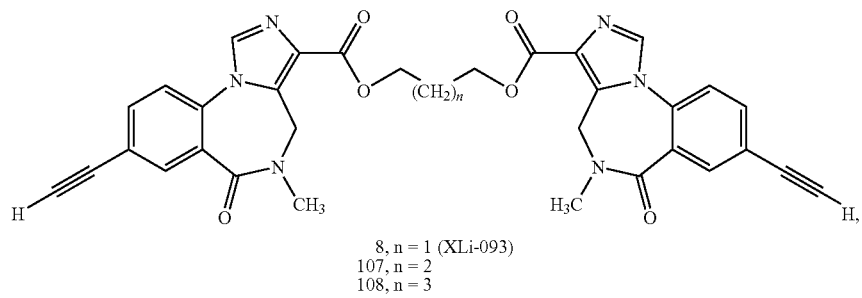

10 wherein n is an integer 1, 2 or 3.

In a preferred exemplary embodiment, the compounds of Formula II or III are depicted as below:

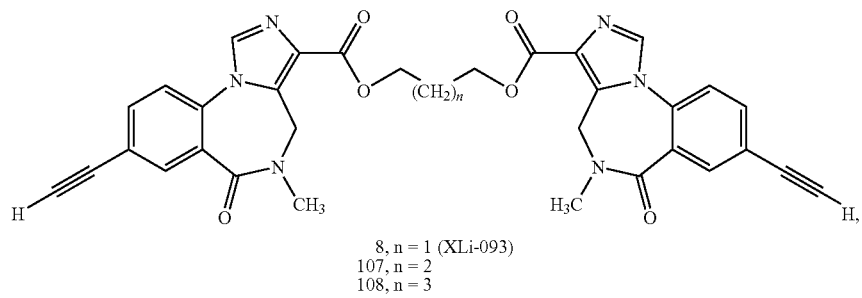

8, n = 1 (XLi-093)
107, n = 2
108, n = 3

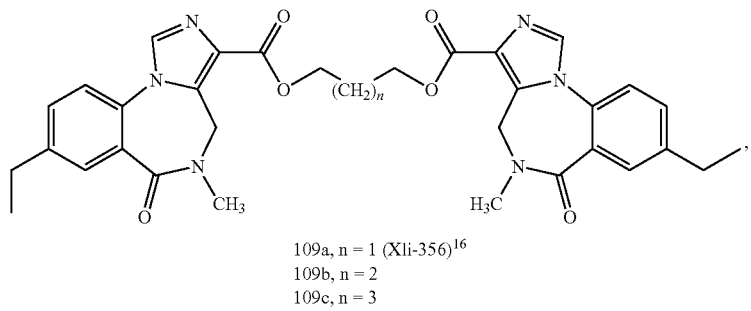

109a, n = 1 (Xli-356)[16]
109b, n = 2
109c, n = 3

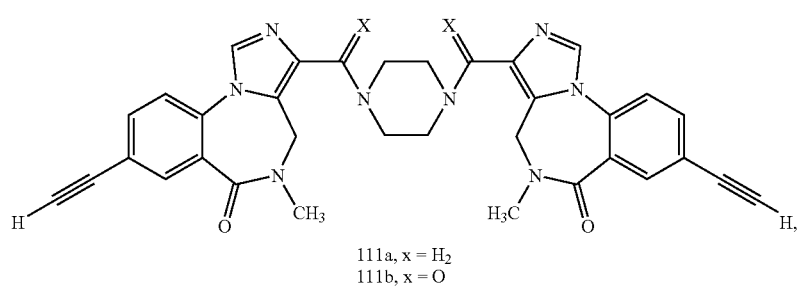

111a, x = $H_2$
111b, x = O

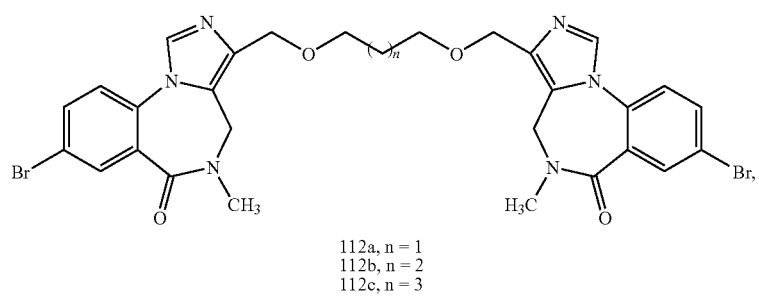

112a, n = 1
112b, n = 2
112c, n = 3

-continued

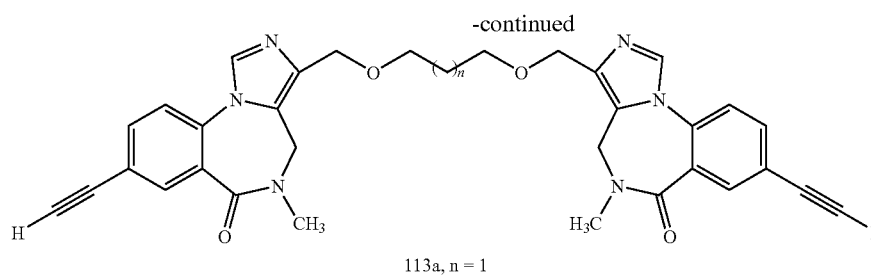

113a, n = 1
113b, n = 2
113c, n = 3

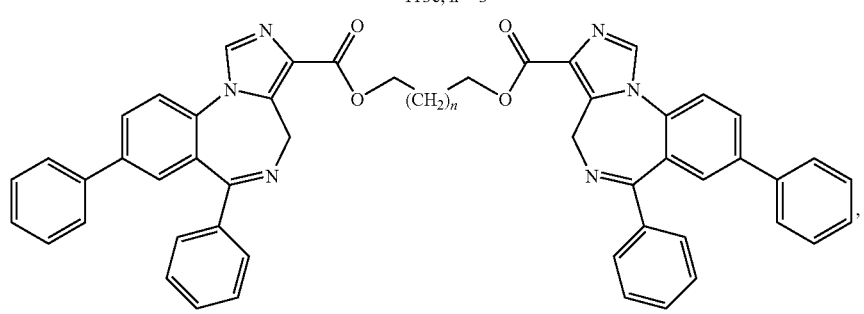

115a, n = 1
115b, n = 2
115c, n = 3

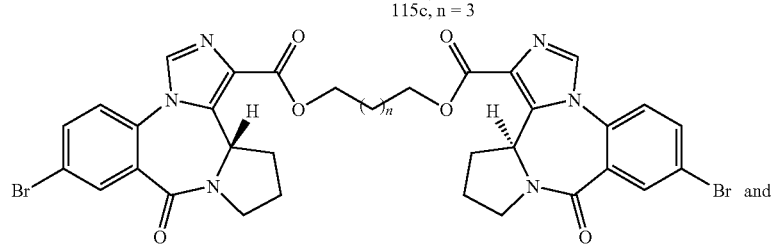

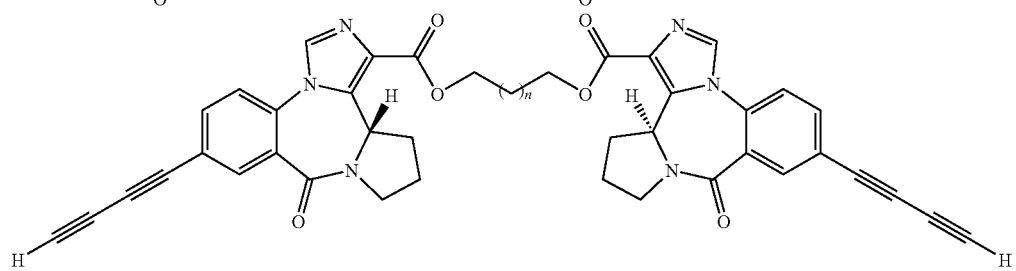

132a, n = 1
132b, n = 2
132c, n = 3

In this embodiment, the compounds, salts or prodrugs of Formula II or III selectively binds to $\alpha_5\beta_2\gamma_2$ or $\alpha_5\beta_3\gamma_2$ receptors.

A compound of Formula V, or a salt thereof,

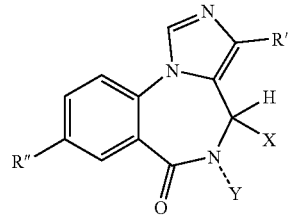

V wherein R' is branched or straight chain C1 to C4 alkyl or a methyl cyclopropyl, OMe, OEt, COOMe, COOEt, COO-i-Pr, COO-t-Bu, CH$_2$R$_1$, wherein R$_1$ is OH, Cl, OMe, OEt N(Et)$_2$, N(iPr)$_2$,

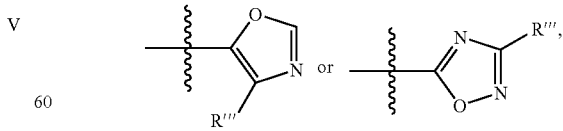

wherein R''' is H or branched or straight chain C1 to C4 alkyl or a methyl cyclopropyl, —CH$_2$—OMe, —CH$_2$—OEt, —CH$_2$—O-iPr, —CH$_2$—O-tBu, —COMe, COEt, —COPr, —COBu, —CO-iPr, CO-t-Bu;

R" is F, Cl, Br, NO$_2$, Et, —C≡C—R$_2$, —C≡C—C≡C—R$_2$, where R$_2$ is H, Si (CH$_3$)$_3$, t-butyl, isopropyl, methyl, or cyclopropyl, X and Y form a 4 membered or 5 membered carbocyclic ring or 4 membered or 5 membered heterocyclic ring, wherein the heteroatom is selected from O, N, or S.

In this embodiment, the compounds, salts or prodrugs of Formula V selectively binds to α$_5$β$_2$γ$_2$ or α$_5$β$_3$γ$_2$ receptors.

In a preferred exemplary embodiment, the compounds of Formula V are depicted as below:

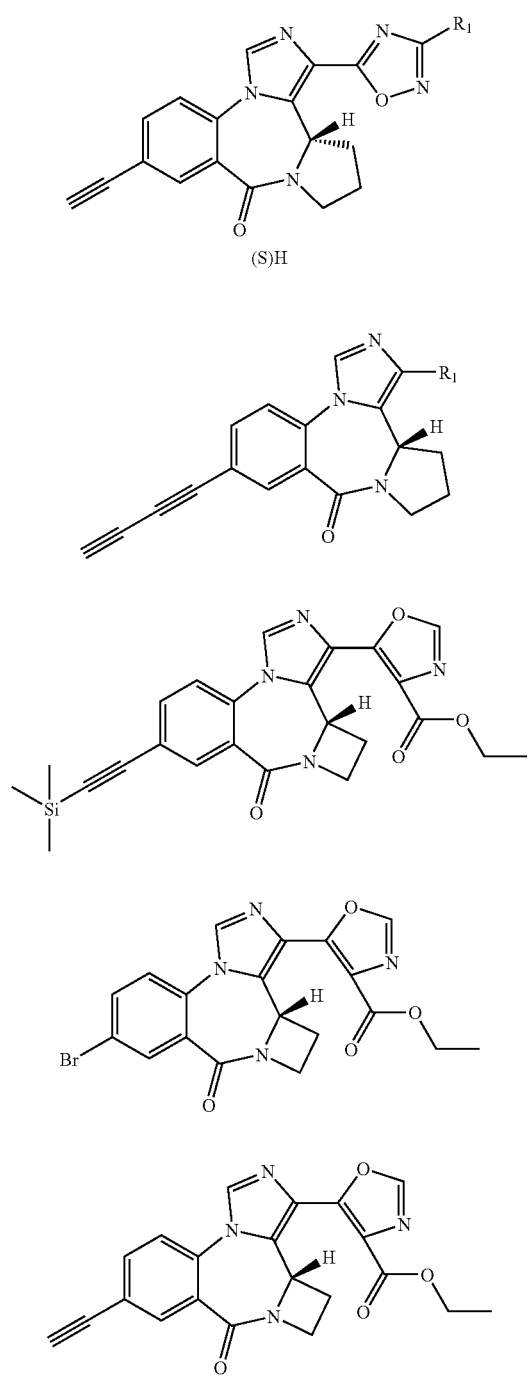

In another embodiment, the present invention also provides the use of a compound, salt or prodrug of Formula I, II, III, IV or V for the production of a pharmaceutical composition for the treatment of memory deficient and/or enhancement of memory.

In this exemplary embodiment, the pharmaceutical composition having the compound, salt or prodrug of Formula I, II, III, IV or V is used to selectively bind to α$_5$β$_2$γ$_2$ or α$_5$β$_3$γ$_2$ receptors.

Another embodiment of the present invention provides a method for prevention and/or treatment of memory deficit related conditions in a subject in risk thereof. This method comprises the step of administering to said subject an effective amount of a compound of Formula I, II, III, IV or V, a pharmaceutically acceptable salt, or a prodrug thereof. Also, in this embodiment, the compound, salt or prodrug selectively binds to α$_5$β$_2$γ$_2$ or α$_5$β$_3$γ$_2$ receptors. In another preferable embodiment, the subject is administered an effective amount of a compound of Formula I, II, III, IV or V and a pharmaceutically acceptable salt, or a prodrug thereof, in combination with Zn$^{2+}$ ions. Zn$^{2+}$ ions appear to enhance the selective binding of certain compounds of the invention to the α$_5$β$_2$γ$_2$ or α$_5$β$_3$γ$_2$ receptors, also as depicted in FIGS. 12-18.

Another embodiment of the present invention provides a pharmaceutical composition. The composition comprises: (a) a compound of Formula I, II, III, IV or V; or (b) a pharmaceutically acceptable salt of said compound; or (c) a pharmaceutically acceptable prodrug of said compound; and (d) a pharmaceutically-acceptable carrier. In this embodiment, the compound, salt or prodrug selectively binds to α$_5$β$_2$γ$_2$ or α$_5$β$_3$γ$_2$ receptors.

In the above embodiments "alkyl" refers to a straight or branched halogenated or unhalogenated alkyl group having 1-6 carbon atoms. "Cycloalkyl" refers to one containing 3-7 carbon atoms. Also, in the above embodiments "cyclic" refers to a phenyl group "heterocyclic" refers to a 2-pyridine or a 2- or 3-thiophene.

The compounds of the present invention are GABA$_A$ receptor ligands which exhibit activity due to increased agonist or inverse agonist efficacy at GABA$_A$/α5 receptors. The compounds in accordance with this invention may possess at least 2-fold, suitably at least 5-fold, and advantageously at least a 10-fold, selective efficacy for the GABA$_A$/α5 receptors relative to the GABA$_A$/α1 receptors. However, compounds which are not selective in terms of their agonist efficacy for the GABA$_A$/α5 receptors are also encompassed within the scope of the present invention. Such compounds will desirably exhibit functional selectivity by demonstrating activity with decreased sedative-hypnotic/muscle relaxant/ataxic activity due to decreased efficacy at GABA$_A$/α1 receptors.

For use in medicine, the salts of the compounds of formulas as shown above will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts, alkaline earth metal salts, e.g. calcium or magnesium salts; and salts formed with suitable organic ligands, e.g. quaternary ammonium salts.

The present invention includes within its scope prodrugs of the compounds of formulas as shown above. In general, such prodrugs will be functional derivatives of the compounds of formulas as shown which are readily convertible in vivo into the required compound of formulas. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric center, they may accordingly exist as enantiomers. Where the compounds according the invention possess two or more asymmetric centers, they may additionally exist as diastereoisomers. It is to be understood that all such isomers and mixtures thereof in any proportion are encompassed within the scope of the present invention.

The compounds according to the present invention may prevent memory deficit activity, or enhance cognizant activity. Moreover, the compounds of the invention are substantially non-sedating and non-ataxic as may be shown by the tables listed below from the binding of specific GABA receptors, or lack thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that the compounds of the present invention may be incorporated into transdermal patches designed to deliver the appropriate amount of the drug in a continuous fashion. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage from affording the advantage of prolonged action. For example, the tablet or pill can comprise an inner dosage and an outer dosage component, the latter being in the form of an envelope over the former. The two components can be separated by an enteric layer which, serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium caboxymethylcellulose, methylcellulose, polyvinylpyrrolidone or gelatin.

In the treatment and or prevention of of memory deficit, or enhancement of cognizance, suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day, or on a continuous basis via, for example, the use of a transdermal patch.

The present invention further provides following examples of preferred methodologies, techniques and embodiments of the present invention. These are for illustrative purposes only and should not be deemed as narrowing the scope of the present invention.

EXAMPLES

Synthesis of DM-I-81

5-phenyl-1,3-dihydro-benzo[e][1,4]diazepin-2-one (2)

Dissolve 2-aminobenzophenone 1 (100 g, 0.507 mol) in $CHCl_3$ (600 mL) and add $NaHCO_3$ (90 g, 1.07 mol). The reaction mixture was cooled with an ice-water bath to around 0° C. and bromoacetyl bromide (51 mL, 0.586 mol) in 200 mL $CHCl_3$ was added dropwise. The reaction mixture was stirred overnight. The TLC (hexane:EtOAc 5:1) was checked to make sure that all the starting material was gone. Then ice-water was added into the reaction mixture to quench the reaction. The organic layer was separated and the water layer was extracted with $CHCl_3$. All of the organic layer was combined and washed with saturated aqueous $NaHCO_3$, water and it was dried over $Na_2SO_4$. After the solvent was concentrated to about 600 mL, it was ready for the next step.

MeOH (2 L) was saturated with ammonia and the solution from the above step was added with the cooling of an ice-water bath. The mixture was allowed to warm to room temperature gradually, and heated up to reflux overnight with caution. It was then cooled and the solvent was removed under vacuum. The solid which was left was washed with water and filtered. The cake was washed with water and EtOAc. After drying, a yellow solid (99 g, 83% from 1) of 2 was obtained, which is pure enough to be used directly for the next step.

7-bromo-5-phenyl-1,3-dihydro-benzo[e][1,4]diazepin-2-one (3)

The starting material (99 g, 0.42 mol) from the last step was dissolved in acetic acid (1550 mL), and sulfuric acid (123 mL) was added. Then the bromine (43 mL, 0.84 mol) solution in acetic acid (300 mL) was added dropwise into the mixture. It was kept stirring, until analysis by NMR indicated that all the starting material was gone (A small amount of sample from the reaction mixture was withdrawn by pipette and it was basified with aqueous NaOH to pH neutral; it was then extracted with EtOAc, dried $Na_2SO_4$, and the NMR was checked after removal of the solvent). At this point, there was a lot of solid which precipitated from the solution. It was filtered and washed with EtOAc, A yellow solid (87.1 g, 65.9%) was obtained as a partly pure compound. It was dried in an oven and used in the next step.

Ethyl 8-bromo-6-phenyl-4H-benzo[f]imidazo[1,5-a][1,4]diazepine-3-carboxylate (4)

The starting material (15.7 g, 0.05 mol) (3) was suspended in THF (250 mL), and it the slurry was cooled with a dry ice/EtOAc bath to 10° C. Sodium hydride (4.2 g, 0.105 mol, 60% dispersion in mineral oil) was then added into the suspension. The reaction mixture was stirred and was left to cool to room temperature gradually, until evolution of bubbles ceased. The solution was cooled to −10° C., and diethyl chlorophosphate (11.5 mL, 0.08 mol) was added. The bath was then removed and the mixture was kept stirring for 3 hrs.

In the meantime, sodium hydride (4 g, 0.10 mol) was suspended in THF (250 mL) in another flask. This suspension was cooled to −10° C., after which ethyl isocyanoacetate (6.54 mL, 0.06 mol) was added. The stirring was maintained until evolution of bubbles ceased.

The first reaction mixture was cooled to −30° C., and then the latter one was transferred into it with a cannula. This mixture was stirred continuously for 24 hrs and quenched with 10 mL of acetic acid after cooling with an ice-water bath. Ice was added to the solution and the reaction mixture was extracted with EtOAc. The EtOAc layer was combined and washed with an aqueous solution $NaHCO_3$, and brine. It was dried over $Na_2SO_4$. After removal of the solvent, it was purified by flash column chromatography (silica gel, EtOAc: hexane 1:1, 2:1, 4:1) and then a white solid (8.17 g, 40%) (4) was obtained.

Often a portion of the product (4) could be crystallized by adding (EtOAc:hexane 1:1) to the crude mixture before chromatography. The solid was filtered off and used. The residue was chromatographed. This material was used directly in the next step.

Ethyl 8-phenyl-6-phenyl-4H-benzo[f]imidazo[1,5-a][1,4]diazepine-3-carboxylate (9) (DM-I-81)

The starting bromide 4 (102 mg, 0.25 mmol) was dissolved in toluene (20 mL) and tributylphenyltin (0.1 ml, 0.3 mmol) was added. The solution which resulted was degassed under vacumn and then $Pd(PPh_3)_4$ (27 mg, 0.1 mmol) was added under argon. The mixture was allowed to reflux for 12 hours and then stopped. The phenyl compound 9 was concentrated under reduced pressure and purified by column chromatography (silica gel, EtOAc). It was crystallized from EtOAc to give colorless crystals 9 (DM-I-81, 65 mg) in 64% yield. 3: mp: 200-201° C.; IR (KBr) 3445.9, 3102.2, 2976.4, 1701.7, 1614.0, 1577.1, 1561.2, 1490.3, 1372.6, 1270.0, 1191.1, 1156.5, 1125.1, 1077.0, 952.2, 769.5, 699.1 cm$^{-1}$; $^1$HNMR (300 MHz, CDCl3) δ 1.44 (t, 3H, J=7.2 Hz), 4.15 (d, 1H, J=12.4 Hz), 4.44 (m, 2H), 6.09 (d, 1H, J=12.4 Hz), 7.38~7.71 (m, 12H), 7.90 (dd, 1H, J=2.0, 8.4 Hz), 8.01 (s, 1H). MS (EI) m/e (rel intensity): 407 (18), 347 (52), 361 (50), 333 (100), 230 (21); Anal. Calcd. For $C_{26}H_{21}N_2O_3$: C, 76.64; H, 5.19; N, 10.31. Found: C, 76.37; H, 5.20; N, 10.33.

Figure 4:
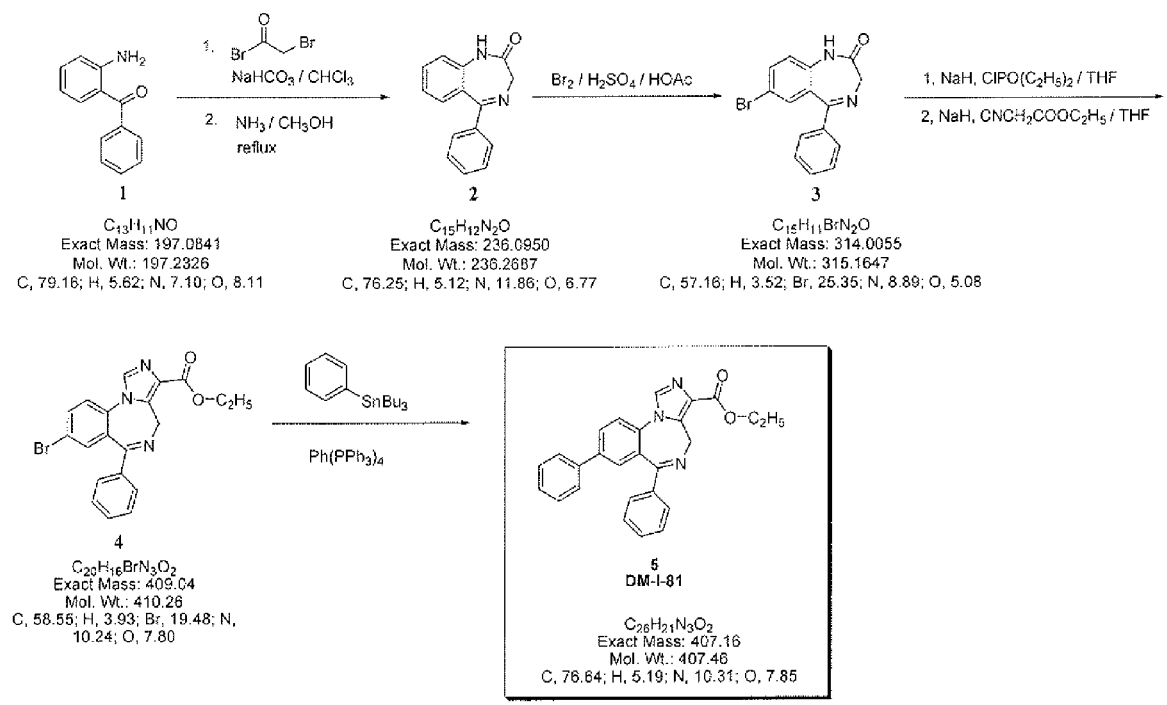
FIG. 4 depicts the synthesis of DM-I-81 and its analogs.

The synthesis of DM-I-81 and its analogs are shown in the FIGS. 4 and 5.

Bioisostere of DM-I-81

The methyl N-hydroxy-acetamidine (0.545 g, 7.36 mmol) and freshly activated molecular sieves (0.375 g) were suspended in dry THF (45 mL) under an argon atmosphere and this mixture was allowed to stir for 10 minutes at room temperature. To this suspension, NaH (0.295 g, 60% dispersion in mineral oil) was added in one addition. The resulting suspension was allowed to stir at room temperature for 30 minutes, after which the ethyl ester starting material, DM-I-81, was dissolved in dry THF (60 mL) and added via syringe to the previous suspension. The resulting suspension was heated to reflux and allowed to stir for 2 hours or until TLC (silica gel) had indicated that all the starting material had been consumed. The suspension was allowed to cool to room temperature and quenched with glacial acetic acid (2.0 mL) and stirring continued for 10 minutes. The reaction mixture was filtered through Celite and washed with $CH_2Cl_2$. The organic filtrate was washed with water, brine and dried with $K_2CO_3$. The resulting organic solution was evaporated under reduced pressure to remove all organic solvents. The residue which resulted was chromatographed on a flash column (EtOAc: Hex 5:1) to remove impurities and to isolate the desired bioisostere of DM-I-81.

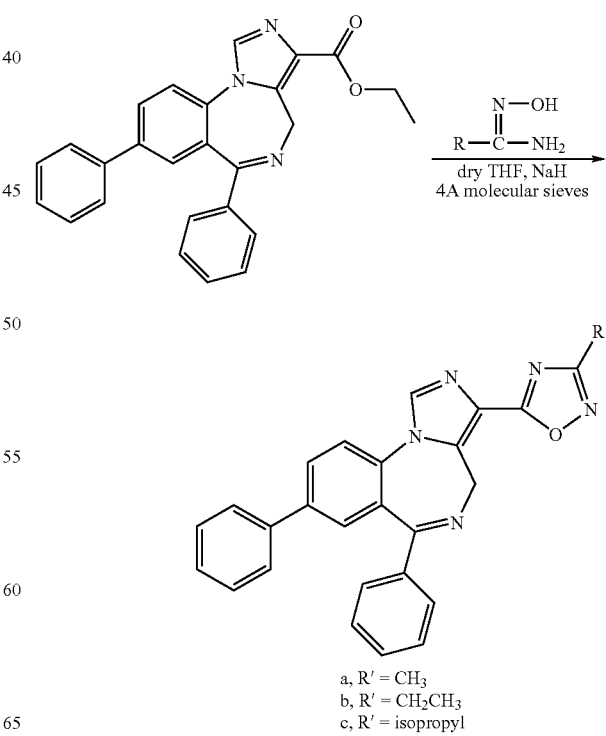

a, R' = CH$_3$
b, R' = CH$_2$CH$_3$
c, R' = isopropyl

Analogs of DM-I-81

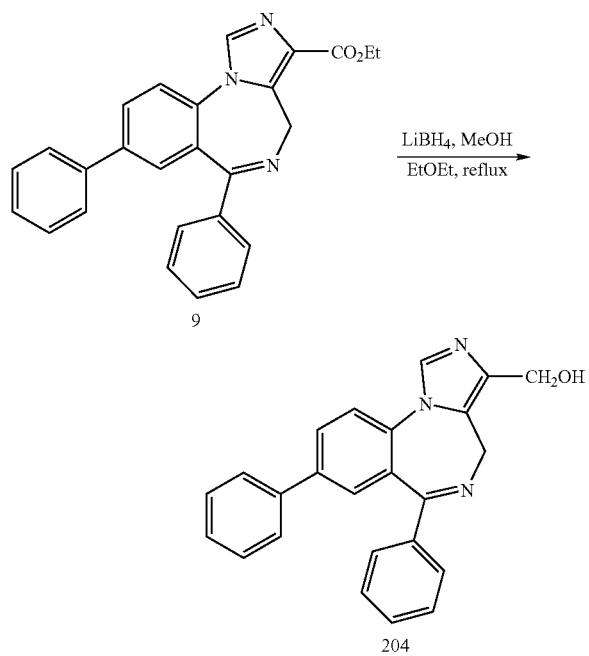

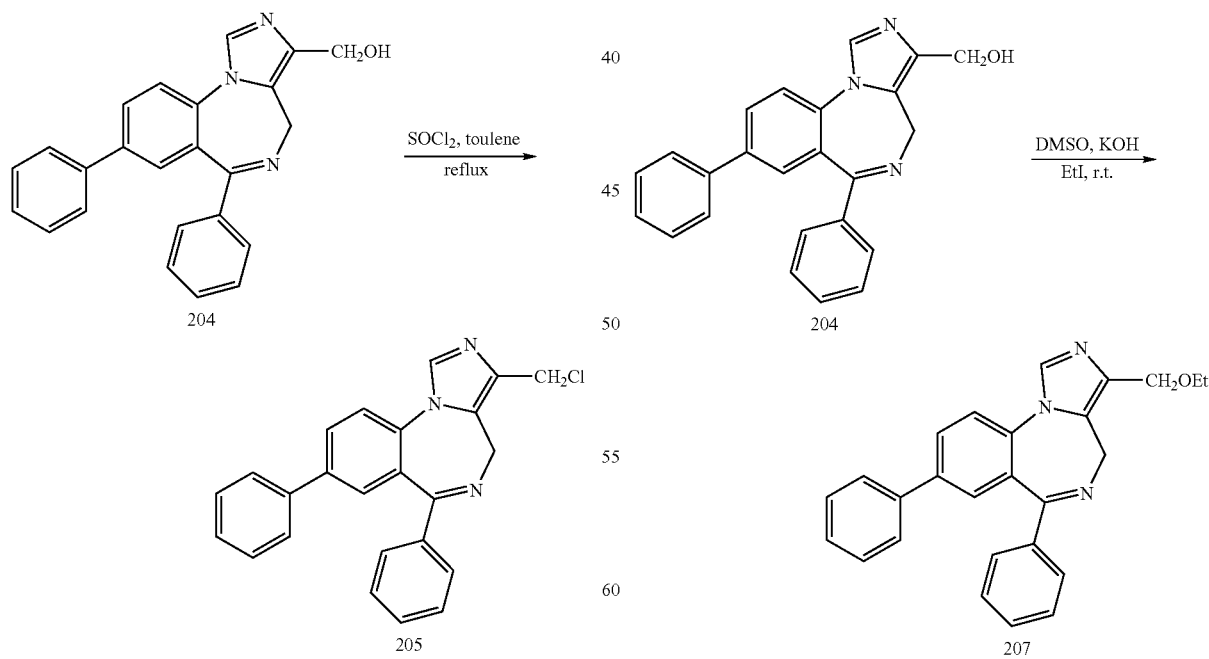

To 200 mg (0.5 mmol) of DM-I-81 (203) was added 0.03 mL methanol (0.75 mmol) and 0.5 mL LiBH$_4$ (2.0 M in THF) in 10 mL of THF under argon. This was refluxed for 40 minutes. The reaction was quenched in 50 mL of ice water and extracted 3 times with 40 mL of methylene chloride. The organic layer was washed with brine for 10 minutes to dry it.

A solution of 50 mg of the alcohol 204 (0.01 mmol), 0.7 mL of thionyl chloride and 5 mL of toluene was refluxed for 1 hour. The excess thionyl chloride and toluene was removed under vacuum. Then toluene (10 mL) was added. This was removed again to flash evaporate all the thionyl chloride.

A slurry of 50 mg (~0.8 mmol) of KOH (80%) in 2 mL of DMSO was treated with 50 mg (0.13 mmol) of 204 and MeI (50 μL, 0.8 mmol). The reaction mixture was stirred at room temperature for 1 hour and then poured into 20 mL of ice-water. The aqueous phase was then extracted with EtOAc (3×20 mL). The organic layer was washed with brine and dried over Na$_2$SO$_4$.

To 5 mL of DMSO was added 100 mg of (85%, 1.5 mmol) KOH powder. After stirring for 5 minutes, 204 (146 mg, 0.4 mmol) was added and this was followed immediately by the addition of 70 μL of ICH$_2$CH$_3$ (0.87 mmol). The mixture was stirred until the starting material had disappeared by TLC. After 1 hour the reaction was quenched with ice-water. The aqueous phase was then extracted with EtOAc (3×20 mL). The organic layer was washed with brine and dried over Na$_2$SO$_4$.
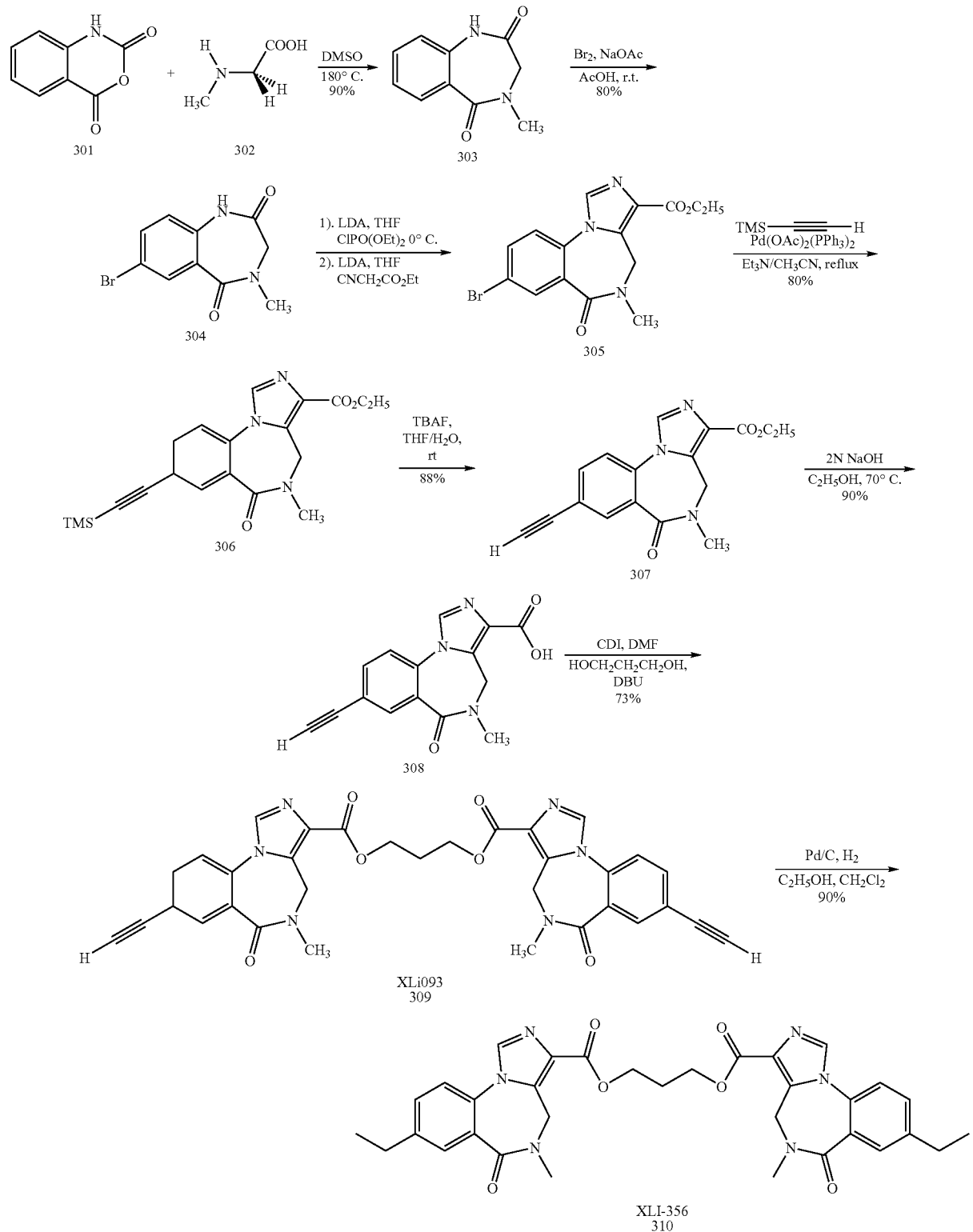

Isatoic anhydride 301 and sarcosine 302 were heated in DMSO, followed by bromination to provide the bromide 304. The conversion of bromide 304 into the imidazobenzodiazepine 305, followed the classic work of Fryer et al. of the Roche group. Fryer, R. I. S., R. A.; Sternbach, L. H., Quinazoines+1,4 Benzodiazepines. 17. Synthesis of 1,3-Dihydro-5-Pyridyl-2H-1,4-Benzodiazepine Derivatives. *Journal of Pharmaceutical Sciences* 1964, 53, 264-268; Fryer, R. I. Z., P.; Lln, K.-Y.; Upasani, R. B.; Wong, G.; Skolnick, P., Conformational Similarity of Diazepam-Sensitive and -Insensitive Benzodiazepine Receptors Determined by Chiral Pyrroloimidizobenzodiazepines. *Med. Chem. Res.* 1993, 3, 183-191; Fryer, R. I.; Gu, Z. Q.; Wang, C. G., zo[1,5-a][1,4] Benzodiazepines. *Journal of Heterocyclic C Synthesis of Novel, Substituted* 4h-Imida hemistry 1991, 28, (7), 1661-1669. This bromide was converted into 6 by a Heck-type coupling reaction and the silyl group was removed in high yield on treatment with TBAF/H$_2$O/THF. Liu, R. Y.; Hu, R. J.; Zhang, P. W.; Skolnick, P.; Cook, J. M., Synthesis and pharmacological properties of novel 8-substituted imidazobenzodiazepines: High-affinity, selective probes for alpha 5-containing GABA(A) receptors. *Journal of Medicinal Chemistry* 1996, 39, (9), 1928-1934; Skolnick, P.; Hu, R. J.; Cook, C. M.; Hurt, S. D.; Trometer, J. D.; Lu, R. Y.; Huang, Q.; Cook, J. M., [H-3]RY 80: A high-affinity, selective ligand for gamma-aminobutyric acid(A) receptors containing alpha-5 subunits. *Journal of Pharmacology and Experimental Therapeutics* 1997, 283, (2), 488-493.

Hydrolysis of the ester function of 307 provided the acid 308 in excellent yield and this material was subjected to a standard CDI mediated coupling reaction to furnish bivalent ligand 309 in 73. % yield. The dimer 309 (500 mg, 0.83 mmol) was dissolved in EtOH (150 mL) after which Pd/C (176 mg) was added in solution at rt. The slurry was stirred for 5 h under one atmosphere of H$_2$ (bench top, balloon of H$_2$). The catalyst was removed by filtration and washed with EtOH. The EtOH was removed under reduced pressure to furnish a residue. This material was purified by flash chromatography (silica gel, EtOAc: EtOH/8:2) to provide 310 (504 mg, 99%) as white crystals: mp 125-133° C.; IR (NaCl) 3407, 2964, 2358, 1725, 1640, 1499 cm$^{-1}$; $^1$H NMR (CDCl$_3$) δ 1.29 (m, 6H), 2.39(m, 21H), 2.78 (dd, 4H, J=7.5 Hz, 15.1 Hz), 3.26 (s, 6H), 4.48 (br, 2H), 4.56 (t, 4H, J=6.1 Hz, 12.2 Hz), 5.16(br, 2H), 7.33 (d, 2H, J=8.2 Hz), 7.48 (d, 2H, J=1.8 Hz), 7.89 (t, 4H, J=3.2 Hz, 5.3 Hz), 8.15; MS(EI) m/e (relative intensity) 611 (M$^+$+1, 100). Anal. Calcd for C$_{33}$H$_{34}$N$_6$O$_6$·2H$_2$O: C, 61.33; H, 5.92; N, 13.00. Found: C, 61.74; H, 5.91; N, 12.63.

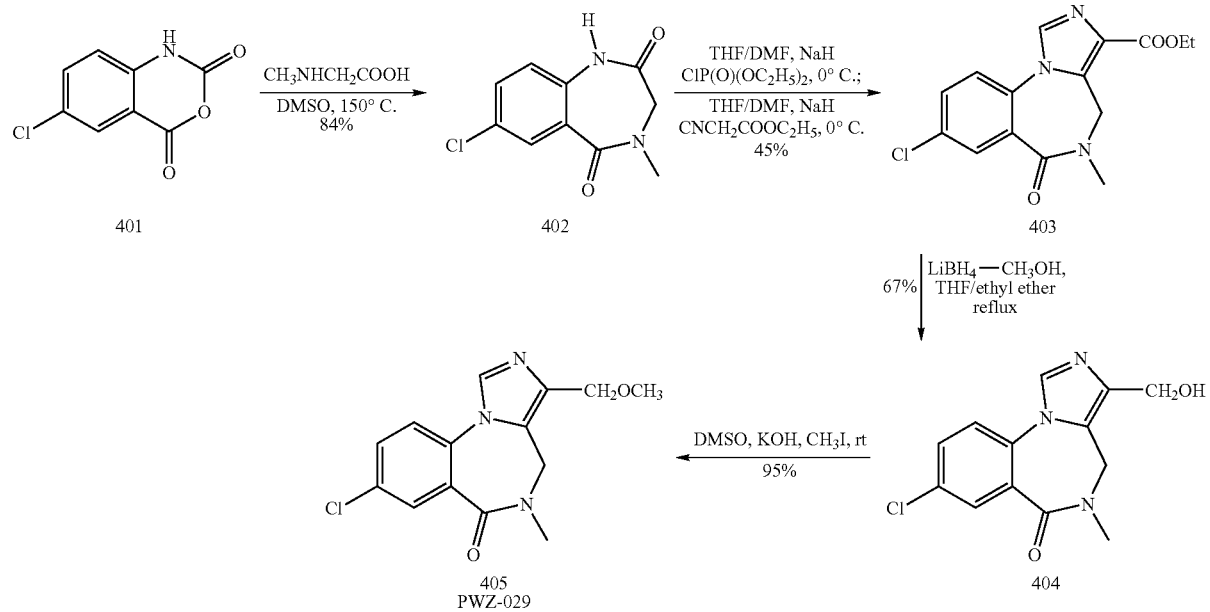

Synthetic Scheme for PWZ-029

7-Chloro-4-methyl-3,4-dihydro-1H-benzo[e][1,4]diazepine-2,5-dione (402). A mixture of 5-chloroisatoic anhydride 401 (20 g, 101 mmol) and sarcosine (9.02 g, 101 mmol) in DMSO (160 mL) was heated at 150° C. for 5 hr, cooled to room temperature and poured into ice water (750 mL) to furnish a light brown precipitate. This solid was collected by filtration, washed with water (3×200 mL) and dried. The benzodiazepine 402 was obtained as a light brown solid (19 g, 84% yield). This material was used directly in the next experiment.

Ethyl 8-chloro-5,6-dihydro-5-methyl-6-oxo-4H-imidazo[1,5-α][1,4]benzodiazepine-3-carboxylate (3). A solution of 402 (19.5 g, 86.8 mmol) in DMF (160 mL) and THF (240 mL) was cooled to 0° C. and sodium hydride (60% in mineral oil, 4.17 g, 104 mmol) was added to it in one portion. After 20 min, diethyl chlorophosphate (22.5 g, 130 mmol) was added dropwise and the solution was stirred continuously for 30 min with cooling in an ice bath. A solution of ethyl isocyanocetate (12.8 g, 112.8 mmol) and sodium hydride (60% in mineral oil, 5.43 g, 136 mmol) in DMF (130 mL), which had been stirred for 15 min at 0° C., was added to the above mixture. After stirring for another 30 min with cooling (0° C.), the reaction mixture was allowed to stir at room temperature overnight. Acetic acid was added to quench the reaction and it was then poured into ice water and extracted with ethyl acetate (3×300 mL). The combined extracts were washed with water (3×50 mL), brine (100 mL) and dried ($K_2CO_3$). The solvent was removed under reduced pressure and the residue was chromatographed on a wash column (silica gel) and then crystallized from ethyl acetate to give white crystals (12.5 g, 45% yield). mp 192-193° C.; $^1$H NMR ($CDCl_3$) δ 1.47 (t, 3H, J=7.12 Hz), 3.27 (s, 3H), 4.13 (br s, 1H), 4.46 (q, 2H, J=7.12 Hz), 5.23 (br s, 1H), 7.40 (d, 1H, J=8.6 Hz), 7.62 (dd, 1H, J=8.6, 2.5 Hz), 7.90 (s, 1H), 8.1 (d, 1H, J=2.4 Hz); MS (EI) m/e 319 (M+, 100). This material was used directly in the next experiment. See also: Gu, Z.-Q.; Wong, G.; Dominguez, C.; de Costa, B. R.; Rice, K. C.; Skolnick, P. Synthesis and Evaluation of Imidazo[1,5-a][1,4]benzodiazepine Esters with High Affinities and Selectivities at "Diazepam-Insensitive" Benzodiazepine Receptors. *J. Med. Chem.* 1993, 36, 1001-1006.

8-Chloro-5,6-dihydro-5-methyl-6-oxo-4H-imidazo[1,5-α][1,4]benzodiazepine-3-methyl alcohol (404). A solution of imidazobenzodiazepine 403 (5 g, 15.6 mmol) in a mixture of ethyl ether (50 mL), anhydrous $CH_3OH$ (2.5 mL), and THF (50 mL) was treated with $LiBH_4$ (2.0 M in THF, 9 mL, 18 mmol). The mixture which resulted was heated to reflux for 30 min, cooled to room temperature, and treated with saturated aqueous $NaHCO_3$ (5 mL). The solvent was then removed under pressure, and the residue was taken up in EtOAc (100 mL). The organic layer was washed with water (2×20 mL), brine (20 mL) and dried ($MgSO_4$). After removal of solvent under reduced pressure, the residue was purified by flash chromatography (silica gel, EtOAc) to afford alcohol 404 as colorless crystals (2.9 g, 67%): mp 252-253° C.; IR (KBr) 3500 (br, OH), 3100, 1667, 1612, 823 cm$^{-1}$; $^1$H NMR ($CDCl_3$) δ 3.20 (s, 3H), 4.40 (s, 2H), 4.70 (d, 2H, J=4.2 Hz), 7.30 (d, 1H, J=8.6 Hz), 7.55 (dd, 1H, J=8.7, 2.4 Hz), 7.80 (s, 1H), 8.00 (d, 1H, =2.4 Hz); MS (EI) m/e 279 (M+, 41), 277 (M$^+$, 100), 259 (84), 246 (55), 231 (41). The spectral data and melting point were in excellent agreement with the alcohol in Zhang, P.; Zhang, W.; Liu, R.; Harris, B.; Skolnick, P.; Cook, J. M. Synthesis of Novel Imidazobenzodiazepines as Probes of the Pharmacophore for "Diazepam-Insensitive" $GABA_A$ Receptors. *J. Med. Chem.* 1995, 38, 1679-1688. See also: Gu, Z. Q.; Wong, C.; Dominguez, C.; de Costa, B. R.; Rice, K. C.; Skolnick, P. Synthesis and Evaluation of Imidazo[1,5-a][1,4] benzodiazepine Esters with High Affinities and Selectivities at "Diazepam-Insensitive" Benzodiazepine Receptors. *J. Med. Chem.* 1993, 36, 1001-1006.

Methyl(8-chloro-5,6-dihydro-5-methyl-6-oxo-4H-imidazo[1,5-a][1,4]benzodiazepin-3-yl)methyl ether (405). To a slurry of KOH (100 mg, 1.6 mmol) in DMSO (2, mL) at room temperature were added alcohol 404 (108 mg, 0.4 mmol) and $CH_3I$ (50 mL, 0.8 mmol). The mixture which resulted was stirred for 5 min, poured into ice water (10 mL), and extracted with EtOAc (3×20 mL). The combined organic extracts were washed with brine (10 mL) and dried ($MgSO_4$). After removal of solvent under reduced pressure, the residue was purified by a wash column on silica gel (EtOAc) to give ether 405 as an off-white powder (110 mg, 95%): mp 193-194° C.; IR (KBr) 3122, 2973, 1632, 1611, 811 cm$^{-1}$; $^1$H NMR ($CDCl_3$) δ 3.18 (s, 3H), 3.42 (s, 3H), 4.38 (s, 2H), 4.55 (br, 2H), 7.30 (d, 1H, J=8.6 Hz), 7.55 (dd, 1H, J=8.7, 2.5 Hz), 7.80 (s, 1H), 8.00 (d, 1H, J=2.4 Hz). The spectral data and melting point were in excellent agreement with that of 405 reported in Zhang, P.; Zhang, W.; Liu, R.; Harris, B.; Skolnick, P.; Cook, J. M. Synthesis of Novel Imidazobenzodiazepines as Probes of the Pharmacophore for "Diazepam-Insensitive" $GABA_A$ Receptors. *J. Med. Chem.* 1995, 38, 1679-1688.

Experimental Methods

Experiments as described below by Sieghart and Fürtmueller for compound RY024 were conducted for certain compounds of this invention such as compounds PWZ-029 and XLI356:

Experimental Procedures for Two-Electrode Voltage Clamp:

Effects of RY024 on $GABA_A$ receptors were tested by two-electrode voltage clamp experiments in cRNA injected *Xenopus* oocytes that functionally expressed several subtype combinations of $GABA_A$ receptors.

Preparation of Cloned mRNA:

Cloning of $GABA_A$ receptor subunits α1, β3 and γ2 into pCDM8 expression vectors (Invitrogen, CA) has been described elsewhere. Fuchs, K.; Zezula, J.; Slany, A.; Sieghart, W. Endogenous [$^3$H]flunitrazepam binding in human embryonic kidney cell line 293. *Eur J Pharmacol* 995, 289, 87-95. $GABA_A$ receptor subunit α4 was cloned in an analogous way. cDNAs for subunits α2, α3 and α5 were gifts from P. Malherbe and were subcloned into pCl-vector. cDNA for subunit α6 was a gift from P. Seeburg and was subcloned into the vector pGEM-3Z (Promega). After linearizing the cDNA vectors with appropriate restriction endonucleases, capped transcripts were produced using the mMessage mMachine T7 transcription kit (Ambion, TX). The capped transcripts were polyadenylated using yeast poly(A) polymerase (USB, OH) and were diluted and stored in diethylpyrocarbonate-treated water at −70° C.

Functional Expression of $GABA_A$ Receptors:

The methods used for isolating, culturing, injecting and defolliculating of the oocytes were identical with those described by E. Sigel. Sigel, E. Properties of single sodium channels translated by *Xenopus* oocytes after injection with messenger ribonucleic acid. *J Physiol* 987, 386, 73-90; Sigel, E.; Baur, R.; Trube, G.; Mohler, H.; Malherbe, P. The effect of subunit composition of rat brain $GABA_A$ receptors on channel function. *Neuron* 1990, 5, 703-711. Mature female *Xenopus laevis* (Nasco, Wis.) were anaesthetized in a bath of ice-cold 0.17% Tricain (Ethyl-m-aminobenzoat, Sigma, MO) before decapitation and removal of the frogs ovary. Stage 5 to 6 oocytes with the follicle cell layer around them were singled out of the ovary using a platinum wire loop. Oocytes were stored and incubated at 18° C. in modified Barths' Medium (MB, containing 88 mM NaCl, 10 mM HEPES-NaOH (pH 7.4), 2.4 mM $NaHCO_3$, 1 mM KCl, 0.82 mM $MgSO_4$, 0.41 mM $CaCl_2$, 0.34 mM $Ca(NO_3)_2$) that was supplemented with 100 U/ml penicillin and 100 μg/ml streptomycin. Oocytes with follicle cell layers still around them were injected with 50 nl of an aqueous solution of cRNA. This solution contained the transcripts for the different alpha subunits and the beta 3 subunit at a concentration of 0.0065 ng/nl as well as the transcript for the gamma 2 subunit at 0.032 ng/nl. After injection of cRNA, oocytes were incubated for at least 36 hours before the enveloping follicle cell layers were removed. To this end, oocytes were incubated for 20 min at 37° C. in MB that contained 1 mg/ml collagenase type IA and 0.1 mg/ml trypsin inhibitor I-S (both Sigma). This was followed by osmotic shrinkage of the oocytes in doubly concentrated MB medium supplied with 4 mM Na-EGTA. Finally, the oocytes were transferred to a culture dish containing MB and were gently pushed away from the follicle cell layer which stuck to the surface of the dish. After removing of the follicle cell layer, oocytes were allowed to recover for at least four hours before being used in electrophysiological experiments.

Electrophysiological Experiments:

For electrophysiological recordings, oocytes were placed on a nylon-grid in a bath of *Xenopus* Ringer solution (XR, containing 90 mM NaCl, 5 mM HEPES-NaOH (pH 7.4), 1 mM $MgCl_2$, 1 mM KCl and 1 mM $CaCl_2$) The oocytes were constantly washed by a flow of 6 ml/min XR which could be switched to XR containing GABA and/or drugs. Drugs were diluted into XR from DMSO-solutions resulting in a final concentration of 0.1% DMSO perfusing the oocytes. Drugs were preapplied for 30 sec before the addition of GABA, which was coapplied with the drugs until a peak response was observed. Between two applications, oocytes were washed in XR for up to 15 min to ensure full recovery from desensitization. For current measurements the oocytes were impaled with two microelectrodes (2-3 ma) which were filled with 2 mM KCl. All recordings were performed at room temperature at a holding potential of −60 mV using a Warner OC-725C two-electrode voltage clamp (Warner Instruments, Hamden, Conn.) or a Dagan CA-1B Oocyte Clamp (Dagan Corporation, Minneapolis, Minn.). Data were digitised, recorded and measured using a Digidata 1322A data acquisition system (Axon Instruments, Union City, Calif.). Results of concentration response experiments were fitted using GraphPad Prism 3.00 (GraphPad Software, San Diego, Calif.). The equation used for fitting concentration response curves was $Y=Bottom+(Top-Bottom)/(1+10^{\wedge}(X-LogEC50))$; X represents the logarithm of concentration, Y represents the response; Y starts at Bottom and goes to Top with a sigmoid shape.

Effects of RY024 on Chloride Currents in $GABA_A$ Receptors

Effects of RY024 on $GABA_A$ receptors were characterized using *Xenopus* oocytes expressing the $GABA_A$ receptor subunits alpha 1 to alpha 6 in combination with beta 3 and gamma 2 subunits. Using the two electrode voltage clamp method, currents in the μA range were measured for all subunit combinations in response to application of a saturating concentration of GABA (10 mM). Two electrode voltage clamp experiments were performed to test whether RY024 triggered chloride currents, modulated GABA-induced currents or antagonized the effects of benzodiazepines in oocytes that express $GABA_A$ receptors.

RY024 at concentrations up to 1 μM did not trigger chloride currents in any of the tested subtypes of the $GABA_A$ receptor. At nanomolar concentrations, RY024 modulated GABA-induced currents in an alpha subtype specific manner. To test for agonistic or inverse agonistic effects, the compound was coapplied with a concentration of GABA that induced app. 20% of the maximum current amplitude.

In $GABA_A$ receptors containing the α1, α2 and α5 subunits nanomolar concentrations of RY024 reduced GABA elicited currents in a concentration dependent manner. $EC_{50}$ for this effect was app. 10 fold lower for α5 containing receptors than for those containing α1 and α2 (Table III).

In α3 containing receptors no apparent modulation of GABA elicited currents by RY024 was seen. However, in these receptors 1 μM RY024 reduced the stimulation by 30 nM Diazepam (284.8 t 48.7% at GABA $EC_3$) by 96.3±4.7%.

In $GABA_A$ receptors that contain $α_4$ and $α_6$ high nanomolar concentrations of RY024 weakly stimulated GABA elicited currents (Table III).

Due to limited concentration range, maximum modulation of GABA elicited currents by RY024 was estimated by extrapolation (curve-fit by GraphPad Prism) (Table III). Estimated maximum effect was dependent on the alpha-subunit, with the α5 subunit showing bigger maximum effect than α1 and α2 (−40.4±0.8%, −31.0±2.5% and −20.7±1.2%, respectively). In α3 containing receptors, despite obvious binding of the compound (inhibition of diazepam) virtually no effect was seen (−3.3±2.1%).

Figures 27, 28, 28B:
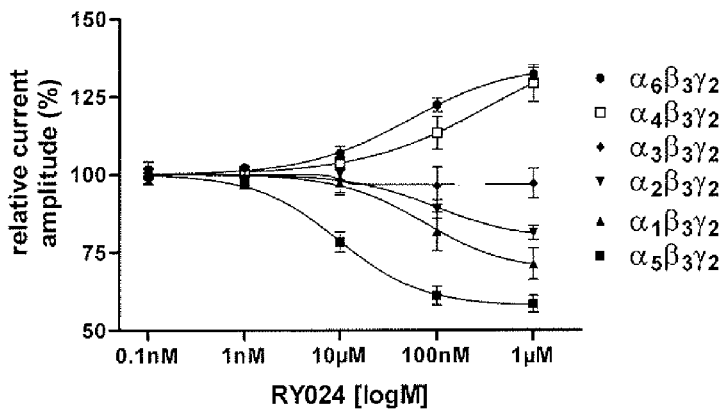
FIG. 27 depicts dose response curves for RY024 in oocytes expressing different subunit combinations of $GABA_A$ receptors.
FIGS. 28 A and B provide a full panel Receptor data for certain compounds of the invention. Data on the full panel (secondary binding) are Ki values. The Ki values are reported in nanomolar concentrations, In the Full panel data various receptors were used, including 5ht1a, 5ht1b, 5ht1d, 5ht1e, 5ht2a, 5ht2b, 5ht2c, 5ht3, 5ht5a, 5ht6, 5ht7, α1A, α1B, α2A, α2B, α2C, β1, β2, CB1, CB2, D1, D2, D3, D4, D5, DAT, DOR, H1, H2, H3, H4, imidazoline 1, KOR, M1, M2, M3, M4, M5, MDR1, MOR, NET, NMDA, SERT, σ1, and σ2. 5-HT receptors, 5ht1a, 5ht1b, 5ht1d, 5ht1e, 5ht2a, 5ht2b, 5ht2c, 5ht3, 5ht5a, 5ht6, 5ht7, are receptors for the neurotransmitter and peripheral signal mediator serotonin, also known as 5-hydroxytryptamine or 5-HT. α1A, α1B, α2A, α2B, α2C, β1, β2; CB1, CB2 are adrenoceptors; cannabinoid receptors, D1, D2, D3, D4, D5 are dopamine receptors; DAT is dopamine transporter receptor; DOR is δ-Opioid receptor; H1, H2, H3, H4 are histamine receptors; KOR is κ-Opioid receptor; M1, M2, M3, M4, M5 are muscarinic acetylcholine receptors; MDR represents multidrug resistance in the course of exposure to various compounds that are used in modern anticancer therapy, including cytotoxic drugs and differentiating agents. Thus mechanisms that regulate the MDR1 overexpression can prevent the emergence of MDR in tumor cells that expressed null-to-low levels of MDR1 mRNA or P-glycoprotein prior to treatment. MOR- represents µ-opioid receptors; NET represents norepinephrine transporter receptors; NMDA is an ionotropic receptor for glutamate (NMDA is a name of its selective specific agonist), SERT represents serotonin receptors; σ1, and σ2 represents sigma opioid receptors.
Figure 29:
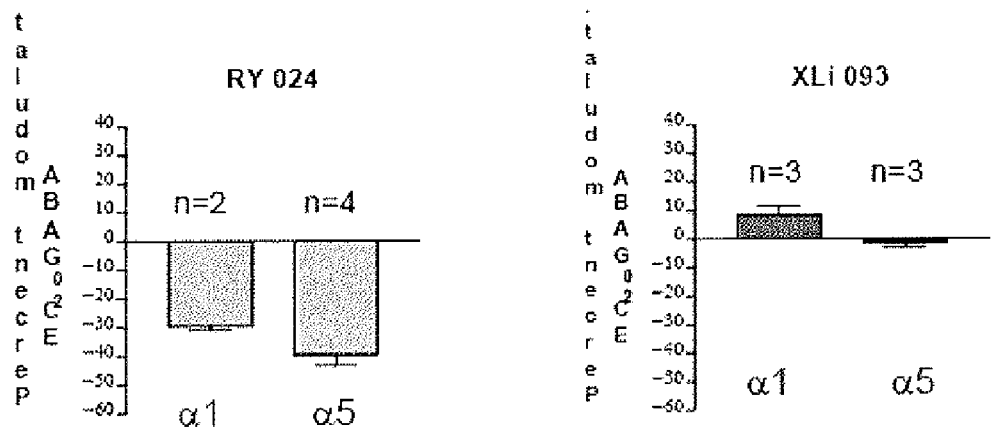
FIG. 29 provides efficacy of RY 024 and XLi 093: in this figure, modulation of GABA currents (EC20) by RY 024 and XLi 093 in performed in *Xenopus* oocytes. Subtype combinations are indicated in the graph, only rat subunits were used. Cells were individually titrated to EC20, (2-5 µM for 2γ3β5α and 10-20 µM for 2γ3β1α respectively). GABA modulators were preapplied for 30 sec before the addition of GABA, which was co-applied with the drug until a peak response was observed. Drugs were made up and diluted as stock solutions in DMSO. Final concentrations of DMSO perfusing the oocyte was 0.1%. Values are shown as mean±SD.
Figure 30:
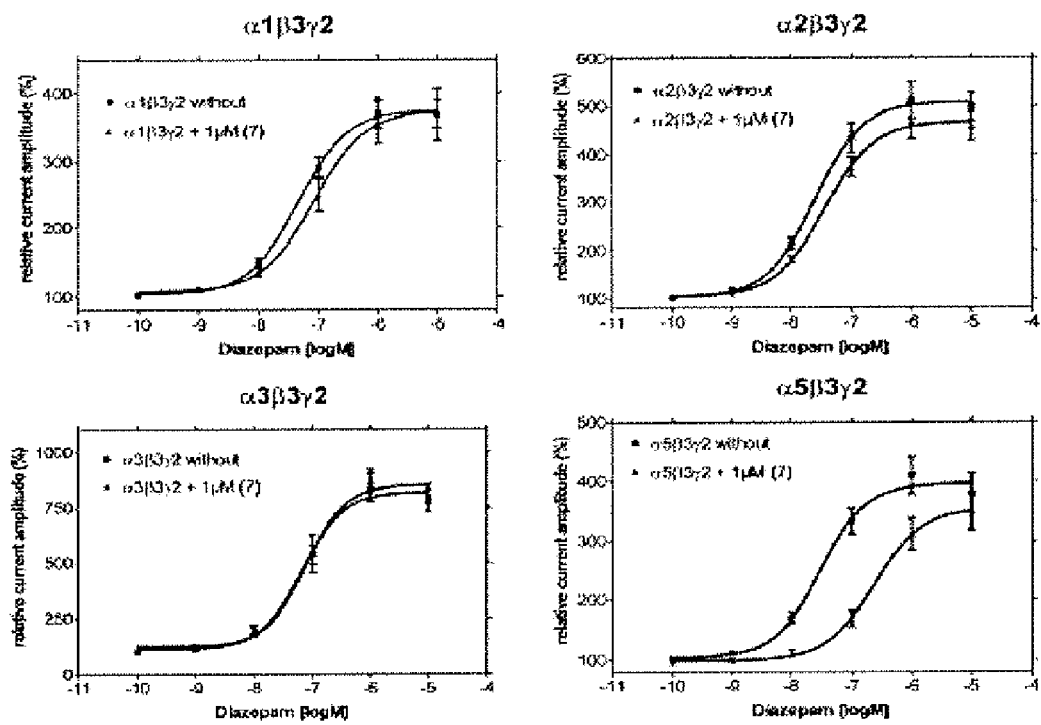
FIG. 30 provides data related to dose-response curve for compound Xli093 at α5. In oocytes expressing GABAA receptors of the subtypes α1β3γ2, α2β3γ2, or α3β3γ2, and α5β3γ2, 1 µM XLi093 caused only marginal shifts of dose response curves for the stimulation of GABA-induced currents by diazepam. In oocytes expressing GABAA receptors of subunit combination α5β3γ2, the presence of 1 µM XLi093 shifted the dose-response curve for the stimulation of GABA-induced currents by diazepam to the right. Even high concentrations of diazepam could not fully overcome this inhibition since maximum current stimulations in the presence of XLi093 reached only approximately 85% of current stimulations that were seen in the absence of XLi093.

FIG. 27 depicts dose response curves for RY024 in oocytes expressing different subunit combinations of $GABA_A$ receptors. Subtype combinations are indicated in legends. cRNA-injected *Xenopus* oocytes were held at −60 mV under two-electrode voltage clamp. Increasing concentrations of RY024 were superfused together with a GABA concentration eliciting app. 20% of the maximal current amplitude. RY024 was preapplied for 30 sec before the addition of GABA, which was coapplied with the drugs until a peak response was observed. Data were normalized for each curve assuming 100% for the response in the absence of RY024. RY024 was made up and diluted as stock solution in DMSO. Final concentrations of DMSO perfusing the oocyte were 0.1%. Values are presented as mean±SD of at least four oocytes from at least two batches.

TABLE III

Concentration-response data for modulation of control GABA $EC_{20}$ by RY024 in different $GABA_A$ receptor subtypes

| Subtype | EC50 μM (95% confidence interval) | Estimated maximum modulation ± SD * | Number of oocytes |
|---|---|---|---|
| α1β3γ2 | 74.4 μM (38.3-144.3) | −31.0 ± 2.5% | 5 |
| α2β3γ2 | 95.5 μM (59.4-153.6) | −20.7 ± 1.2% | 7 |
| α3β3γ2 |  | −3.3 ± 2.1% | 5 |
| α4β3γ2 | 324.4 μM (22.6-4651.5) | +43.0 ± 15.9 | 8 |
| α5β3γ2 | 9.8 μM (8.1-11.9) | −40.4 ± 0.8% | 8 |
| α6β3γ2 | 51.7 μM (35.8-74.6) | +35.2 ± 1.5% | 7 |

* estimated by curve-fit (GraphPad Prism)

Further, animal data for FIGS. 22-26 were obtained using experimental methodologies described in a previously published reference, Influence of benzodiazepine binding site ligands on fear-conditioned contextual memory *European journal of Pharmacology*, Volume 426, Issues 1-2, 24 Aug. 2001, Pages 45-54, Timothy M. DeLorey, Richard C. Lin, Brian McBrady, Xiaohui He, James M. Cook, Jelveh Lameh and Gilda H. Loew, which is incorporated by reference as if fully set forth here in its entirety. Selected sections of the reference are provided below:

Animals

Male C57B1/6 mice were obtained from Charles Rivers Laboratories (Holister, Calif.) at 6 weeks of age. Mice used in fear conditioning were between 7 and 12 weeks of age. Animals were housed eight to a cage in rooms with a normal 12-h light/12-h dark cycle (lights on 700-1900 h) with free access to food and water. Tests were conducted during the light phase between 1300 and 1700 h with a 20-min acclimation period in the testing room prior to drug or vehicle administration. All animal protocols used in this study conform to the guidelines determined by the National Institute of Health (USA) Office for Protection from Research Risks and are approved by the Animal Care and Use Committee of the Palo Alto Veterans Administration Medical Center, Palo, Alto, Calif. (USA).

Drugs/Compounds

Compounds used in this study include the benzodiazepine binding site ligands Ro15-4513 (ethyl 8-azido-6-dihydro-5-methyl-6 oxo-4H-imidazo[1,5-a]-[1,4]benzodiazepine-3-carobxylate), DMCM (methyl 6,7-dimethoxy-4-ethyl-beta-carboline-3-carboxylate), flunitrazepam (1,3-dihydro-5-(o-fluorophenyl)-1-methyl-7-nitro-2H-1,4-benzodiazepine-2-one) from RBI, Natick, Mass., Ro23-1590(2-(p-chloro phenyl)-4-(4-N-ethylamide piperazinyl) quinoline), Ro15-1788 (8-fluoro-3-carboxy-5,6-dihydro-5-methyl-6-oxo-414- imidazo[1,5a]1,4 benzodiazepine) from Hoffman-LaRoche, Nutley, N.J.; ZK-93426 (ethyl-S-isopropyl-4-methyl-beta-carboline-3-carboxylate) from Schering, Berlin; βCCT (β-carboline-3-carboxylate-tbutyl ester), Compound #47 (Ethyl 8-trimethylsilyl-2-accetyl-12,12a-dihydro-9-oxo-9H, 11H-azeto[2,1-c]imidazo[1,5-a]1,4 benzodiazepine 1 carboxylate) and RY10 (Ethyl 8-Ethyl-5,6-dihydro-5-methyl-6-oxo-4H-imidazo[1,5a][1,4]benzodiazepine-3-carboxylate), Xli093(1,3-Bis(8-acetyleno-5,6-dihydro-5-methyl-6-oxo-4H-imidazo[1,5a][1,4]-benzodiaze-pine-3-carboxy)propyl diester), Xli356(1,3-Bis(8-ethyl-5,6-dihydro-5-methyl-6-oxo-4H-imidazo[1,5a][1,4]benzodiazepine-3-carboxy)propyl diester), PWZ-029(methyl(8-chloro-5,6-dihydro-5-methyl-6-oxo-4H-imidazo[1,5-α][1,4]benzodiazepin-3-yl) methyl ether) were provided by Dr. James Cook at the Univ. of Wisconsin-Milwaukee. Also used were the cholinergic receptor antagonists (−)-scopolamine hydrobromide (α-(hydroxymethyl)benzeneacetic acid 9-methyl-3-oxa-9-azatricyclo[3.3.1.0$^{2,4}$]non-7-yl ester hydrobromide and (−)-methylscopolamine bromide (7-(3-hydroxy-1-oxo-2-phenylpropoxy)-9,9-dimethyl-3-oxa-9 azoniatrricyclo-[3.3.1.0$^{2,4}$]nonane bromide from RBI, Natick, Mass. All drugs were suspended in vehicle (0.9% saline containing 0.2% Tween 80).

Binding Studies

Frozen rat whole brain (Pel Freeze, Rogers, A R), approximate weight 1 g, was homogenized with a polytron homogenizer in 20 ml of 50 mM Tris-HCl, pH 7.4 at 4° C. and centrifuged at 20,000×g for 10 min. The supernatant was discarded and the pellet homogenized and centrifuged twice as above. The pellet was resuspended in 5 ml of buffer and frozen at −86° C. overnight. After thawing, the volume of homogenate was restored to the original 20 ml with buffer and washed two more times by centrifugation and rehomogenization. The final membrane pellet was resuspended to a tissue concentration of 100 mg wet weight/ml of buffer and stored in aliquots at −86° C. until used. For binding assays, membranes (30-50 µg/tube) were incubated with 0.3 nM [$^3$H]N-methylscopolamine (Amersham Pharmacia Biotech., Piscataway, N.J.) and either 10 nM or 10 µM of the unlabeled ligand in a total of 1 ml reaction volume in Tris-HCl, pH 7.4. Incubation was at room temperature for 60 min. The assay was terminated by rapid filtration through Whatman GF/B filters using a FilterMate cell harvester (Packard Instruments, Meriden, Conn. followed by three washes, 4 ml each of ice cold Tris-HCl, pH 7.4 buffer, Radioactivity retained on the filters was measured using Microscint O in a TopCount liquid scintillation counter (Packard Instruments, Meriden, Conn.). All assays were carried out in triplicate.

Spontaneous Locomotive Activity

Mice were allowed to acclimate to the test room for 30 min prior to drug injection. Thirty minutes after receiving an intraperitoneal(i.p.) injection of drug or vehicle, mice were placed individually into clear plastic monitoring chambers measuring 72×32×32 cm each. Spontaneous locomotor activity was measured via seven sets of photoelectric sensors evenly spaced along the length of the monitoring chamber, 4 cm above the floor of the chamber (San Diego Instruments, San Diego, Calif.). Total activity was recorded in arbitrary units reflective of the number of times a mouse interrupts the photoelectric sensors during a 10-min monitoring session. This data was automatically recorded and stored by computer. Compounds that did not significantly affect spontaneous locomotor activity either by reducing activity(agonist.or enhancing activity(inverse agonist), relative to vehicle, at concentrations ≦30 mg/kg were also tested for antagonism. Antagonism was determined by assessing spontaneous locomotor activity 30 min after simultaneous i.p. injection of both the putative antagonist and the agonist flunitrazepam(5 mg/kg). Results were compared both to the effects of flunitrazepam alone and the vehicle control. Data were analyzed with one-way analysis of variance(ANOVA) using GraphPad PRISM 2.01 program (GraphPad Software, San Diego, Calif.). Separate treatment effects between groups were analyzed using the appropriate post hoc comparison.

Pavlovian Fear Conditioning

Before testing each day, the mice were moved to a holding room and allowed to acclimate for at least 30 min. Each mouse received an i.p. injection of one of the following: vehicle, benzodiazepine binding site ligand (2-30 mg/kg), scopolamine (1 mg/kg), methylscopolamine (1 mg/kg) or scopolamine (1 mg/kg) combined with one of the benzodiazepine binding site ligands (2-30 mg/kg). The dose level chosen for each compound was one that neither elicited convulsions nor impaired locomotion. Twenty minutes after injection, the mice were placed individually in one of four identical experimental chambers (Med Associates, St. Albans, Vt.) that had been scented with 0.3% ammonium hydroxide solution before testing. Chambers were back-lit with fluorescent light with a white noise generator providing 70 dB of background noise. After 4 min in the chamber, mice were exposed to a loud tone (85 dB, 2.9 kHz) for 32 s with the last 2 s coupled with a 0.5-mA "scrambled footshock". This procedure was repeated for a total of three episodes with a 1-min period separating each episode. One minute after the final footshock, the mice were returned to their home cages. Twenty-four hours later, contextual memory was assessed by placing the mice back into the freshly rescented (0.3% Ammonium hydroxide) conditioning chambers in which they were trained, for a 4-min test period in the absence of footshock. Conditioned fear to the context was assessed by measuring the freezing response according to the methods of Fanselow and Bolles (1979). Freezing was defined as the absence of all visible movements of the body and vibrissae aside from those necessitated by respiration. An observer, blind to the drug(s) used, scored each mouse every 8 s, for a total of 4 min, for presence or absence of freezing. These data were transformed to a percentage of total observations. Data were analyzed by one-way analysis of variance(ANOVA) using GraphPad PRISM 2.01 (GraphPad Software). Separate treatment effects between groups were analyzed post hoc using Dunnett's or Bonferroni's multiple comparisons.

Further, biological data accumulated during the experiments described above are provided in various figures, FIGS. 12-30. As shown in these Figures, certain compounds of the invention such as DM-I-81, PWZ029 and XLI-356 appear to be lead important compounds with desirable properties. These compounds were also found to have desirable properties as shown in FIG. 28, which includes a full panel screening of these compounds for various receptors.

| Structure | Code | MW | α1 | α2 |
|---|---|---|---|---|
| (structure) | Xli356 | 610.66 | 2383 | 5980 |
| (structure) | DM-I-81 | 407.46 | 2000 | 2000 |
| (structure) | PWZ-029 | 291.73 | >300 | >300 |

| Structure | α3 | α4 | α5 | α6 |
|---|---|---|---|---|
| (structure) | ND | 5000 | 107 | 5000 |
| (structure) | 2000 | 2000 | 176 | 2000 |

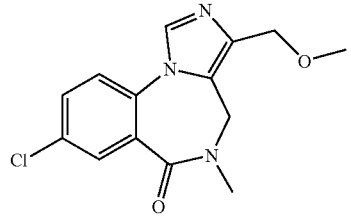

|       |    |      |      |
|-------|----|------|------|
| >300  | ND | 38.8 | >300 |

As described in these FIGS., 12-30, the discovery of α5 subtype specific inverse agonists will provide therapeutic agents to treat age-associated memory impairment and senile dementia of the Alzheimer's type. Substructure as well as activity searches provide guidance for building these selective molecules and help to guide future drug design process. This rational approach has led to several compounds with subtype selectivity. The three α5 subtype selective compounds which will act as lead compounds in future research are Xli093, DM-I-81, and PWZ-029. Full panel receptor binding Dimers Xli093 and Xli356 were done and the data appears to suggest that these compounds do not bind to other receptors at levels of concern. Xli356 and PWZ-029 were found to reverse scopolamine induced memory deficits in mice. (FIG. 28) When Xli356 was looked at in audio cued fear conditioning, the results show no activity. This suggests that the effects of Xli356 are selective through α5 receptors located in the hippocampus, which is highly associated with contextual memory. Audio cued memory instead is amygdala based, and is not affected by an α5 selective compounds. A series of analogs and dimers based on the α5 subtype selectivity of Xli356, PWZ-029, and DM-I-81 have been proposed. These targets have been checked in the α5 subtype pharmacophore/receptor model and should bind only to α5 receptors. In this fashion, inventors believe that potent α5 selective inverse agonists, antagonists, and agonists will be found that will lead to cognition and amnesia study in the hippocampus. Synthesis and pharmacological evaluation of these subtype selective agents will permit the assignment of the correct physiological functions to α5 subtypes. A potential therapeutic agent to improve memory and learning will result from this research.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof. All references cited hereinabove and/or listed below are hereby expressly incorporated by reference.

REFERENCES

Abe, K.; Takeyama, C.; Yoshimura, K. (1998) Effects of S-8510, A Novel Benzodiazepine Receptor Partial Inverse Agonist on Basal Forebrain Lesioning-Induced Dysfunction in Rats. Eur. J. Pharm., 24, 145-152.

Anger, W. K. (1991) Animal Test Systems to Study Behavioral Dysfunctions of Neurodegenerative Disorders. Neurotoxicology, 12, 403-13.

Bailey, D.; Tetzlaff, J.; Cook, J. M.; He, X.; Helmstetter, F. (2002) Effects of Hippocampal Injections of a Novel Ligand Selective for the a5b3 g2 Subunits of the GABA/Benzodiazepine Receptor on Pavlovian Conditioning. Neurobiology of Learning and Memory, 58, 1-10.

Chambers, M.; Atack, J.; Bromidge, F.; Broughton, H.; Cook, S.; Dawson, G.; Hobbs, S.; Maubach, K.; Reeve, A.; Seabrook, G.; Wafford, K.; MacLeod, A. (2002) 6,7-Dihydro-2-benzothiophen-4(5H)-ones: A Novel Class of $GABA_A$ α5 Receptor Inverse Agonists. J. Med. Chem., 45, 1176-1179.

Chambers, M. S.; Atack, J. R.; Broughton, H. B.; Collinson, N.; Cook, S.; Dawson, G. R.; Hobbs, S. C.; Marshall, G.; Maubach, K. A.; Pillai, G. V.; Reeve, A. J.; MacLeod, A. M. (2003) Identification of a Novel, Selective $GABA_A$ α5 Receptor Inverse Agonist Which Enhances Cognition. J. Med. Chem., 46, 2227-2240.

CIA World Factbook (2002) Series Editor city.

Costa, E.; Guidotti, A. (1996) Benzodiazepines on Trial: A Research Strategy for Their Rehabilitation. Trends. Pharmacol. Sci., 17, 192-200.

Crestani, F.; Keist, R.; Fritschy, J.-M.; Benke, D.; Vogt, K.; Prut, L.; Bluthmann, H.; Möhler, H.; Rudolph, U. (2002) Trace Fear Conditioning Involves Hippocampal Alpha 5 GABA(A) Receptors. Proc. Natl. Acad. Sci., 99, 8980-8985.

DeLorey, T.; Lin, R.; McBrady, B.; He, X.; Cook, J. M.; Lameh, J.; Loew, G. (2001) Influence of Benzodiazepine Binding Site Ligands on Fear-Conditioned Contextual Memory, Eur. J. Pharm., 426, 45-54.

Duka, T.; Dorrow, R. (1995) Benzodiazepine Receptor Inverse Agonists, Sarter M., Nutt D J and Lister R G eds., Wiley-Liss: New York.

Ebly, E.; Parhad, I.; Hogan, D.; Fung, T. (1994) Prevalence and Types of Dementia in the Very Old-Results from the Canadian Study of Health and Aging. Neurology, 44, 1593-1600.

Ernst, R. L.; J. W. Hay, C. Fenn, J. Tinklenberg and J. A. Yesavage (1997) Cognitive Function and the Costs of Alzheimer's Disease. An Exploratory Study. Arch. Neurol., 54, 687-93.

Evans, M. S.; Viola-McCabe, K. (1996) Midazolam Inhibits Long-Term Potentiation Through Modulation of GABA (A) Receptors. Neuropharmacol., 35, 347-357.

Flood, J. F.; Harris, F.; Morley, J. (1996) Age-related Changes in Hippocampal Drug Facilitation of Memory Processing in SAMP8 Mice. Neurobiol Aging, 17, 15-24.

Forster, M. J.; Prather, P. L.; Patel, S. R.; LAL, H. (1995) The Benzodiazepine Receptor Inverse Agonist RO 15-3505 Reverses Recent Memory Deficits in Aged Mice. Pharmacol. Biochem. Behav., 51, 557-60.

Froestl, W. (2004) Introduction to Receptors in Aging Diseases: GABAA Receptors. Med. Chem. Res., 13, 99-102.

Gu Q, Wang G, Dominguez C, Costa B R, Rice K C, Skolnick P (1993) Synthesis and evaluation of imidazo[1,5-a][1,4]-benzodiazepine esters with high affinities and selectivities at diazepam insensitive (DI) ben-zodiazepine receptors. J Med Chem 36: 1001-1006.

Howell, O.; Atack, J.; Dewar, D.; McKanan, R.; Sur, C. (2000) Density and pharmacology of alpha 5 subunit-containing GABAA receptors are preserved in hippocampus of Alzheimer's disease patients, Neuroscience, 98, 669-675.

Katzman R, Fox P J. (1999) The world-wide impact of dementia: Projections of prevalence and costs. In Mayeux R, Christen Y, eds: Epidemiology of Alzheimer's Disease: From Gene to Prevention. Heidelberg, Germany: Springer-Verlag: 1-17.

Kawasaki, K.; Eigyo, M.; Ikeda, M.; Kihara, T.; Koike, K.; Matsushita, A.; Murata, S.; Shiomi, T.; Takada, S.; Yasui, M. (1996) A Novel Benzodiazepine Inverse Agonist, S-8510, as a Cognitive Enhancer. Prog. Neuropsychopharmacol. Biol. Psychiatry, 20, 1413-25.

Li, X.; Cao, H.; Zhang, C.; Furtmueller, R.; Fuchs, K.; Huck, S.; Sieghart, W.; Deschamps, J.; Cook, J. M. (2003) Synthesis, in Vitro Affinity and Efficacy of a Bis-8-Ethynyl-4H-imidazo[1,5a]-1,4-benzodiazepine Analogue, The First Bivalent Alpha 5 Subtype Selective BzR/GABAA Antagonist. J. Med. Chem., 46, 5567-5570.

Li, X., (2004) PhD Thesis, University of Wisconsin-Milwaukee.

Lowe, S. L.; Francis, P. T.; Procter, A. W.; Palmer, A. M.; Davison, A. N.; Bowen, D. M. (1988) Gamma-aminobutyric Acid Concentration in Brain Tissue at Two Stages of Alzheimer's Disease. Brain, 111, 785-99.

Meyer, M.; Koeppe, R. A.; Frey, K. A.; Foster, N. L.; Kuhl, P. E. (1995) Positron Emission Tomography Measures of Benzodiazepine Binding in Alzheimer's Disease. Arch. Neurol., 52, 314-7.

Mizukami, K.; Ikonomovic, M. D.; Crayson, D. R.; Rubin, R. T.; Warde, D.; Sheffield, R.; Hamilton, R. L.; Davies, P.; Armstrong, D. M. (1997) Immunohistochemical study of GABA(A) receptor beta ⅔ subunits in the hippocampal formation of aged brains with Alzheimer-related neuropathologic changes. Exp. Neurology, 147, 333-45.

Möhler, H.; Fritschy, J.-M.; Crestani, F.; Hensch, T.; Rudolph, U. (2004) Specific GABA(A) Circuits in Brain Development and Therapy. Biochem. Pharmacol., 68, 1685-90.

Nagga, K.; Bogdanovic, N.; Marcusson, J. (1999) GABA Transporters (GAT-1) in Alzheimer's Disease. J. Neural. Transm., 106, 1141-9.

Perry, E.; Johnson, M.; Kerwin, J.; Piggott, M.; Court, J.; Shaw, P.; Ince, P.; Brown, A.; Perry, R. (1992) Convergent Cholinergic Activities in Aging and Alzheimer's Disease. Neurobiol Aging, 13, 393-400.

Potier, M. C.; Decarvalho, L. P.; Dodd, R. H.; Besselievre, R.; Rossier, J. (1988) In Vivo Binding of Beta-carbolines in Mice: Regional Differences and Correlation of Occupancy to Pharmacological Effects. Mol. Pharmacol., 34, 124-8.

Quirk, K.; Blurton, P.; Fletcher, S.; Leeson, P.; Tang, F.; Mellilo, D.; Ragan, C. I.; McKernan, R. M. (1996) [H-3]L-655,708, a novel ligand selective for the benzodiazepine site of GABA(A) receptors which contain the alpha 5 subunit, Neuropharmacol., 35, 1331-1335.

Sarter, M.; Bruno, J. (1997) Trans-Synaptic Stimulation of Cortical Acetylcholine and Enhancement of Attentional Functions: A Rational Approach for the Development of Cognition Enhancers. Behavioral Brain Research, 83, 7-14.

Sarter, M.; Bruno, J. (1994) Congnitive Functions of Cortical ACh: Lessons from Studies on Trans-Synaptic Modulation of Activated Efflux. Trends Neuroscience, 17, 217-21.

Seabrook, G. R.; Bowery, B.; Heavens, R.; Brown, N.; Ford, H.; Sirinathsinghi, D. J. S.; Borkowski, J. A.; Hess, J. F.; Strader, C. D.; Hill, R. G. (1997) Modulation of Long-term Potentiation in the CA1 Region of Mouse Hippocampal Brain Slices By GABA(A) Receptor Benzodiazepine Site Ligands. Neuropharmacol., 36, 823-830.

Small, G. W. (1997) Diagnosis and Treatment of Alzheimer Disease and Related Disorders. Consensus Statement of the American Association of Geriatric Psychiatry, The Alzheimer's Association and the American Geriatrics Society, JAMA, 278, 1363-71.

Sternbach L H, Fryer R I, Metlesics W, Reeder L, Sach G, Saucy G, Stempel A (1962) Quinazolines and 1,4-Benzodiazepines. VI. Halo-, Methyl-, and Methoxy-substituted 1,3-Dihydro-5-phenyl-2H-1,4-benzodiazepin-2-ones, J. Org Chem 27: 3788-3796, Whitehouse, P. (1998) The Cholinergic Deficit in Alzheimer's Disease, J. Clin. Psychiatry, 59, 19-22.

Yin, W.; Rivas, F.; Furtmueller, R.; Li, X.; Sieghart, G.; Wenger, G.; Cook, J. M. (2004) Synthesis, In Vitro Affinity and Efficacy of the First Bivalent Alpha 5 Subtype Selective BzR/GABA(A) Antagonist, Series Editor city.

Zhang, C., (2004) PhD thesis, University of Wisconsin-Milwaukee.

What is claimed is:

1. A compound selected from the group consisting of:

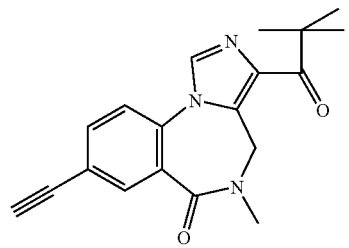

and a pharmaceutically acceptable salt thereof.

* * * * *

UNITED STATES PATENT AND TRADEMARK OFFICE
CERTIFICATE OF CORRECTION

PATENT NO. : 7,595,395 B2 Page 1 of 1
APPLICATION NO. : 11/383624
DATED : September 29, 2009
INVENTOR(S) : James Cook, Dongmei Han and Terry Clayton It is certified that error appears in the above-identified patent and that said Letters Patent is hereby corrected as shown below:

Column 1, Lines 11-16

STATEMENT REGARDING FEDERAL FUNDING
This invention was made with government support under MH046851 awarded by the National Institutes of Health. The government has certain rights in the invention.

Signed and Sealed this

Second Day of November, 2010

David J. Kappos
*Director of the United States Patent and Trademark Office*